(12) United States Patent
Richt

(10) Patent No.: US 7,867,710 B2
(45) Date of Patent: Jan. 11, 2011

(54) POLYMORPHISM IN BOVINE PRION PROTEIN GENE SEQUENCE

(75) Inventor: Juergen A. Richt, Ames, IA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 663 days.

(21) Appl. No.: 11/787,784

(22) Filed: Apr. 18, 2007

(65) Prior Publication Data

US 2009/0042185 A1    Feb. 12, 2009

Related U.S. Application Data

(60) Provisional application No. 60/793,760, filed on Apr. 21, 2006.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/6; 435/91.2; 536/23.1; 536/24.3

(58) Field of Classification Search .................. None
See application file for complete search history.

(56) References Cited

PUBLICATIONS

Sander P. et al. Neurogenetics (2004) vol. 5, pp. 19-25.*
GenBank Locus BTA000291 (2004), TPA: Bos Taurus prp gene for prion protein, from www.ncbi.nlm.nih.gov, printed pp. 1-25.*
Coulthart, Michael B., et al., "Prion protein gene sequence of Canada's first non-imported case of bovine spongiform encephaloopathy (BSE)", Genome, 46, 2003, pp. 1005-1009.
Brayton, Kelly A., et al., "A processed pseudogene contributes to apparent mule deer prion gene heterogeneity", Gene, 326, 2004, pp. 167-173.
Sander, Petra, et al., "Bovine Prion Protein Gene (PRNP) Promoter Polymorphisms Modulate PRNP Expression and May Be Responsible for Differences in Bovine Spongiform Encephalopathy Susceptibility", The Journal of Biological Chemistry, vol. 280, No. 45, Nov. 11, 2005, pp. 37408-37414.
Heaton, Michael P., et al., "Prion gene sequence variation within diverse groups of U.S. sheep, beef cattle, and deer", PRNP Nucleotide Diversity in US Sheep, Cattle and Deer, vol. 14, 2003, pp. 765-777.
Novakofski, J., et al., "Prion biology relevant to bovine spongiform encephalopathy", J. Anim. Sci., 2005, 83, pp. 1455-1476.

\* cited by examiner

*Primary Examiner*—Stephen Kapushoc
(74) *Attorney, Agent, or Firm*—John Fado; Randall E. Deck; Lesley Shaw

(57) ABSTRACT

A specific, non-synonymous SNP in the Prnp gene encoding the bovine prion protein affects the susceptibility of bovine animals to bovine spongiform encephalopathy (BSE). Depending on the number of octapeptide repeat units present in the Prnp gene, the position of the SNP is either nucleotide 631 of exon 3 (codon 211) when the Prnp gene comprises six octapeptide repeat region sequences, nucleotide 607 of exon 3 (codon 203) when the Prnp gene comprises five octapeptide repeat region sequences, or nucleotide 655 of exon 3 (codon 219) when the Prnp gene comprises seven octapeptide repeat region sequences. Alleles of the bovine Prnp wherein the SNP at these positions is lysine (K) at the corresponding amino acids (i.e., 211, 203 or 219) in the bovine prion protein are all indicative of increased susceptibility to BSE in comparison to alleles which encode glutamic acid (E) at the same position. This SNP may be used as a marker for selecting bovines susceptible to BSE for disposal and/or removal from breeding, the human food and animal feed supplies.

2 Claims, 7 Drawing Sheets

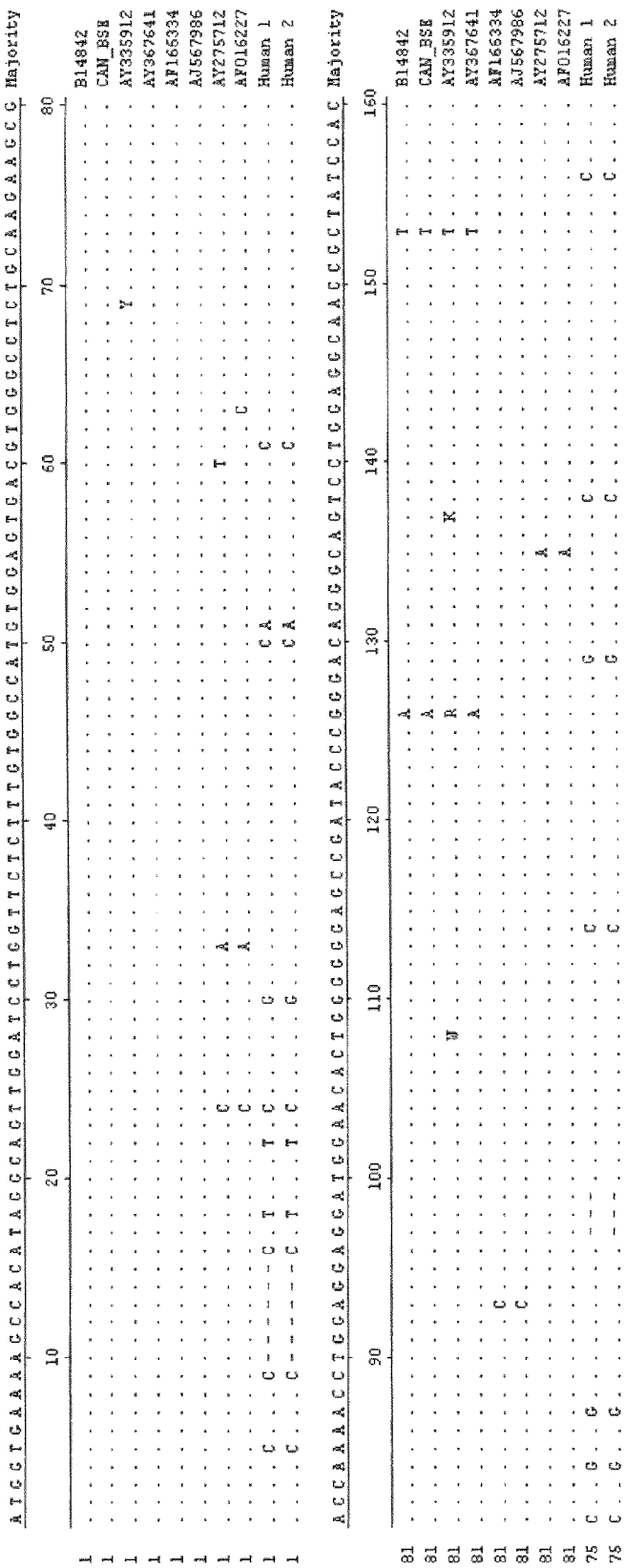
FIGURE 1A1

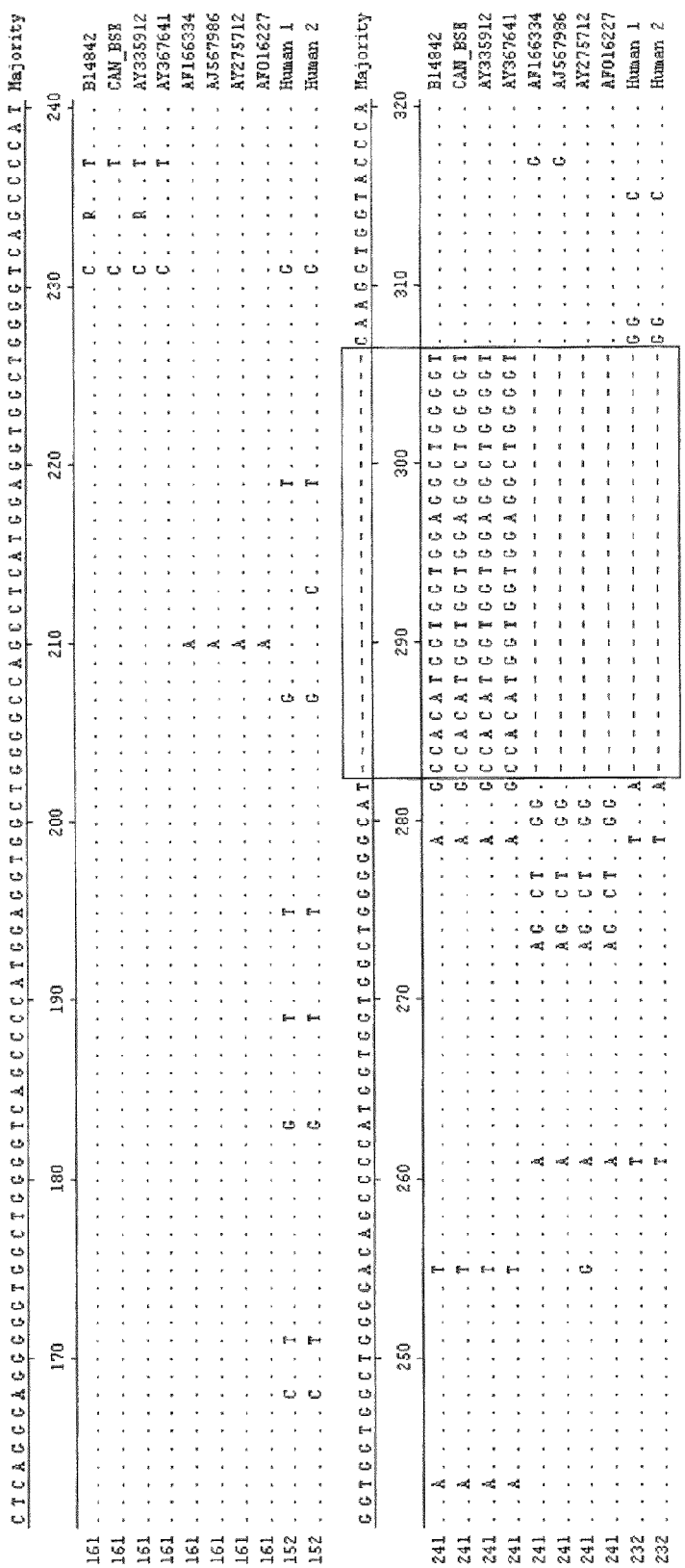
FIGURE 1A2

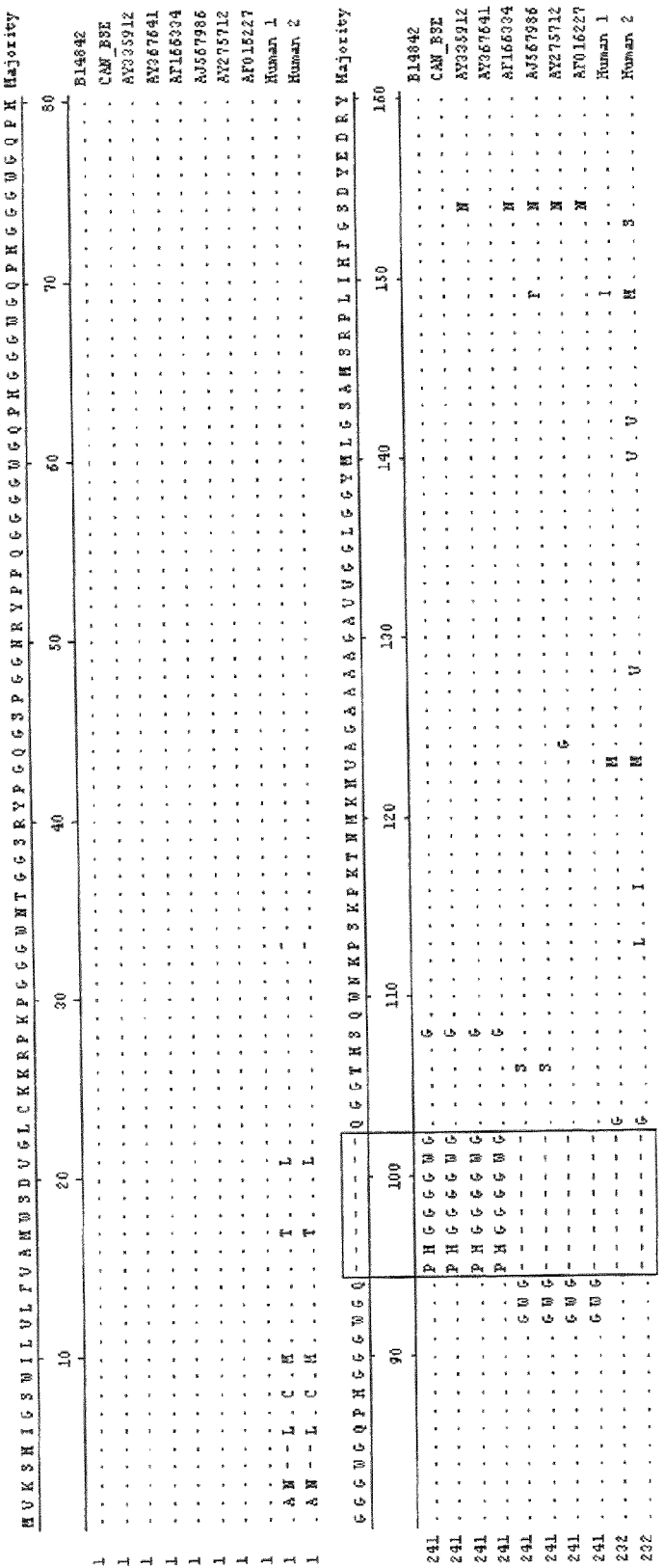
FIGURE 1B1

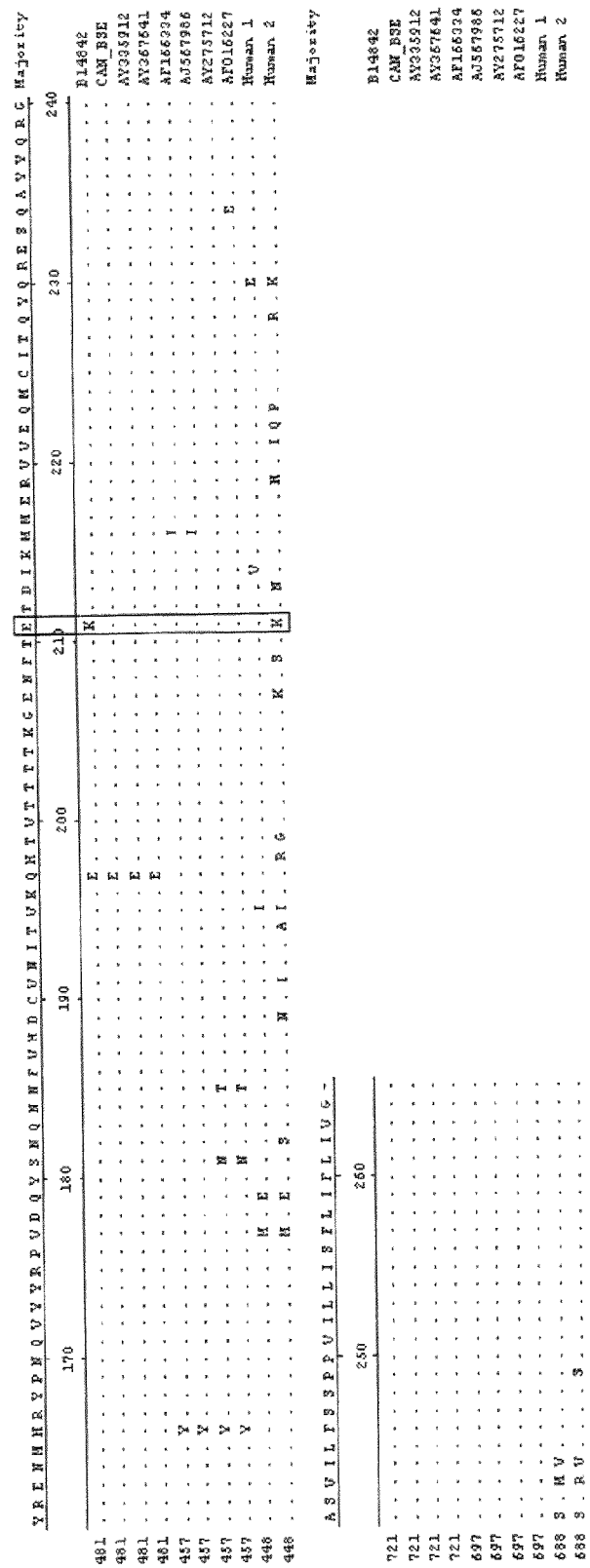
FIGURE 1B2

SEQUENCE LISTING

```
<160> NUMBER OF SEQ ID NOS: 27

<210> SEQ ID NO 1
<211> LENGTH: 78056
<212> TYPE: DNA
<213> ORGANISM: Bos taurus

<400> SEQUENCE: 1
taggaataat caatattgtg aaatgaccat ataccaaatg caacctacag attcaatgag      60
atctccatct aacttccaat agcatttttc acagaagtag aacaaaaaat ttcacaattc     120
atatggaaac acaaaaggcc ctgaatagcc aatgcagtcc tgagaaagaa gaatggagtt     180
ggaggattca accatcctga ctttagatta tactacaaag ctacagtcat caagacagta     240
tggtattggc ataaaaacag aaatatagac aaatggaaca agacagaaag cccagaaata     300
agcccatgaa cctatgggta ccttattcct gacaaaggaa gcaagaatat acaatggggc     360
agacagcctc ttcaataaat ggtgctggga aaactggaca gctacatgta aaagaatgaa     420
```

```
attagaacac ttcctaacac caacagttca gttcagttca gctggtcagt cgtatcgact    480
ctttgcaacc ccatggactg cagcatgcca ggcttccctt gtccatcacc aactcctaga    540
gcttactcaa actcatgtcc attgagttgg tgatgccatc caaccatctc atcctctgtc    600
gtccccttct cctcccacct tcaatcattc tcagcatcag ggttttttcc aatgaggcag    660
ttctttgcat caggtggcca aagtattgga ctttcagctt cagcattagt ccttccgatg    720
aatattcagg actgatttcc tttaggatgg actggtttga tcttgcagtc caaatgactc    780
tcaagagtgt tctccaacac cacagttcaa aagcatcaat tcttcagcac tcagcttcct    840
ttatagtcca actctcacaa ccatacatga ctactggaaa aaccatagct ttgactagat    900
ggagctttgt tggcaaagta atgtctctgc tttttaatat gctgtctagg ttggtcataa    960
ctttcttcc aaggagcaag catctttaat ttcatggctg cagtcaccat atgcagtgat     1020
tttgagccc ccaaaataaa gtctgtcact gtttccactg tttccccatc tatttgccat     1080
gaagtgatgg gaacagatgc catgatctta gtttcctgaa tgttgagttt taagtcaact    1140
ttttcactct cctctttcac tttcatcaaa aggctcttta ggtcttcttc tcttaaccat    1200
aaggatggtg tcatctgcat atctgaggtt attgatattt ctcctggcaa acttaattcc    1260
agcttgtgct ttatccagtc cagcattcct cgtgatgtac tctgcatata aattaaataa    1320
gcagggtgac aatatacagc ctcaatgtac tcctttcctg atttggaacc agtatgttgt    1380
tccatgtcta gttctaactg ttgcttccta acttgcatac agatttctca ggaggcaggt    1440
caggcgttct ggtattccca tctctttaag aatttcccac agtttgttgt gatccacaca    1500
gtcaaaggct ttggcacagt caataaagca aaaatggatg tttttctgga acgctcttac    1560
tttttcgatg atccaatgga tgttggcaat ttgatctctg attcctgtgc cttttctaaa    1620
tccagcttga acatctggaa gttcatggtt catgtacttt tgaagtctgg cttggagaat    1680
ttgagcatta ctttgctagt gtgtgagatg agtgtaatca tgcagtagtt tgagcattct    1740
ttggcattgc ctttctttgg gattggaatg aaaactgacc ttttccagtc ctgtggccac    1800
tgctgagttt tctaaatttg ctgccatatt gagtgcatca ctttcacagc atcatctttt    1860
aggatgtgaa atagctcaac tggaattcca tcacctcccc tagctttgtt cataatgatg    1920
cttcctaagg cccacttgac ttcacattct aggatgtctg gttctaggtg agtgatcaca    1980
ccatcatggt tatctgggtc atgaagttct ttcttgtaga gttcttctgt gtattcttgc    2040
cacctcttct taatatcttc tgcttttgtt aggtccatac catttctgtc ctttattgtg    2100
cccatctttg catgaaatgt tcccttggta tctgtaattt tcttgaagag atctctagtt    2160
cttcccattc tattgtctcc agggtgacca ccccagacc ctgtacctgg ggtcatataa     2220
ccacagtttc cacagtgaca tcccttccaa accctgaact tggggttgca cgtccatgtt    2280
ctccagcgtg acacccctc ttggaccatg cactggggtc acatgtccag gttccaggct     2340
aacaccccc cccatactct atacctggca tcaacgtcct catacagcag ggtgaccgaa     2400
ccctcaacat catgtacctg tgttgaaac tccacagttt ctgcacctca tcagaccttg     2460
tacctggagt cacatgtcca cagtctctag ggtgacagca cttaccaga cctttgacca     2520
gtgttcacac atccagtctc cagggtgatg cccacttcca gaccctgtac ctggggtaca    2580
tgttcacagt ctccagggtg acagcccccc agactctgta gctgggttaa cagacccacc    2640
tttccagggt gactacacca ctccatattg tgcacctggg gtcacacatc cacaatctct    2700
ggggtgacct ctcccagacc ctgtacgtgg gtcacacatc cacagtccca gggtgacccc    2760
```

```
acttcccaga ctgtggaact gggttcacat gtccacagtt tccaggtgaa tcccctccc    2820
caaagcctgt acctggggtc acacatccac agtctcaga  gtgaccctag cctccagacc   2880
ctctccctgg ggtcacatgt ccatggtcta cagggagata cccctcccag aacctgcacc   2940
tggggtcaca tggccacagt ctccagggtg aaccctacc  agaccctgta cctggggtca   3000
catgttcaga gtctcaggg  ttacctgcct cccagaccct gcaccttggt tcacatgtct   3060
gcagtctcca gtgtgacccc actcctgtac ctgtggtcac atgtgcagat tccagggtga   3120
caccctccc  agaccctgca cctggggtca cacgtatgcc atctccaggg tgaccccgcc   3180
tcaccagacc ttttacctgg ggtcacacct tcacagtctc cagggtaacc ccccaccca   3240
gactctgcac ttggggtaca atccacagt  ttccagggtg acacccctc  agaccttcta   3300
cctgaattca gagtttgata gcctcctggg agacccacc  acaccagcga gtgcacctgg   3360
cttcacacgt ccacagcgtc caggatgaca tgcccccaga ccctgtacct agggtcacat   3420
atctctagtt ccctggtgac ccctccaaga ccctgaacct gggtcatat  gtctgcagtc   3480
tccagggtga ccaaccacag acactctacc tggggtaata tattcacagt ctacagggtg   3540
acaacccact cagaccctga acctggggac acatgtccac ggtctccagg gtgatcacac   3600
actccagacc ctgtacctgg ggtcacatat ccacagtctc cagggaaacc caactgccca   3660
tactgtgcac ctgggggtca cacatccagt ctccagggtg accccccgcc ccatatcctg   3720
taccttgggc cacatgacct cagcctccag ggtgacccca ccctcaacat catttacctg   3780
gggccaaatc tccacactct ccagggtgac ctcctcccag accctgcacg tggggtcaca   3840
tgtccacagt ctccagggtg accccatgtc acagatcctg cacctgagtc acatgtcaac   3900
cgtctccatg gtgaccccte ccagactgca cctggggtca catatccata gttcccatgg   3960
tgatcccacc ctggccctgt acctgtggtc acatgtccac agtttcaggg tgagttccct   4020
cccacgttct gtacctgagg tcacatgtcc atagtctcca gggtgacccc atcttctaga   4080
cattgtacca gggttcacag atccacagtc tccagggtga tctccctctc catacccgt   4140
acctggggtc aacatcctca gcttccagga tgacccaatc ctcaacatcg tgtaccgtgg   4200
gtcaaacgtc cacagtctcc agggtcactg cacctcacta gaccttgtac ctggggtcac   4260
atgtgcacag tctctagggt gacattacct caacatacct tttaaatggg ttcacacgtc   4320
cacagtctcc cagggtgact cccctctcag cctcctgcac ctgagataca cattcacagt   4380
ctccagggtg acatcccccc cagacactgt acctgggttc acaggtccac ctcctccagg   4440
gtgacctcac cacaccagac cacgcacctg tgatcacaca tccacagtgt ccagggtgac   4500
accctcccag atcctgtacc taaggtcaca tatctacagt tccctgagag acctcccaa   4560
accctgtacc tgggtcacac atccacagtc ccagggtgac cccacttccc agactgtgaa   4620
accgggttca catatcaata gttttccaggt gaattcccct ccccaaaccc tgtacctagg   4680
gtcacacgtc cacagtccca gggtgaccct agcctctacc tggggtcaca tgtccacatt   4740
ctacagggtg acccccctcc caggccctgc tcctagggtc atatggccag tttccacagt   4800
aaacccttcc cagaccctgt acctggggtc acatgtccag agtctccagg gtgatccaca   4860
tcccaaactc ttcacctggc atcacacgtc catagtctca agggtgacac cctcccagac   4920
tctgaacctg gggtcacatg tccacagtct ccagggtgac ccccaccgga ccctgccct   4980
ggggtcacac gtcttcagtc tccagggtga caccctccc  cagacactgt aactagagcc   5040
acatgtccac agtctacaag ggtgaacccc gccccccccc cataatcgc  atgtgggttc   5100
acatatccac agtctccttg gtaaccttgc ttcccagtaa cggcacctgg attgcacatc   5160
```

```
cacagtcttc atggtgaccc cctcccagac tctgcacctg agttcaaatg tctacagtct    5220
ccagggtgac ccctcccaaa ccctgcagag ggcctcacat gtccacagtc tccaggctga    5280 accccccctcc cagaatctat acctggagtc acatgtccac agtctccagg gtgacacccc    5340
ctcccccaga ccttgggggt cacattgaaa cagtctccag gtgaccatct tcccagaccc    5400
tgcacctagg gtcacaagcc cacatctcca atgtgacccc tctcctgctc caggggtcac    5460
atgtccacaa attccaaggt gacacctctc ccagacactg cacctgggtt cacatgtccc    5520
actgtctcca gggtgacaac ccccatactc tgtacctggg ttcacaggtc cacagtctct    5580
agggtgactc tgccacatca gactgcacag ctgtgggcac atgtccacag tttccagggt    5640
ggcaccctcc cagatcctgt acccagggtc acatatttac agtcccctgg gttaacactc    5700
ccagaccctg tacctgaggt catttgtcca cgttgtccag ggtcaaccct tcccagaccc    5760
tacacctcgg ctcacatgtc cacagtctcc agggtgacct cctcccaacc ctgaacttgg    5820
agtcacatgt ccagtctcta gggtgatcac ccccataccc tgtacctggg atcacaaaac    5880
tacagtctcc agggtgaccc tgtgcccaga cactgaatct ggggtcacac atccacagtc    5940
tccagtgtga tgcccactcc cagaccatgc accagggggtc acatccac agtctccagg    6000 gtgacagcct ctgagaccct gaacctgggg tcacatgccc acagtctaca gggtgacgac    6060
ccctcccaga ccacatacat gggttcacag gttcacagtc tccaggataa caccctccca    6120
gaccctgtac ctatggacac ctatctacaa tccccttggt gtcccctccc agacactata    6180
cctgggttca catgtccaca gtcttcaggg tgacacccctc cagaccctgt acctagggac    6240
acctatctac agtcccccttg gtgtcccctc ccagacacta tatctggatt caaatgtcca    6300
cagtctccag gttgaccccca ccctcaagaa cctctacctg tagtcatatg accacagtct    6360
ccagtgtaaa cccacctccc atatcctgca cctggagtac atgtccagtc tccagggtga    6420
ccccacagtc cagaccctgt acatagggtc acagacctca gcctcaagag tgatactctc    6480
ccagagtttt tacctggggc acatgttca tagtctccag ggtgatcctc tctcaactct    6540
gcacctgggg tcacacatac aaagtctcca ggtaacaccc cccaataccc tgtgcctggt    6600
gttgcacatc cacagatttc acagtgaccc cacctcccgg accctgcatc tgaagtcaaa    6660
tgcccacagt ctccagtgta aactcacatc ccatgctgtt cctggggtaa atgtccacat    6720
tatccaggat gaccccacct cccagaccct gttccttggg tctcacttac acagtctcca    6780
gagtgtcccc acctctcaga ccctccatct gggatcgaac attgccagta tccagggtga    6840 cccccctccca gactctacac ttggggtcac atgtccagag tttccagggt gactgcctcc    6900
cgaacctgta gctgtggtca caggtccaca gtcttcaggg tgacacccct ctccagacaa    6960
tgtatctgga gtcacacatt cacagtctgc taggcgaacc cagcccccaa accctgcaca    7020
tgggacccca tgttcagtgg ggagtgttga ctaccagcct acaacaacca gctgctgtt    7080 gctgtcagca gcctaattgg gtgaaaaatg gactgggtga tgacttccca ataagaagtg    7140
gcaagtagca tgttcctttc agaaaactca aataatgaac caaagttgtt gtcataatgt    7200
acagacaaat gacctggtgt gtttcttcat ggttggttga gtctgcaact atccaccttt    7260
cccaggatga tcatatagat tttgccatat tactttgatt ccagcctcaa cataacatgt    7320
ttccctgtac atttagagct gggtaaagac actcctggag aaggcaatgg caccccactc    7380
cagtactctt gcctggaaaa tcccatggat ggaggagcct ggtaggctgt agtccatggg    7440
gtcacgaaga gtcagacaca attgagtgac tttactttca cttttcactt tcatgcattg    7500
```

```
gagaaggaaa tggcaaccca ctccagtgtt cttgcctgga gagtcccagg gacggggggag   7560 cctggtgagc tgccatctat ggggtcgcag agtcggacac gactgaagca acttagcagc   7620
agccgcagca aagacactcc tagtgtacaa acactgtaca gtttgaggag tatagacagc   7680
agtggagagt gctctatgaa tgtggatggc caggtctgtt tttaccctga gtaggtgaaa   7740
cgtactgtca ggtgacctca cagcaagaag tggcaagctg cctgtcatga gaagtgaagt   7800
tgcccactca tatgcgactc tttgcaatcc catggactgt agcctatgga ggtcttctgt   7860
ccatggaatt ttccagtcaa gagtactaaa gtgggttgcc aattcttttt ccagggaatc   7920
ttcgcgacct gagtatcaaa cctggtctc  ccacatcgca ggcagacact accctcttag   7980
ctaccacgga agcccaccag attcattgaa aactcaactg tttacccgaa gttgttctgg   8040
gattgaagag tagaatgagc ctgctgtgtt tttctgccag gtgggatgct gtaactacac   8100
aggtttcaca gggggaaatg actgctttgg aacgtccgat cccaattcca ggttcacaaa   8160
aagttgtctc cctgcagttt taaagctgtg taaatgcctt cctaggacac aatgggctct   8220
ctgtgaatgt tgacttctgt atgtgttctt accctattca gcgaaaacag tactgtcaga   8280
ggacttccca tcaagaagtg gcaagcagag tgtttctctc aggtaacaga agtacttgat   8340
gagacttgca gtcctaaaga agggaaaaac gacccgtgtg cttttccgtc aggctggaga   8400
ttgcaagtat tccaggtttg ctaggtgaaa atactgcttt ctcttcaggc cccgagttct   8460
acgttcagag aaacatttcc acacaggttc agagctgtgc caagattcca agaacacact   8520
gtacaatttc tcagaaaaga cttcagtgaa gaatgtcctg caagtggttc tgccataatt   8580
gttaccctga gtgggtggaa ttacactgtc agatgacttt ttagcattaa aaagcaagtg   8640
cctatgcttt cagaaaaggc agatactaaa gctgcgctcg taagaaacag gcaaatgaac   8700
ccgtgtgcat ttcttt cagg cttaagactg caaccaccct gcagttacac gaaaaagtgc   8760
tgcttctgcc attaggctcc aaatcccatg tgaacagaaa taaatccccc tgtcattaga   8820
aagctgtgta agtgagccca ggccagaatg caccatacca tgagtaaaga ggtcagtggg   8880
gagtgttctg agagttcaat agtgagtgtt ctggaagtgt tgactgccat acctgtagtc   8940
agcagcctaa tttggtgaaa ctggactggg tgatgacttt ccagtaagaa ggagcaagct   9000
gcaattacct ttcagaagac tcataatggc ccaaagctgt tgtaataatg cccagacaaa   9060
tgagtcactg cgtttcttcc tagctggttg gtggctgcaa ctatccaggt ttaaggggag   9120
gaatatactg actttgccat attaccttat ttgcagcttc aggtaacata tttccctgca   9180
catttagagc tgtgtaaaga cactcctaga gaacaaactg taccatttgt ggagcaaaga   9240
tagcggtgga gagtgctctg tgaatgtgga tggtcaggcc tgttttttagc ctgatgaggt   9300 gagatgtaat atcaggtgac ctcacagcca gagtggcaag ccacctgatt catgagaagt   9360
gaagttgctc agttgtatgt gactctttgc actcccatgc aatgtagctt accaggctcc   9420
tttttcgatg gaattttcca ggcaagaagt actggtatgg cttgccactt ccttttccag   9480
gagatattcc tgacccaggg atcacacccg ggtcttcaat gttgcaggca gatgctttac   9540
cctctgggtc accagaatcc ggctggattc attgaaaatt cactgattta acaaaagctg   9600
tcctggaatg gaagagtaga atgagcctgt tgtatttctc tggcaggtgg tatgctgtaa   9660
ctacaaggct tcacaaggac gaatgctttg ggacatcagt ccccaattcc acgtgcacaa   9720
aatgacatct acctatagtt tcaaagctgt gtaaatccat tcctaggaca caatgggcta   9780
tccgtgaagg ttgactttg catctgtttt tacactgatc agctaaaact gtactgtcag   9840
tggacttccc atcaggaagt ggtaagcaga atgtttctct cagaaaacac aagtccttga   9900
```

```
tgagacttgc ggccctaaag aagggaaaat gcccccgtgt gttttctgtc agtctggaga      9960
ctgcaattat tccaggttcc ttaggcacag attttgcttt catttcaggc cctgagttct     10020
aggttcagag aaacatttcc ccacagcttc agagctgtgc aaaacactcc tagaacacac     10080
tgtatcattc ccttagacaa gagaccaggg aagagcattc tgtgagcgct tctgcgatat     10140
cagttgttac cctgagtggg aagaattaca ctgtcaggtg acttggtagc attaataagc     10200
tagagtctgt gctttcagaa aaagcagaca cttttagcaa agttgccttc gtaaggaagt     10260
ggaaaatgaa cccgtgtgcc tttctttcag gcttaagact gcaatcaccc tgtggtcaaa     10320
aaagaaatac tgcttctgac attaggctaa aaagcccaca tgaaccaaac aaatgcccct     10380
gtcgttagaa agctgtgtaa gagacccaag gacagactgc accagtccat gagtaaagag     10440
ttctggggggg agtgttctct gggtgttgac tgccatacct gtagtcagca gcctaattcg     10500
gtgaaactgg actgggtgat gacttcccag taagaagtgg caagctacat gttccttttg     10560
gaagactcaa agaatggcca aaagctgttg tcataatgcc cagacaaacg agccagtgca     10620
tttcttgctg gttgaaggct gcaactatcc agctttcagc agaggaatat tctgattttg     10680
ccatattacc tggatttgca gcttcaagat aacacatttc cctgcacaag tagaggtgtg     10740
taaagacact cctagtgtac aaactctgta ccacctgggg aacaaagata gcgtggacag     10800
tgctctgtga atgtggatgg ccaggcctgt tttcaccctg aagaggtgaa aagtactgtc     10860
gggtgacctt gcagccagaa gcggcaagac gcctgcttca tgagaagtaa agttgttcag     10920
tcattgcgac tctttacaat cccgtggact gtagcttacc aggctcctcc atccatggaa     10980
ttttccaagc aagactactg gagtggcttg ccatttaatt ctcaatggat cttcctgatc     11040
caaggatcaa acccaggtca cccatgttgc aggcagatgc tttacccttt gagccaccag     11100
ggaagcctgc cagattcatt gaaaattcaa ctacttaact aaagctgttc tggaatggaa     11160
cagcagaatg agcctgttgt gttttctgg caggtgagct gctgcaacca cacagtttcc     11220
caagggaaa tgactgtttt gggatgtcag accccatttc caggtgcaca acaggacgtc     11280
tccctgaaga ttcaaagctg tgtaaacgca ttcctaggat acaatgtgct ctctgtgaat     11340
gttgacttt gtatctgttt ttctactgat tagctaaaac tgtactgcca agggacttcg     11400
catcaaaaag tggcaagcag acccatggtc ctaaagaaga gaaaaatgac cccatgaact     11460
tttccatcag gctggagatt gtaagtattc caagttcatt agtaacaaat gctgctttca     11520
tttcaggcca ccatttctag gttcagagaa acatttcccc gcagattcag agctgtgcaa     11580
agacactcct agaacacact gtatcattcc ctaagaaaag agttcaggga agagtgttct     11640
gtgagtactt ctgccatacc tgttgttacc ctgagtgggc tgaattacag tgtcaagtga     11700
ctacgtagca ttaaaaagca agggcgtgtt cttttttgaaa acacagatac gtaagtaaaa     11760
ctaccatcat aaggaagagg caaatgaatg caagtgcatc tctttcaggc ttaggactga     11820
aaccacgctg cagtcacacc aagtgctgct tctgccatta gtctctgaat cctacgtgag     11880
cataaaaaaa aaaaaaaaaa aatccctgtt gtgagaaagc tgtgtaagag accccaagga     11940
cagattgcat cattccatgg gtaaagagtt cagtgaggag tgttctggga ctgttgactg     12000
ccatacctgt tgtgagcagc ctaattttgg tgaaactgga ccagttgatg acttcccagt     12060
aagaagcggc aagctgcaca ttccttttgg aagactcaaa gaatggccga aagctgttgt     12120
cataatgccc agacaaatga gccattgtgt ttcttcttgg ctgtttggag gctgcaacta     12180
tacatctttc acaggaggaa tatactgact ttgccatatt acccagattt gcagcttcaa     12240
```

```
gataacacat ttccctgcac atttattgct gtgtaaagac acttctagtg tacaaattct   12300
gtgccgtttg tggagcaaag atagcagtgg agagtgctct gtgaatgtgg atggccaggc   12360
ctgttttcac cctgatgagg tgaaaaatac tgtcagatga ccttgaacca agaagtggca   12420
agccgcccgc ttcatgagaa gtgaagtttc tcagtcatgt ttgactcttt gcaatcccat   12480
ggactgtacc ttaacaggct cctcagtcca cggaattttc caggtaacag tactagagtg   12540
gcttgccatt tccttctcca gggcatcttc ctgacccagg ttttgaatgc gggtgttcca   12600
ctttgcaggc agccgtttta ccctctgagc caccaggaaa gcctgctggg gtttacagaa   12660
aattcaactt cttaaccaaa gctgttctgg aatgaaaaag tagaatgagc ctgctgtgtt   12720
tttctggcag gtgggatgct gaaaccacac aggttaccca aggggaaatg actgctttgg   12780
gacatcagac accaattcca ggtgcacaaa agatgtctc cttgcagagt caaagctatg   12840
taaatgcatt cctaggacac aacgtgttct ccgtgaatgt tgactttgc atccctttt   12900 gcactgatcc tctaaaactg tactgtcaga ggaattccca tcaagaagtg gcaagcagac   12960
ttgtagtgct aaagaagggg aaaatgcccc cgagagcttt ctgtcaggct ggagattaca   13020
agtattccaa gttcattagt aacatatgct gctttcattt cagggcctga gttctaaggt   13080
tcagagaaac atttccccat agcttcagag ctgtgcaaag cgactcctat cacacactgt   13140
atcattgcct tagaaaagag ttagggaaga atgctatgtg agtgcctctg gcatacctgc   13200
tgtcaccctc atgggctgaa ttacactgtc aactgactat gtagcattaa tcagcaagtg   13260
cctgttcttt caccaaacgc agatatataa gctaagctgc ggtcatgagg aaaaggcaaa   13320
tgaacccatg agtgtttctt tcagggttaa aagtgcaagc accctgcagt cacacgaaga   13380
aatgctgtgt ctgcctttag gcaaaaaatc acaggtgaac ataaacaaat atccctgtcc   13440
ttagaaagca gtgtaagaca gcccagggac atattgcacc attccatgag taaagagttc   13500
agtgaggagt gttctgggat acctgttgtc agtagcctag tcggtgaaac tggactgggt   13560
gacgacttcc cagtaagaag tggcaagccg caggttcctt ttggaagact caaagaattt   13620
cccaaagctg ttttcataat gcccaggcaa atgagccagt gcgtttcttc atggctgatt   13680
gcaggctgca actatccagc tttcacagta gaaatatact gattttgcca tataacccag   13740
atttccagct tcaagagaac acatttccct gctcatttag tgctatgtaa agacaccct   13800 agtgtataaa ttctgtacca tttgcagagg aaagagcagt ggagaatgct ctgtggatgg   13860
ccaggcctgt ttttaccctg aagaggtgaa aagtactgtc aggtgacctc gaatcaagaa   13920
gtggcaagcc tcccgcttca tgagaagtga aggtgctcag tcgtgttggc tttatgcaat   13980
cccatggact gtagctgacc aggctcctct gtccatggaa tcttctaagc aagaagactg   14040
gagtgacttg tcatttcttt ctccagggaa tcttcccgac acaggatcga tccctggtct   14100
ccctcattgc aggcagacgc tttaccctct gagccaccag aggaacccgc cagattcact   14160
gaaaagtcaa ccacttactg aaagctgctc tagaatggaa gagcagaatg agcctgctgt   14220
gtatttctgg taggtgggat gctgcaacta caaaggttta ccaggggaaa tgactgcttt   14280
gggacattag tctccatttc caggtggaca ggacgatgtc tctgcacttt tcaaagctgc   14340
gtaaatgcat tcctaggaca caatgtgctc tccaagaatg ttgacttttg catctgtttt   14400
tgcactgatc agctaaatct gtaccgtcag aggacttccc atcaagaagt gacaagcaga   14460
ctttggtctt aaagtaggga aaaatgcccc tgtgagcttt tccggcagga tggagattgc   14520
aagtattcca ggttctttag gtgcaaatgc tgctttcatt tcaggcccca agttctaggt   14580
tcagagaaac ggtttgccca gcttcagagc tgtgcaaaga cactcctaga acacactgta   14640
```

```
tcattcactt agaaaagagt ataaggaata gtgttctgtg attcatctgc catacctatt    14700
gttaccctga gtgggccaaa atacactatc aggtgacttt gtaacattaa caggcaagca    14760
cctgtgcttt cagaaaatgc acatacttaa gcaaagctgt ggtcgtaaag aagaggcaat    14820
gaacccatgg atgtttcttt cagggttaag gttgtaacca ccctgcagtg acacaaagaa    14880
gtgctgcttc tgccattagg ctaaaaatcc ctggtgaacc aaacaaaagt cccctgtca     14940
ttagacagct atgcgactga gtccaaggac agattgcacc attccatgtg taaagagttc    15000
agtggggagt gttctgggac tgttgactgc catacatgtt gtcagcagcc taattcagtg    15060
aaactggact ggatgatgac ttcccaatag aagtggcaa gctgcatgtt cctttcagaa     15120
gactcaaata atggtacaaa gctgttgtca taatgctcaa atgagacagt gcatttcttc    15180
cttgctggtt agaggctaca atccaggttt cacaggaggt atatactgat tttggcatat    15240
tacccggatg tgcagcttca agataataca tttcccagca tttagagctg tgtaagacac    15300
cctagtatac aaactctgta ccatttgtgg agcaaagacg gtagtggaga gtgctctgtg    15360
catgtggatg gccaggcctg tttttaccct gatgaggtgg aaagtactgt tgggtgacct    15420
tgcagccaga agtggcaagc tgcctgcttc atgagaagtg aaattactca gtcgtgtggc    15480
tttctgcaat cccatggact gcaccttacc agactcctcc atccatggaa ttctccatgc    15540
aagagtactg gaatggcttg ccatttcctt ctccagaggg tcttcctgac ccagggatag    15600
aacccaagtc ccccatgtgg caggcagaca ctttaccctc tgagccacta gggaagtgtg    15660
ccagattcag tgaaaactca actacttaac caaagatgtt ctggaatgga agagcagaat    15720
gagcctgttg tgtttttctg gcaggtggga tgctgcaacc acacaggttt ccccaagggg    15780
aaatgactac tttgggactt gagaccccaa ttccagttgc accagaagac atctccctgc    15840
agtttcaaag ctatgtaaat gcattcctag acacagtgt actctccatg aatgttgact     15900
tttgtatctc tttttgcact gataagctaa aactgtactg ttagaaactt tccatcatga    15960
aagggtaagc caacttctgg tcctaaagaa aggaaatgtg ccccgtgag cttttctgtt     16020
aggctggaga acaagtact ccatgtttgt taggcgcaaa tgctgctttc atttcaggcc     16080
ctgagttcta agttcagaga acatttccc cacagcttca aagctctgca aagacactcc     16140
tagaacaaac agtatcattc acttaaacaa gagaccaggg aggagtgttc tgtgagtgct    16200
tctgccatac cagttgtttc cttgagtggg cagaattaca ctgtcacatg acttcgtagc    16260
aacaataggc aagaggctgt gctttcagaa aatgcagaca cggtctgcat tttagcaaag    16320
ctgtgatcct aaggaagaag caaatgaacc catgtgcatt tctttcaggc ttaaggctgc    16380
aaacaccctg cagtcacatg aagaagtgct gcttctgcca ttagactccg aaccccatgg    16440
gagcattaaa aaatgtccct gctgtgagaa agctgtgtaa gagaccccag acacactgc     16500
accattccat ggaaaaagag ttcagtggga tatgttctca gagttcagtg tggagtgttc    16560
tgggactgtt aactgccata cctgttgtca gcagcctaat ttcataaaat tggactgggt    16620
gatgacttcc cagtaagaag tggaaagctg cacgttcctt tcggaagact caaagaatgg    16680
ccgaaagctg ttgtcataac gcccagacaa atgagccagt gcatttattc ctggctggtt    16740
ggaggctgca actattcagc tttcgcagga caaatatact gatttttcca ttttatctgg    16800
atttgcacct tcaagataac acattcccct gcacatttag tgctgtgtaa agacactcct    16860
aatgtacaaa ctctgtaccg atgtggagca aagacagtag tggacagtgc tctattaagg    16920
tggatggcca acctgttttt accatgatga ggtggaaagt actatctgat gacctcacag    16980
```

```
tcagaagtgg caagccgcct gtttcatgag aagtgaagtt tctcagtcgt gtgcaactct    17040
ttgcaatccc atggattgta gctaaccagg ctcctctgtc catggaattt tccaagtaga    17100
ctagagtggc ttgccatttc cttctccagg ggatcttcct gacccaggga tcgaacccgg    17160
gtctcccaca atgcagacag acactttacc ctctgaacca tgggtccatt gaaaattcag    17220
ctacttaacc aaagctgttc tggaatggaa gagtagaatg agcctgttgt cttttttctgg   17280 caggtgggat gctgcaacta cacaggtttc ccaaggggaa atgactgctt tgggacatca    17340
gatcccaatt ccaggtgcac aagacatttc cctgcagttt caaagctgtg caaatgcatc    17400
ctaggacaca atgtgctctc tgtaatgctg acttttttat ctgcttttc actgatcagc     17460 taaaactgta ctatcggagg acttcccatc aagaaatggc aagtagcgtg tttctctcag    17520
aaaacataag tacttgatga gacttgtggt cctacagtgg gggaaaatgc ccccgagtgc    17580
ttttccatcc tgatggtgat tccaaatatt tcaggtttga tgggcacaaa cgctgctttc    17640
atttcaggcc ccgagttcta ggttcagaga aacgtttccc cacagcttca gatctgtgca    17700
aagacactct tagaacacac tgttaccatt cccttagaaa acagaccagg gaagagtgtt    17760
ctgtgagtgc ttctgccata ccagttgtta tcctgagtgg gcagaattac actgtcacgt    17820
gactttgtga cattaataag caagcgcctg tatttcagaa aatgcagaca ctttagcaaa    17880
gttgcctttg taaggaagag gcaaatgaac ccatgtgcgt ttctttcagg cttaagattg    17940
caaccaccct gcagtacacg aagaaatgct gcttctccct aggctccaaa tcccatgtga    18000
accaaatgtc cctgcaaata gggaaaaatc agtatgttcc tcctgggaaa gcaggagagt    18060
tgtagcctcc agccagccac gaaaacaccc cagggcattc cattgctcat tatgacaaca    18120
gctttggtca attatatgag tttgctgaga ggaacatgct acttgccact gcttactggg    18180
agttatcacc cagtccactc tcaaagaaat aggctaacca caggtatggc agtcagcagg    18240
cacagaaccc tccccactga actctcagaa ccctcccccac tcaactctta actcttggaa    18300
tggtgcagtc tgtccctggg ctctgtgaca cagctctcta actacaggga cgtttgtctt    18360
cttaaaacgg gatttggagt ctaatagcag aagcagcatt tcttcgtgtg actgcagggt    18420
gcttgcggtc cttagcctga aagaaacaca catgagttca ttttctctt cctgaagacc      18480 ggagctttgc taaagtatct gcgttttctg aaaacatagg cacttgcata ttaatgctac    18540
aaagtcattg gacagggtcc tttggcccac tcagggtagc aagaggtatg gcagaagggc    18600
tcacagaaca ctcttccctg aactcttttc taagggaatg gtacagtgta ttctaggagt    18660
gtctttcccc agctctgaag ctgtgggaaa acatcttac tgaacctaga actcggagcc     18720
tgaagagaaa gcaaccttttt cccctaacaa aacttgaata cttgcagtct ccaacctgac   18780
agaacaccac actggtgcat tccccccttc ttcatgacag caagtttcat caagtacttg    18840
tgttttctgg gagaatcacg cttcttgcct tttttttgtg ggaaagtcct ctgacagtac    18900
agttttaact gttcgggata aaaataggca gagaagtcaa cattcacgga tagtacattg    18960
tgtcctagga acggactcac tcagctttga aactgcaggg agacgtgtgt tttactacct    19020
gggattggct tagggcatca aacagcagtc atcttctgtg aaacctgtat cattgcagca    19080
accaacctgc cagcaaaccc acaggctcat tctattcttc agtcctagaa cagcgttggt    19140
taaggagctg agttttttagt gaatcaggcg ggcttcccgg tggctcaggg ggtagaacat   19200
ctgcctgcaa tgcgggacac ctgggtttga tccctgggtc gggaagttcc acccaccaga    19260
gaaggaaatg gcaacccatt tcagtactct tgcctggaag ctacagtcca tgggaaagag    19320
tcgaacacaa cttagcagct tcatatctca tgaatcaggc tgcttgccac ttcttgctgt    19380
```

```
gagctcatct gacagtacat ttcacctaat cagagtaaaa cagccttggc catccacatt    19440
cacagagccc tctccattta tatctttgct cagcacatgg tacagtgtat gtacactagg    19500
agtgttaaca tgggatttgg agcctaatgg cagaagcagc atttctttgt gtgactgcag    19560
gtggcttgca actccttgca tcaaggtcct ttccattgga atgtcaactc atctaggtaa    19620
caacactatg gcactcagca ctctcaaata ctctcccaca gattttcctc atgggcagtc    19680
ccagtatgac caaggaatct gttcactagt ctcagaaagt ggagggaaac atactggctg    19740
tgactctcaa aattagggcc tgtgtgcaaa tgtggtgttc tcacatcata aaatctagac    19800
agctgctgag agagagatgc ctgaaaatca ctcttttttc gcctttcatg catcaaagca    19860
ctgtacgttt cccagcgttc tgtttgctga gagtaaccca ctacttgtga atccttgctt    19920
ggaggtaaca atttcccctc acctgtttca cagtacagaa ggaaagcata atcgctgctg    19980
cggccgctaa gtcgcttcag tcatgtctga ctgtgcaacc ccatagacgg cagcccacca    20040
ggctcctctg tccctgggat tctccaggca agaatattgg agtgggttgc cacttcttct    20100
ccaaagcata atcacaggga gaaacaagac aaaaacccca agttccaaca acttttctct    20160
gtaggaagga tccagtgatc ctaggtctgt cttgaaaatt cttggatact gcagggatac    20220
ctactgagtg tgaacctgga tattgcacct tgatgacaaa attagcattg tctcttggtt    20280
gactctagaa ggctggggtt tagcaactgc ctgaaaatct atccaatgtt gttttcgtac    20340
tttgacagca atagctttgg ttaaaaacat tgggatttct gaagcaagta ggcagcttat    20400
aagttcttgt gtcaaggtcc tttccaccag aatgtcaatg aatctaggta acaacagtat    20460
ggcactcagc actctcagtc actctcgcgc agactgtttc ttcatgggca gtcccaggat    20520
gacctaggaa tgtattcacc aggctcagaa agtgcagaga acataccag ctgtgactgt     20580
ccaaattaca gcctttgtgc aaacgtggtc ttctcatatc atagaatcta gacagttgct    20640
aacaggtagg tgcctgaaaa acactcccct tttttgcctt tcattcatca aagaaacata    20700
ggtttcccaa cattctgttt gctgagaata acaacactac ttgcaaatct gtgcttggag    20760
gtcattttaa ctaacaatta cccctcacgt gtgtcacagt agggaaggac tgcctacgta    20820
cagggaaaaa caaacaagcc aaaaaactca agttccttac attgcctctg tagaaaagat    20880
ccagtgatcc taggtctgtc agggacacac actgcgtgtg aacctggata ctgaaccttg    20940
ctggcaaaat tagcattttc tctcttatgg ccctgaaatg gtgcagccta gcaactgcct    21000
gaaaatccat acaattttt ccctactttt tgacaccaat agctttggtc aaaaattggg      21060
atttctgaag caagcagggg gcttgcaact ccttgcgtca aggtcctttc ctttgggata    21120
tcagctaatc taggtaacag tggtatggca ctcagcactc tcagtactc tcgcacagac     21180
tgtttcctca gggatgtcac aatatgacct aggcatgtgt tcacaaggct cagaagggc     21240
agggaaataa actggctgtg actctcgaaa ttacatcagg agggatgctg caactgcaca    21300
gggttcccag ggggaaacga ctgctctggg gcatcagatc ccaattccag gtgcacaaga    21360
agacgtctcc ctgcagtttc aaggctgtgt aaatgcattc ctaggacaca gtgtgctctt    21420
cgtgaatggt gacttttata cgttttttgca ctgatcagct aaaactgtac tatcagagga    21480
cttcccatca agaagtagca agcagtgtgt ttctctcaga aaacacaagt acttgatgag    21540
acttgcggtc ctacagcagg gaaaattgct cctgtgtgtt tttccatcag gctggagatt    21600
gcaagtattc caggttcatt aggcgcaaaa tgctgctttc atttcagacc ccgagttcta    21660
ggttcaaaga aacatttccc cacagcttca gagctgggca aagataccc tagaacacac      21720
```

```
tgtatcattc tcttaggaaa gagaccaggg aagagtgttc tgtgagttct tctgccatac   21780
ctgttgttac cctgagtggg cagaattaca ctgtcgggtg atttgaggca ttaataagca   21840
agtgcctgtg ttttcagaaa acgcagacac tttagcaaag ttgccattgt aaggaaaagg   21900
caaatgaacc catgtggttt tccttcaggc ttaagactgc acccaccctg cagtgacgga   21960
agtgctactt ctgccattag gctccaaacc ccatgtgaac ataaacaaat gtccctgtca   22020
ttataaagct gtgtaagaga actcaaggac agactgcatc atttcatgag taaagagttc   22080
agaagggaat gttctgggag tgttgactgc catacctgtt gtcagcagcc taatttggtg   22140
aaactggact gggtgatggc ttcccagtaa gaagtggcaa gttgcatgtt ccttttggaa   22200
gaattaagta atgaaccaat gctgttgttt taatgcccag acaaatgagc cagtgcgttt   22260
cttcctgtct ggttggaagc tgcaattatc cagctttcac aggaggaata tactgatttt   22320
gccgtattat ctggatttgc ggcttcaaga taacacattt ccctgcacat ttacagctgt   22380
gtaaagacac tcctagtgta cacactctac catttgtgga gcaaagacag cagtggagag   22440
tgctctgtga atgtggatgg ttaggcctgt ctttaccatg atgaggtgaa aagtcctgtc   22500
aggtgacttc acagccagaa gtagcaagca gcctgcttca tgagaattaa cgttgctcag   22560
tcgtgtgcaa ctcttttgcaa tcccatggac tgtagcttac cggctcctcc atccacggaa   22620 tttttcctggc aagagtactg aagtggcttt ccatttccta ctccagggga tcttcccgac   22680
ttggggatca aacctgggtc tcccaggttg caggcagatg ttttttcctc tgagccacca   22740
gggaagccag ccagattcat tgaaaattca actacttagc caaagatttc tggaatggaa   22800
gatagactga gcctgttgtc cttttgggc aggtgggatg ctggaactac gcaggtttcc   22860
catgggaaaa ttacttcttt gggacatcag accccaactc caggtgcaca aaagatgtc   22920 tccctgcagt ttcaaagttg tgtaaatgca tcctaggaca caatgtgcta tccttgaatg   22980
ttgactttca tatctgtttt tgcactgatc agctaaaact gtactgtcag aggacttccc   23040
atcaaaaagt ggtaagcagc atgtttcttc agaaaacaca agtacttgag gagccttgtg   23100
gtcctgatga agcaaaaaaa tgtccccgtg tgcttttcta tcaggctgga gattgcaagt   23160
atttcaggtt cgctaggtgc aaatgctgct ttcatttcag cccccaagtt ctaggttcag   23220
agaattgttt ccccacagct tcagagctgt gcaaagacac tcctaggaca gacacactgt   23280
atcatttcct tagaagagtt cagggaagtg tgttctgtaa gtgcttctgc cataccctttt   23340 tttaccctg agtgggcaga attacactgt ctggtgactt gttaacatta gtaagcaagc   23400
accttgcctt cagaaaacac agatacttaa gcagaactgt ggtcataagg aagaggcaaa   23460
tgaacccatg tgcatttctt tcaggcttaa gattgcaacc accctgcagt gacacgaagt   23520
gctgcttctg ccattaggct cagaacccta agtaaacata aacaaatgtc cctgtcctta   23580
gaaagctaat gttggtccag tggtttgtgt aagctttgta taggctgaga cttatgctga   23640 gttttgttt gttttttcctc tgatgggcaa ggctgagtga ttgggtttgt acttttgttt   23700
tgtttgttgt ttagatgagg agtcctgcac agggtgctac tggtggtctg gtgatgccag   23760
ggcttgtatt caagtggttt cctttgtgtg agttcacact atttgatact ctctaggatt   23820
agttctctgg ttgtctaggg tcttggagtt agtgctccca ctccaaacgc ttagggattg   23880
atctctctcc aaagaccagc ttaggtccaa actaccaaga ggaatttcac ttgaaatgaa   23940
agggccttta cttaccaag aggaatttca cttgaaatga aagggccttt actttaccaa   24000
gaggaattca ctcgaaatga aagggactta ctgaattcca aaagccagag cacaagaaca   24060
catggagatc tctacccaga ggaaactcta ccatgccttg gttgcagcag atgttggtcc   24120
```

-continued

| | | | | | |
|---|---|---|---|---|---|
| tcttctgctt | tgatctgtcc | ccgctttctg | tggcagctgc | ccagcagagg | ccatctgacg | 24180 |
| tcatttttgtt | cattacctgg | atgaaggggt | gtctccttct | cagaggagcc | tgagacaaac | 24240 |
| aaagggacag | tgcagagcca | tccccgcacg | gaagcccct | tccatttaga | aatgtttctc | 24300 |
| ttaagctatg | ttaatgaact | atgtatttag | cctagactct | gtgtttcttc | acttaggttc | 24360 |
| tgcctaagac | tcagaactga | taatggctca | acaaaccagt | atgttttct | catacaattg | 24420 |
| ttctcctaat | ctatgttaat | gagactatgt | atttgcttgg | aaacctgcct | tcttcaaaat | 24480 |
| tcatgtcaat | cattttatgg | cctgggatga | ctcaccttgt | tccaatgtta | cctcaaaatg | 24540 |
| catgttgtgg | gtgaggggcc | ctggtgccac | tctctgagtt | ttgagacatt | tcctttcttt | 24600 |
| aattagtacc | cttctgatag | gtgtataagt | taccattaaa | gtctagcagg | ggggcactc | 24660 |
| tttctgcccc | ttcaatgtc | tatgttagaa | gcttaatctc | ttttatactt | taataaaact | 24720 |
| ttatcacaca | aaagcttgga | gtgatcaagt | ctcataactg | gccccagatt | gaattcttct | 24780 |
| cctccaaagg | ccaataatcc | catcatcttt | catggctcag | caacaacctt | tcaccggggg | 24840 |
| agctcatctg | ggattcttca | ggacaaggta | aggacacttg | gagctctagt | tctttgttct | 24900 |
| cctggcaaac | acattttctg | ctgtacttta | ctaactctat | ggtgtgcttg | tgtgtgtgat | 24960 |
| tgaaagatgc | acacatgtgt | gaagcaagat | ctgggtccaa | atctttggtt | ctgtggtgac | 25020 |
| ctcataccac | ttatggcagg | aaccctgttg | ggggattata | ctgacctgct | aatgtcaaga | 25080 |
| ggcacccaat | gtctcctcca | gggaaacaga | ccaaggtgga | taaaacgtgt | ggatggaact | 25140 |
| ctccttttt | ggccaaactt | tctggtctct | ttgaccattt | cataacttcc | tgggaattag | 25200 |
| aactactaac | ctaatcagtg | ggatcataga | ctttcaaggg | acttgttatc | tatgctgtta | 25260 |
| ctgtgtattg | tcacttaggt | tccaaacttt | gttttgtttt | ttttgtatt | cacaaattgc | 25320 |
| ctagcctcac | taggagtcaa | tagtttggaa | gctagatgga | gttctaattc | caagaacatc | 25380 |
| tctcaggttt | aagattactc | aggaaataca | gcagtcttct | tcctttggta | acactagctc | 25440 |
| ttagtggacc | agaggaggat | ctccagttgc | ttctgtctca | acaccttaga | tattcttcct | 25500 |
| gtggaatctg | tgggaatgaa | ctggaaggac | tggccataat | aacttgagga | caaaatcac | 25560 |
| ttttcctca | gtggccagcc | cctcaccgtc | tcttttgcta | tcgcttatat | tggtgtggtg | 25620 |
| agactcagaa | ggaacatctt | ggttttatgt | ttgtcctta | tgatttactg | gtcttactgt | 25680 |
| ggtcaggaat | gtactcaggg | ttgtgcatag | gcactcagga | gacaaatatt | tcccttagtg | 25740 |
| gtcttagctt | gggaggcatt | ctggaaggtt | actctgactg | cacctcgggt | ggcatcagag | 25800 |
| gcaagcaaaa | gttttaatgg | tgaggaactg | ggtattagtc | tgggatgcca | tcaggtctac | 25860 |
| ccctgatgca | tctccacccc | accgcagtgg | tagaatgggg | aggggcagta | gtggaatacc | 25920 |
| tgtggtaaga | gacaggttaa | ctccagccag | ggaaggaagc | ttaggtggaa | gacctgtctc | 25980 |
| cacccccatc | tagaacaggg | agggacagta | gaaggacagt | gctggtagct | gttttttctct | 26040 |
| cttaaaggtg | ggagctaacc | attccagcct | cactcctttg | aaaaactggg | atagatttga | 26100 |
| tccccagagc | ctaatgaaga | catgcctgat | cttcctatgt | gatactacat | ggccacagta | 26160 |
| tccattggag | gatagcgaat | ggtggctggt | tgagggtct | cttaattaca | atattgtttt | 26220 |
| acaattaaac | tggttctgta | gataacaagg | aaatgggtag | aagtagcata | tgtgttgccc | 26280 |
| tttttctctc | tgtgagacat | atcagattta | tgtcctaagg | gtatatatta | gggtatgaaa | 26340 |
| ttttcagctc | cctattctgc | tatatgacct | tatttgggag | gatgtgatgt | atatcctggg | 26400 |
| acaggcgcta | actcctgcat | caacaacttg | agtttggaaa | gctgttgcct | atggagatga | 26460 |

```
atggcttggc aaggaatcat tagggaagag ggaggatgag atagctgccc tccccactgg   26520
ggatcaggca gtcccaacta tagaaccaga ttgggactaa aaggctaaag gatgatggga   26580
taagagtcat ttgtcagatg tgttcttgaa ggactcagac aagctcatgc taagacttta   26640
aatgatgcta atttggcaaa catagaacag gaagagaacg aagcttctgg taaattccta   26700
gatagactga gggaagccct ttgcagattc actgagattg atcctagtca gctccagata   26760
tccactaaaa cacatgtatg gaccaaatca gtctttagat aatctgttgc aattggctca   26820
gtcagtctat tatggcaggg agtatgaggg aagaaagaaa ggcagagaaa gaccaaggta   26880
ctggctgaag cccttgtaat ggctgtcagg actgttctta aacagcctga gaaaaattcc   26940
aggagagacc caggtgaaag gggatgggct tgctatttct gtggaaagga ggagcgcctc   27000
aagcgggatt gccctcaggc atctaagggg tccccagctc catgtttgcc tgtaaggggc   27060
cacactggag gagagactgc ccccagacgc gtaggtccca gtggtgggat tctcaagaca   27120
accaggactg aatgtgccca ggggtcccca cacaaactcc caccctaatt acagctgagg   27180
aaccccaggt attagtaact gtgggtggcc aatctgtcaa tttccttgtg gacaccaggg   27240
caagttactc tgtgcttact gaagcccctg gtccactttc tccccaatcc gcttctataa   27300
tgggactgtc tggacaagcc aaacattaat attttggtca tcctctaagc tgtcaactgg   27360
gactctgttt ttacagagtg ccagattgtg ccagagtctc cctcacccct tttagggagg   27420
gatatactga gcaaggtcca tgcctctgtt tcatgaatat ggagcccttc ctttctctcc   27480
ctttaattga acaaaatgta aatcctaaag tgtgagctga tggaaaatct gtgggtcgaa   27540
cacaaaatgc tattcctgta gttgtgaagc tcaaaaaccc actcatactt ccccatcaaa   27600
agcagtatcc actgaaaccc gaggttaaag aagggttaaa acccatcatc gagattttaa   27660
aggagcaggg gctattaatt ccctataaca gtccatgcaa cactcctatt tgggtataaa   27720
agaagtcaaa ttataagtgg agactagttc aagatttaca aataataaat gaggctgtac   27780
atcctttaca ccccatggtg cctaatcctt atactctatt gtataaaatt actgaacaag   27840
agaaatattt ttcagcatgc tttctagagt taaacctata ctatgtcatc ccctacctat   27900
gactttcaga caattgagag gatttggggg aatcataggc tactgcctca tttggattct   27960
gggttatggg gaacttgcct ggcctatata tgaacttaca actgaaactc aacaagccca   28020
aactgacaaa ctggttcagt ctctagatac tcaaaaggct tttaaagctc ttcagattgc   28080
tctcctgcca gctcctgctt taagcttgcc cacagggtca gaatttaatt tgtttgtcac   28140
tgaaagaaaa ggtatggtct tgggagtttt gacacaaccc cgagggcctc atcagctata   28200
tataggatac ctgaaaaact taaatcctgc cactttcctt cctgacaagg aaaatgaaac   28260
acctgatagc aattgttccc aatttctaac tttaaactat tcagctcggg aagacctgat   28320
ggatacccca ttagacaatc ctgatatgga attatttaca gatggcagtt cttttgttcg   28380
ggatgggaaa cttaaagcag gttacactat aatgcgactg gacagatttt aaaagcaaag   28440
tctctcccca gggaatgagc gctcaggtag tggagcttgt ggctctgacc cgagctctag   28500
agttaatcaa agggcagcaa gtcaatatct acagtgattc taagtatgct tatttgactt   28560
tacatgttca tgctgtgata cggaaagaaa gacagtttaa aacggcaaca ggagaaccta   28620
ttaagcattt caaaagactg agggactttt aactgctata aattgtccta cagaagtagc   28680
tgttgtgcac tgcaaaggac acagtaggga tgggaataag tagctgaggg taatcagctg   28740
gctgactgtc aagccagaaa accagcagtt taagaaaccc cttcactgca gatgcctttg   28800
aactagacag gtcctgtgga ataggaaaaa catcacaatg aggaagaatt agaaagatat   28860
```

```
gagaaagtag gagcaaacat tatcgataaa ggatgcttat agtccaagga tggatgatga   28920
ataattactg aaaattctca atggaaaatt cttaagagtt tacaccagag ttttcattta   28980
ggtgttgaga gcacttacca gatggcttct catttctttg aaggaaaaat gtaatggaaa   29040
ctttagagaa cattatcaaa aactgtgaga tttgtcagaa aaataaccca aagactgaaa   29100
agttagcaaa atctgggtta caatgaagtg gaaaatatcc tggagaggac tgggaaattg   29160
attttactca tatgccaaag gcaaatggat attcttgatt acaagtttgg gtggatatat   29220
ttactggaca gattgaggct tttccctgtc atagtgaaca gcctaagcag ttataagaa    29280 ttttaatcca tgaaattact cccaggcttg ggctgctgtg gagccttcag agtgacaatg   29340
gctttgcctt taaagccact gtaactcagg ggatgtcaaa agctctagga atagacgatc   29400
acttacacgg ctcctggaga ccccgatcct caggaaaggt tgaaaagct aatgacatta    29460 ttaagagaca tctgtgcaaa ttaactcaag agaggcatga cagttggtgt aaagttctac   29520
acatagcttt aatgagggct cgaattgccc cccaaaatga gggactgtcc ccctttgagt   29580
gcatttatgg aagacccttc ttacccacag acattgttat agaccttgaa gccttggaat   29640
tatctaactg tgtaactcag cactcagctt ttcaacaggc attaaaggaa ctctgatgtg   29700
actcatgacc cagactctaa gtcaagaaag acactgtctg agccaggaac tgaggtcctg   29760
ataaaaatat tgggatctcg ggggcaatcc ctggagcccc tctgggaagg cctttaccag   29820
gttattctat cttttcccat agctgtcaaa gtgccagata ttgatcattt tacaccacac   29880
ttaagagttg gcatcctgac cagaactaaa tgatgtcact ttatgtcttt attctctaca   29940
ctcttacttt gtacttttca gatcagcctg ataatctatg tgagcttgct tctgctgact   30000
ccaaaaatcc agtgtctgcc gtttgaccct caagacaatg ccctcctgtc ctgggatcac   30060
tcctatgctg catttcacat tcagtctaat tactgggtct gtggagcact cccttcttca   30120
tcagtggaag gcttccgtgg tgggcatctc cacttgaagg aaaggagttt cttcaagtct   30180
gcaaatcttt ctacaaagac aataatatgt gatgcctctt cttaatatga taacatctaa   30240
caatcctaag atggactggt gcaacacttt gtaccttaac tatgggcact atgagacttt   30300
taactttgct gattgttctg ttttgctgt ttgctccctg catctgtaag agtgtggctg    30360
gatttgtttc tagctgcatg aaggatttta agtgacaaat ggttgctcaa actcctgcca   30420
ctgtggcagc ttcctccaac tacctacttg ggcccctgg atcagagacc ctcaatatga    30480
gggttaggag agtatgttgc ctcaccaatt tagggacgat gccccttatc agcttggaag   30540
cagttacaga atgaaaacaa tgccccttc cctaggaaac ataattctcc taaagaaaa     30600 gggagaaata agacggtaac aggcaggaag gctcagttca gttcagttca gtcactcagt   30660
cgtgtctgac tctttgcgac cccatgaatt gcagcatgcc aggcctccct gtccaccacc   30720
aactcccaga gttcactcaa actcatgttc ttcgagtcgg tgatgccatc cagccatctc   30780
atcctctgtc gtccccttct cctcctgccc ccaatccctt ccagcatcag agtctttttcc  30840 aatgagtcaa cccttcacgt gaggtggcca aactattgga gtttcaactt cagcatcagt   30900
ccttccaatg aacacccagg accaatctcc tttagaatgg actggttgga tctccttgca   30960
gtccacagga ctctcaagag tcataggttg caaatgtcag acattttca tctctctctc    31020 aagtggcagg aggaaacaaa ctgcaagtgt cagatttctt ttcccttctc tatacaaaat   31080
taaaagatgc tttcttttaa aattctgtgt tgccatgaca cctggttcca cctgaactta   31140
acttttctca aatcttgagc caaccaatgc attttttta tggaaatgtt tttcttaagc    31200
```

```
tatgttaatg actatgtatt taaccoctag actccgtgtt tcttcaagtc ggtttcacct    31260
aagactcaga accgataatg actcaacaaa ccagtatgtt ttactcatac agttgttctc    31320
ttaatctatg ttaatgagac tgtgtatttg attggaaacc tgcctttctt catgccaatc    31380
gtcttatggc ccaggaagat tcaccttgtg ccaatgttat ctcaaaatgc atgttgtggc    31440
tgagtggcct gcagccactc tctgaatttt gatacatttc ctttctctaa ttagtagcct    31500
gctgatatgt atataactta ctgctgaaga ctagcagggg ggcactcttc ctgccccctt    31560
ctcttttcct ctggaggcca agaactctgg tgtctttcat tgctcagcaa caacctttca    31620
ataggaggat actgatattt ctccaagaaa agctatagtt ttgactatac agacctttgt    31680
tggcaaagtg atgtctctgc tttttaatat gctgtctagg tttgtcatag ctttcttccc    31740
aaggaacatc tttttttta atttaatgac tgcatttta atgttgttat gcttggtcc     31800 agctgttgca ttctttctga agctattagt aattaccctc tgctctttat cagtagctta    31860
ttcgacactt tctgacctga ggggctcatc ttccagtgtc atctattttt gccttttcat    31920
aacatttatg gggtttgggc agcaagaata ctggaggaaa ttcccatttc ctccttcagt    31980
ggaccatgtt ttcccagaat acttcaaatg acctgtccat ttttggtggc cctgcatggc    32040
atggctaata gcttaattga gttatgcgag acccattgcc gcgacagtgc tgtgatccat    32100
gaagagacag gaagctctta gaattacttt cttttttaatg cattctattt attccctca    32160 gctagattct aagtgtaatt tgtctgtta ttcattgata catttaacag atgtagaaga    32220
gttccttttg tttctaaaat attcaaaata tttctttata tataaaggat attcatgatt    32280
ttgtaataat tttcacaaac tgacataata attttactgt tcagttcagt tcagttcagt    32340
cgctcagtcg tgtccgactc tttgcgaccc catgaatcgc agcacgccag gcctccctgt    32400
ccatcaccaa ctgccggagt tcacccagac tcacatccat tgagtcagtg atgtcatcca    32460
gccatctcat cctctatcat cccttctcc tcctgccgcc aatccttccc agcatcagag     32520
tcttttacaa tcagtcaact cttctcatga ggtggccaaa gtattggagt ttcagcttta    32580
gcatcattcc ttccaaagaa atcccagggc tgatctcctt cagaatggac tggttggatc    32640
tccttgtagt ccaagggact ctcaagagtc ttctccaaca ccacagttca aaagcatcaa    32700
ttcttcggag ttcagctttc ttcacagtcc aactctcaca tccatacatg accactggaa    32760
aaaccatagc cttgactaga cggatctttg ttggcaaagt aatgtctcta cttttcaata    32820
tggtatctag gttggtcata acttttttact gtagactact ttttttttt tgagatggca    32880 agaatacaca gaagaactgt acaaaaaaga tcttcacgac ccagataatc atgatggtgt    32940
gatcactcac ctagagccag acatcctgga atgtgaagtc aagtgggcct tagaaagcat    33000
cactacgaac aaagctagtg gaggtgatgg aattccagtt gagctattcc aaatcctgaa    33060
agatgatgct gtgaaagtgc tgcactcaat atgccagcaa atttggaaaa ctcagcagtc    33120
ccacaggact ggaaaatgtc agttttcatt ccaatctcaa agaaaggcaa tgccaaagaa    33180
tgctcaaact accgcacaat tgcactcatc tcacacgcta gtaagtaatg ctcaaaattc    33240
tccaagccag gcttcagcaa tatgtgaact gtgaacttcc tgatgttcaa ggtggtttta    33300
gaaaaggcag aggaaccaga gatcaaattg ccaacatctg ctggatcatg gaaaaagcaa    33360
aagagttcca gaaaagcatc tatttctact ttattgacta tgccaaggcc tttgactgtg    33420
tggatcacaa taaactgtgg aaaattctga agagatggg aataccagac cacctgatct    33480
gcctcttgag aaatttatat gcaggtcagg aagcaacagt tagaactgga catgaacaa     33540 cagactggtt ccaaatagga aaaggagtat gtcaaggctg tatattgtca ccctgcttat    33600
```

```
ttaacttata tgcagagtac atcatgagaa acgctggact ggaagaaaca caagctggaa    33660
tcaagattgc caggagaaat atcaataacc tcagatattc agatgacacc accccttatgg   33720
cagaaagtga agaggaacta aaaagcctct tgaggaaagt gaaagtggag agtaaacaag    33780
ttggcttaaa gctcaacatt cagaaaacga agatcatggc atctggtccc accacttcat    33840
gggaaataga tggggaaaca gtggaaacag tgtcagactt tattttctg  ggctccaaaa    33900
tcactacaga tggtgactgc agccatgaag ttaaaagacg cttgctcctt ggatggaaag    33960
ttatgaccaa cctagatagc atattcaaaa cagagacgtt actttgccaa caaaagttcg    34020
tctagtcaag gctatggttt tcctgtggtc atgtatggat gtgagagttg gactgtgaag    34080
aaggctgagc gctgaagaat tgatgctttt gaactgtggt gttggagaag actcttgaga    34140
gtcccttgga ctacaaggag atccaaccag tccatcctga aggacatcag ccctgggatt    34200
tctttggaag gaatgatgct aaagctgaaa ctccagtact ttggccacct catgtgaaga    34260
gttgactcat tggaaaagac tctgatgctg ggagggattg ggggcaggag gagaagggga    34320
cgacagagga tgagatggct ggatggcatc actgacttga tggatgtgag tctgagtgaa    34380
ctccgggagt tggtgatgga cagggaggcc tggcgtgctg tgattcatgg ggtcgcaaag    34440
agtcggacgt gactgagaga ctgatctttt tttttgtaga ctacttttaa ttcaaagaaa    34500
tgtccgtcaa ttattttctt atgatcacct caactttgta tctatggtaa gcacagaaaa    34560
gttcaaaact ttacctcagc atttcctatt atatttcttc cttgtgtata agtcaataat    34620
atgtgattct agccaaatgc acaaactgtt cagtcatcaa agcacttact aggtgcctga    34680
tactgcagta ggcatgatgg gaagcaacat acatgcatca cagagggaca tgctaaatat    34740
tgttgatata cattaaagga atagttaggg aaaatatcga tataaggaa  atggtaaatc    34800
tgatggagtt tatagaggat tgtgtattgt caaatacaga tgtcaatttc tataagttta    34860
acatataaaa atggagaaca aagggctaca atgagaagat ataaacatta aaatcatcta    34920
gcaaatgtta tctcacaatt aaaaaatacc ttctgtgcac taaagcacta aacttatttt    34980
tcttaaagcc cttgaaatta aaggctataa accagttctt tcaagggta  aacaaaattg    35040
ataaacttta agccagactc atcaagaaaa aaaagagat  ggaaaagaac ccaatgaata    35100
aaatcagaat tgaaaaagga gaaggtacaa cagatataac agaaaccagt ggactatacc    35160
ccaatcaaat gaaaacccta gaagaaatgg acaaattctt agaaatatac aatctccaaa    35220
gactaaacca gtcagaaata gaaaatatga acagaccaat taccagtaat gaaattaatc    35280
agtaatttta acactcccca aaaaataaaa gtccaggaca agacggcttc acaggtgaat    35340
tctatcaatt taacaaacag ttagcaccta tatttctgaa accatttcaa aaaattacag    35400
tgagagaaac acttccaaac acaatctaaa tgccaccatc accttgatat aaaaatcaga    35460
aatatgccac aaaaacaaat aaaattacag tccagtaaca ctgatgacag agaaggcaat    35520
ggcaccccac tccagtactc ttgcctggaa atcccgtgg  atggaggagc ctggtaggct    35580
gtagtccatg gggtcgctaa gagtccgaca cgactgagcg acttcacctt cattttcac    35640
tttcctgcat tggagaagga acggcaacc  cactccagtg ttcttgcctg gagaatccca    35700
gggacggggg accctggtgg gctgctgtct atggggtcgc acaagtcgga cacgactgaa    35760
gtgacttagc agcagcaaca ctgatgaaca tatacacaga aaccaccaca aaatacttgc    35820
aaaccaaatc caacaataca ttaaaaacac cagacaccat ggtgaagtgg gatttatatt    35880
agggatgcaa ggattttta  atatctacaa atcaatcatt agaaaatttg aaaaatgaaa    35940
```

```
gcaacctgat tatctcaata ggtgagataa aaaaaaaagg ttttaaaaaa ttcaatcccc   36000
acttatgatt aaaaaaaaaa ccaataaaag gacatgtggg gaacctacct aaatatgata   36060
aggatcatat acaacaaact cacagcaaaa atcattctca atgctgaaaa ttaaaaggca   36120
tttcctctga gatcaggaaa aagacaatga tgttcattct caccattttt atttagcata   36180
gtttgggaaa ttctagtcat gggaatcaga gaaaaaatt aacaaaaga atgcaaatta    36240 aaaaagagta agtatggact ctgttgcaga gggagagggt gggaagattt gggagaatgg   36300
cattgaaaca tgtataatat catgtatgaa acgagttgcc agtccagatt cgatgcatga   36360
tactggatgc ttggggctag tgcactggga cgacccagag ggatggtatg gggagggagg   36420
agggaggagg gttcaggatg gggaacacat gtatacctgt ggcagattca ttttgatatt   36480
tggcaaaact aatacaattt gtaaagttta aagataaaaa aattaaaaaa agagtaagta   36540
aaacaatcac tgtttgtaga tgacatgata ctatacatgt gtgtgtacta ggtcacttca   36600
gttatgtttg actcttttg atcctatgga ctgtatccca acagtctccc ctgttcatgg    36660
gattctccaa gcaagaacac tggagtgggc tgctgaaacc ttctgcaagg gatggtcatg   36720
atctagggac tgaactcgcc tctcttacat ctcctgcatt ggcaggcagg ttctttacca   36780
ctagcgccac ctgggaagac aaatactata catacaaaat actaaagaca attccagaaa   36840
actaaaacag ctaatcaatg aattcagtga ggtttcagga tatggaatta atacacagat   36900
ttcccttgta ttctgataca tgaaaagtaa aagatccata aaaaattaag gtaacaattc   36960
cacttaccat catatcaaaa agaataaaac acctaggaat aaacttacct aatgaggcaa   37020
aagacctata ctcagaaaac gataagatac tgataaaaga aatcaaagat gatacagatg   37080
gagaaatata acaagttttt gagttggaag aatcaatgct gttaaaatga ctgtactacc   37140
caaagcaatc tacagattca atgccatccc tgtcaaatca ccagtgacat ttatcccaca   37200
attagaacaa aatattttt acactttgta ttgaaacaca aaagaaccca aagagccaca    37260
ccaatcttgt gagagaaaaa aaggagctga aggaatcaag cttcctgacg tcaaattatg   37320
ctacaaaaga agagtcatca aaactatatg atactggcac aaaaacagac atatagatca   37380
atgacacagg atgagacccc ataaataaac ccacattctt acggccaatt aacctatgac   37440
aaagaaggca agaatataca atgaagaaaa gacactattt gcaataagtt gtgctggaac   37500
aaattgacaa ctatatgcaa aagaaaaaat tagaatattc tctaacatca tgtataaaaa   37560
taaagtcaaa atgggtcaaa tacctaagta taaggctaga tacttgaaaa atcttagagt   37620
aaaacacagg tagaacataa attgcagcaa tatctatatt tagatatgta tcctggagaa   37680
atgaaaataa gaaaacagg caaacgggac caaatgaaac ttaaaatcat ttgcaaagca    37740
aaggaagcca taaacaaagt gaaaagacaa accagagaat gttagaaaat atttgtaaat   37800
caaatgattg ataagagatt aatttccaac atatacaaag ggcacatgta gctcaacaga   37860
aaacaaaaca acacaatcaa aaacagacta ttcagttcag ttcagttcag tcgctcagtc   37920
atgtctgact ctgcaacccc atgaaccaca gcacaccaga cttccctgtc catcaccaac   37980
tcccggagtt tacccaaact catgtccatt gagtcagtga tgccatccaa ccatctcatc   38040
ctctgttgtc cccttctcct cctgccctca atctttccca gcatcagggt cttttcaaat   38100
gagtcagccc ttccgcataa agtagccaaa gtattggagt ttcagcttca acatcagtcc   38160
ttccaatgaa cacccagaac tgatttcctt caggatggac tggttggatc tgcttgtagt   38220
ccaagggact ctcaagagtc ttctccaaca ccacagtgca aaagcatcaa ttctttggtg   38280
ctcagctttc tttatagtcc aactctcaca tccatacatg actactggaa aaaccatagc   38340
```

```
cttgactaga tggacctttg ttgacatagt aatacctctg cttttaata tgctgcctag   38400 gttggtcata actttccttc aagaagtaa gagtctttta atttcatggc tgcagtcaca   38460
tctgcagtga ttttggagcc caaagaaata aagtctctca ctgttttcat tgtttcccca   38520
tctatttgcc atgaagtgat aggaccggat gccatgatct tagttttctg aatgttgaac   38580
tttaagccaa ccttttcact ttcctctttc actttcatca agaggctctt tagttcttct   38640
tcattttctg ccataagggt ggtatcatct gcatatatga ggttactgat ttttctccca   38700
gcaatcttga ttccagcttg tgcttcttcc agcccagtga agaatagcaa ggagcgataa   38760
agccttcctc agtgatcaat gcaaagaaac acaggaaaac aatggaatgg gaaagactag   38820
agatctcttc aagaaaatta gagataccaa gggaacattt cagacaaaga tgggctcaat   38880
aaaggacaga atggtatgg gcctaacaga agcagaagat attaagaaaa ggtggtaaga   38940
atacatagaa gaactgtaca aaaagatct tcatgaccca gataatcacg gtggtgtgat   39000
cacccaccta gagccagaca tcctggaatg tgaagtcaag tgggccttag gaagcatcac   39060
taccaacaaa gctagtggag gtgaaggaat tccagttgag ctatttcaaa ttctaaaaga   39120
tgatgctgtg aaagtgctgc actcaatatg ccagcaaatt gggaaaactc agcagtggcc   39180
acaggactgg aaaaggtcag tttgcattcc aatcccaaag aaaggaaatg ccaagaatg    39240 ctcaaactac cacacgattg cactcatctc acacgctagt aaagtaatgc tcaaaattct   39300
ccaagccagg cttcagcaat atgtgaactg tgaacttcct gatgttcaag ctggttttag   39360
aaaaggcaga ggaaccagag atcaaattac caacatccgc tggatcatgg aaaaagcaag   39420
agagttccag aaaaacatcc atttctggtt tattgactat gccaaagcct ttgactgtgt   39480
ggatcacaat aaaactgtgga aaattctgaa agacatggga ataccagacc acctgatctg   39540
cctcttgaga aacctgtatg caggtcagga agcaacagtt agaactggac atggaacaac   39600
agactggttc caaataggaa aaggagtacg tcaaggctgt atattgtcac cctgcttatt   39660
taacttatat gcagagtaca tcatgagaaa tgctgggctg gaggaagcac aagctggaat   39720
caagattgcc gggagaaaata tcacctcaga tatgcagatg acaccactct tatggcagaa   39780
agtgaagagg aactaaagag cctcttgatg aaagtgaaag aggatatggc atcaccgact   39840
caacagacat gaggttgtgc aagctccgag agttggttat ggacagggaa gcctggcttg   39900
ctgctgtcca tggggttgca aagagttgac catgactgag cgactgaact gaactgatta   39960
attagtgata ttcagtatct ttacatatct ttagtggcca tctgtgtatc ttcttttgag   40020
gaatgtttat ttagatcatc agtccatttt tggcattgcc tttctttggg attggaatga   40080
aactgacctt ttccagtcct gtggccactg ctgagtttta caaatttgct ggcatattga   40140
gtgcagcact ttcacagcat catctttcag gatttggaat agctcaactg gaattccatc   40200
acctccacta gctttgttcg tagtgatgct ttctaaggcc cataaccaaa gctaaaacaa   40260
cactcaggtg ttgatgtgac tggtgatgga agtaaagtcc gatgctgtaa agaacaatgt   40320
tgcctaggaa cctggaattt taggtccatg aatcaaagta aattggaaat ggtcaaaaag   40380
aagatggcaa gaatgaacat caattatttt aggggtcagt gaactaaaat ggactgtaat   40440
gggtgaattt aactcagttg accattgtat ctacttactg tgggcaagaa tcccttagaa   40500
gaaatggagt agccctaata gtcaacaaaa gagtccaaaa tgcagttttt gggtacaatc   40560
tcaaaaacaa cagaatgacc tctctttgtt tccaaggtaa acattatcac agtaatccaa   40620
gtctatgccc caaccagtaa tgctgaagaa gctgatgttg aacggttcta tgaagaccat   40680
```

```
tatggagaac tgccccagga gccctgactc tccacgcttt gtgggtgctc ctatcggaga   40740
cagggcaagt tgagacatag ctagagaaag acctgaggca gagacaagag atgcaggcct   40800
tgaggtggga aggtgtcagt gttctggaag cctgcaacag gtgaactcaa gtgggccaag   40860
aaaatgcaag acgaggtctc aacagcatct gttccaagtc tattgagagg tacacaaaac   40920
aatctgagta agctgattca tgttattttc ctggatacgc aaacaatgtc ttagctcagg   40980
ctgctatgac aaagtaccac agactgagtg gcttaaagaa cacaaacatt tctcagtatt   41040
tatcatgctt tgaattctat ttgtgcaatg tttgagggga atgcagtgct tatcttttta   41100
ataggtacat taactgtgtc ttcgtttgga tgtaccaaag gatgagacaa tgggagatgt   41160
gagttggtgg atcgatgcct cagcttcccc ttcttgcagc tggatgatct gaggtgtatt   41220
cccattattt cacagatggt ccctgtggca tcaagctcca ctcacctacc atggtaatcg   41280
gcccactttt cctgactttg ctcccttcct tgtctcatgt tttctacttc ctcactttgc   41340
ttttctggag gctgggaaaa ataagatctt ggtattggtc aatccagtta ctggtgagga   41400
ctctcttcct ggtttgcaga cagctgcctt cttgctatgt tcttatttgg ctgagacagc   41460
aatcatctct catgtctctt ctcataatga cactgataca ggagatagat gggctccagt   41520
ttagacattt ataactggcc tcctgtttgc attttatggg gcagaaaaaa gtgggcttca   41580
ggctggacac ttacaactag ccttctcttt ggatttcctg acaaggata ggtgggctct    41640 gggtaaggca cttacaacca gccttctgtt tgctctccaa aatggaagta acaatagaaa   41700
cagagtaaat agccagattt tgtctcttgt caatatctta aaacaatagt cgtggcaaga   41760
acaaagaggg gtaaaatcct atttgagtaa aggattaaag gctctctgct cccctccttc   41820
ttgggacaag ggagacacta cacatgcaca gaaaggctac ttgggagaca aaagtcagag   41880
gaaatgccag gccataatga gtttcccctc ccaaatgctt tcaagtcagt tcattttggc   41940
tgaggggtgc atgaacacgt aaggggaggg tcctgagaca aattagctgg ggggacaaaa   42000
caagatgatt agcctgaggg aagaaaaaga cctggaaaac tccccccctta taaggatt    42060 aaacttccca aaggcatgac tcttctctga gcttccctgt gcatcttttc acatgtattt   42120
ttccaataaa attttactt ttctcattac cttctgcctc ctcacctgaa ttctttcttg    42180
acgagacagg catggactat cgacccaggc tctagccaac tggcctttgt ggtctaatgg   42240
ttaggactcc tgatctggga actaagatct tgctccctgc tactgctctc tgctgcttgc   42300
tgcaaggggt tgcttactga tgctagcatc tgaaatcaac actaagctca tccatgaggg   42360 ttctacccctc acgatctaat cattcccaaa ggtcccatct tcatactggg gataagggtt  42420
caatgagtaa atttgggagg gacacaaaca ttcagtccac agtacataaa gatgtcaatc   42480
ttgcacatat ttatttctaa atacaatgcc attccaataa aaattccaac tacaggtttc   42540
ttggaattca acagaattat ataattaacc tggacagaaa aactaagaat attagagaga   42600
ttctaaagca aagagaggat agtggttgat attagtccca ttaagtactg aggcatatga   42660
taaagctttt acccacttca tgtattagta tttatgtggg tttcctagag catgaggaaa   42720
caaacctctt cccatgtagc accccttcct ccagttgtaa caacttgaat tactctgatt   42780
aattgtggag ctatgtaaaa agaaagcagg tatatccacc aagtagggta gcagcttact   42840
gttcaccaat gtgacactgt gctttacaac agtcatccag aagatcacaa tacatttctc   42900
atatatattt agtcatctac tgctcttgat tcacagctcc caaaatctgc gggatttcct   42960
gagcaataag agcaagaaca atgtgagtat cttttgttat aatactgggt ctcttccctc   43020
agttcctaaa atcacttcag agccataaag gtgtcttgtt attaatgcaa gtccctttcc   43080
```

```
acaactactg aatttatgtt agtgtaatca cttttcagct tccctggtga ctcagttggc   43140
aaacaatctg cttgcaatgc aggagaccac ctgtaatgca ggagtcctgg gtttgttccc   43200
caggtcatat cccctggaga aggaaatgga aacccactcc agtattcttg cctgggaaat   43260
cccatagaca gagaagcctg gcaggctaca gtccataggg gtcacaaaga ggtggacact   43320
atttagcgac tgaaccacaa tcaccacaat gacttctgga aagcacctaa ggatgggtgg   43380
ctaattgcca gttgccaggg gggacaacct ggcagaattg acagatggaa cttaagttct   43440
agcccatgac ttttgggctg gggtgagata ctagaagttg aatcaattac caaccaccaa   43500
taatttaatc aatcaacttt atgtaatgaa tcctccataa aaccccaaa ggatggcttt    43560
ggagcatccc agttgtgagc atagagactc agtcacatgg acgactccac acggtccctc   43620
aatcccttgc tccatgcatc tcttcatctg actgtttctg aattacaact tttataata    43680
aaacaggatt gagctataga actcacaaaa atgtgttttt atgagttcta taggcagcat   43740
attaaaaagc agagacatca ctttgtcaac aaaggtccgt ctagtcaagg ctatggtttt   43800
tccagtggtc atgtatggat gtgagagttg gactataaag aaagctgagc accaaaaaat   43860
tgatgctttt gaactgtggt gttggagaag actcttgaga gtcccttgga ctgcaaggag   43920
atccaaccag tccatcctaa aggagatcag tcctgggtgt tcgttggaag gactgatgtt   43980
aaagctgaaa ctccaatact ttggccacct gatgtgagag ctgactcat tggaaaagac    44040
cctgatgctg ggaaagactg tgggcaagag gaaaagggga cgacagagga tgagatagtt   44100
ggatggtatc accgactcaa tggacatagg tttgggtgga ctccaggagt tggtgatgga   44160
cagggaggcc tggcatgctg cggttcatgg ggttgcaaag agtcagacat gactgagcga   44220
ctgaactgaa ctgaactgat gagccactct agcaagttaa tcacaggaaa ggaaggagtc   44280
attggaacct ccagtctata gcagatcagt cagaagcaca gatgacagcc tgaacttaca   44340
actggcatct gagtcaggaa gaggggctat cttatgagac taaatcctta acctgtagga   44400
tctgatacta tctctgggta gatagtgtca gaattgagtt gaattgtagg acttgcaata   44460
atgttggaaa attgctcgtg gcagggaaac caccaccact cctagacaca cacacacaca   44520
cacacacaca ttgggtttga gtgttagaat catttttaacc agtgataaga aagattacca   44580
atggtgcagg aactgccagt ggaaacacaa agtctcctga ccaaaacaga gcaaatcaga   44640
agccaaacct gggttgagaa acaaagaaat gatgacaaaa atcagacagt ttgtttcgaa   44700
aatctgggac caggaagaaa ttaagtgaag agcccaagtg tggcaaaggt tcagggtgac   44760
actaaacttt gttttgcata cctgggaact tcacacatgg ctagacagaa agagaaaagg   44820
acaaattctg tgggaaccaa gggggaaata ggcacagcaa gacgaggaca tgggataggt   44880
aaccacactc gggacattgt ttaactgatt cttctggtag actctcattt gcaaggtcct   44940
gaggctctcc tcccaagcaa tttataacct agttaaatac ggacagaaca gcttaaaatg   45000
gtgctggatg ataccagcca gttgctgctg gagcaggagg aagacagttg agttttgttg   45060
gggaaatatg gacagcttca cagaagagag gggtgtgaag gaattcgggg tgaggaaact   45120
gcttgagcag agcttcagcc aaggcaatta agaaggagc aactggcctc gcaggactga    45180
agcccagcgg ggattcaggg agaaaggttg tcagaaacat ggtctgggct ttttcacaca   45240
atctgaaccc cagactctgg agtctagcca ctaaggaatc atttttatgtg tttaaagaat  45300
ggagagatat agccgcctgt aatacatctg caccatgatg gtttctcttt aaattcacaa   45360
tcattcatcc ttagaaaaaa tgtaatttct gatgcaatag cttaaattgc tgaactgaga   45420
```

```
aagtcagagg ggagaaaggg ggaggaatga ggtctttgag gacatgaata ccctcaatga    45480
atgggcccat cctaaagagg accctcatta ttagagaaag tttaaaatac tctccattac    45540
acccatactc tcctccagct aatacctatt tctctgttcc tcccaggaca aaacttctca    45600
gaagaattgt ctctactccc tcaccttcca tttcttcatc aatttactct gtctgttctt    45660
atcactctct tgaaactaat cccatcaagg cccagtaac gacctccacg tcaccaaatc     45720
cagtgagttc tttcccacct ccattctatt tgtctctct atagctgact cctgccttct     45780
tgaaaggcac ctcctctctc acactcttga tatcctccta cttcactggc tgtcactttt    45840
cagtctgtct tgctatcttc tctttctcta attcaaagtg tgactcagca gatcagcaac    45900
atctaggaac ccaggagaaa tgcagattct tggacttcat ctcagaatta ctaaatcaga    45960
atctctaagg tgggcccaac cagtccatcc taaaggagat cagtcctggg tgttcattgg    46020
aaggactgat gttgaagctg aaactccaat actttggcca cctgacgtga agagctgact    46080
cattggaaaa gaccctgatg ctgggaaaga ttgagggcag gaggagaagg ggacgactga    46140
ggataagatg gttggatggc atccgact caatgggtaa actccaggag ttggtgatgg      46200
acagggaggc ctggggtgct gcagtccatg gggtcgcaga gtcggacacg actgagcgac    46260
tgaactgaat tgaactgagg gtgggcccag gaatctgtgt tttatccaga ccccaggtga    46320
tgcacactga aagctaagca ccatgatcta aaactgtctg tttcttacca ttcagtcctg    46380
attcctcttc tttcctctgg ctacactttc tttcttgatg ttatcatcta agcccacaac    46440
tttgaaaatc atctaaatac tggtggtggt ttagtcacct cagtccaact ctttgcaacc    46500
ccagacccct ctgtccatgg gatttcccag gcaagaatac tggttgccat tcctttcc     46560 aggggatctt cccgaccaag ggatcaaacc cgggtctact gtaatgcagg cagattctta    46620
ctgacaattt ctaaatgcac atcttcagca ccaaccctcc caatctggag attacattaa    46680
aattcaacat accccaaatg gaagaaactt ctctaaaaat ggttgcgtct aaaacttggt    46740
cttcctccat ttctcaccat ttccgaatac atcctctacc accaagcccc atcagtgccc    46800
ctcaggcccc acacaacaat cagaatggtc tttgaaatca ggtcaggtca ccaccctgct    46860
taaatcttca agggcttcct atcacattta attaaaatct aaagacctgg tcattggctg    46920
ttaggcccta catgacctgg tcactttcta tgtggcttcc tgtattccct tgttgtcta    46980 atgtcagaaa ctataactat ctagttcaca ctaggttctc tataaattat ttgctgaaca    47040
aaatatttct tcttttgaaa ataagagaaa catagagttt acttcgttag cttctccaca    47100
tttgctgagg aggatctatg tgatgttgac aggtaacttc aattgagcca ggacacagga    47160
gatgcgaagg gagactttca agaatgtct tcatggtgcc ataacctcag cacagccagg     47220
ttccagagga caaaccccca aacatgcttg tcattcagtt cagaatgtag ccttcctat     47280 atataatggg atatagtagt tgtggtgatg gtagagacta agatgaggaa tgatgtaggg    47340
ccatttgcaa aaggtttctc ctgtgggctg accaacgtga tgttgttcat gaggccagtg    47400
aaagccccta agaatctaca accccataat ggcagttttc aaaaatggcc agaaattctt    47460
tgatactctt cccattgaga gatggggtcc atgattcctg cccttgaatc tgcatgggca    47520
tatggctact ttggtcaata gcatatagtg aaagtgatgt tatgtgatat tatgtgactt    47580
ttgagactat gtgagaagcg gcaatgcagc ttccatgttg tttactgaca gtctcacact    47640
tgggtcctct tgggacttct taagccaggt aagaagctca tcaaacttga gactactatg    47700
ctgggaggaa gccaggccac gtggggaagt cacgtgaagg cacttcaatc agtacacctg    47760
attttcaagt cctcccagcc caggtgccag ccatgtaagt gactgaacta attccaactc    47820
```

```
ctagctatca cgtcaagcct cagacgtcat ggggcagagt caagtcccca ttgtgcctgt   47880
ccaactcttt ggcctacaca attcatgggc ataataaaat ggtggtttct ttaaaccatt   47940
aagttttgga gtagttgcta catggcaaca atagccagaa taggacaaaa ggtaatgtca   48000
tttcgttccc tcaaaccctc acgaactata ttgccttttg agcatttcct tggttggggg   48060
agggaaggaa atcattcagc cagttgacat tggattcttt tgaggaaaaa aggctgagtt   48120
ttggcatcct ctaaggagc tgtacattgc cctcctagc aggggaaagt cagtcccttg      48180
cccagcctga tctgatcact cactcccagc tccacccagc tcaagactca aagagatgct   48240
tcactgcccc caatgtgcct cacaataaac aatctctgag gaaagaaggt aaggctctaa   48300
aagtagtgtc aacttaatca ttatgtaaga ctgactggat agaaaacagc cctggcattg   48360
ctgcctaata ctcatttcta gctggccaca atccatttct gctactgaat catcatcatc   48420
ccatcgtcat gttttataga cctctcattt ctccttccca gcagaacttt caggccccca   48480
tccacattca tatattcatc acctcattct acacaattct cctggcctct ccctccctc    48540 acttgtcccc atcctatttg agagatccac cctgagatat ttaccctaat gggtgtctca   48600
atatttttaa acctctttcc ttgcaagctt agtggagcct cttgcccata acaagggac    48660 tagatatttc attttcccca ggtttatacc cattgccctg cataattaa tattggtact     48720 ctcaaaagtg cacaaatttg ggtaatgata tatatgatcc ctctaaccct aaaacatgtc   48780
ttctatcact tgccatcctt cacatgagac aaacacctac ataaaatttt ggcagtaata   48840
atgatcaagt acacaccatg ttttatacaa gaaacctcag gtaatgtgca gaatggactt   48900
gttaaatgga gtgcatttcc ttcacttatg aatatcataa tctaaatcat ttattttgta   48960
gataatgagc aggaactgag taatgacgg caggtgatgg ctaatatact ttctaggcct     49020
caaattttaa tctgaaaatt cacaaacatt gggctcaatc cagggcaata gaattttgt     49080 cccttttaga aatttctggt taccaaagtt ccagaaattg ctttctcatt ccctaatctt   49140 tcatttctc cattacgtaa cgagaagctg gggctttggc cgattttccc tttaaagatg     49200
atttttatcg tcaacaagca atttcaggga gtgatgagcc ggggaagcgg tattagctga   49260
tgctagcgtt taagctagtc tcaactcgtt tttcccaggg acttagattc ctgggtctgc   49320
cagtaaaccc cggcgccgg cagctggtgc gcctgagcgt gcgcgcgcgc gccgtcgcct    49380
ccccgcccct gccccctcctc ctccgcccgg cgactcaccc gccctagttg ccagtcgctg   49440
acagccgcag agctgagagc gtcttctctc tcgcagaagc aggtaaatag ccgcgtagtc   49500
ctttaaactc ccagcggagg acgcccaacc ctgggtcttg cggccgaggc cccagggcac   49560
ccagccgaat cggattggtg ggaggcagac cttgaccgtg agtagggctg ggggcttgcg   49620
gcgggcgcgg ggaacgtcgg gcctgttgag cgtgctcgtt ggttttttgcc agccgccgct   49680 cggttttacc ctcctggtta ggagagctcc atttactcgg aatgtgggct ggctggtccc   49740
cctcccgagg tatgtgggtg gtgtgtagga atctagcccc ctcccacgct cgtccactgc   49800
gggagtggga tgggcgaatc gcaccggtag aggagccgca ggtccgagga accgctgggg   49860
agctcagaag aacaagggcg aggccccggg atttgggccc tcccgaagcc cagaggagtc   49920
gcggaattgg gggtgggggt ggtggggaag aaacggcgc ccaacggggc ccgacctcgg    49980
cggtgaggag tgccggagcg tccgtgggcc cccagccgct gctgccgaac tcctcccgag   50040
aggcggccct gcctgccatc acgcggctgg gaggtacctg ggtagccgca gcgggtgggt   50100
ctctggcaac ccccgggga tcggctctgg cgggcgtgcg tggcctgggc ttcagcctcg     50160
```

```
gcgcggggaa tcatgggcca cctggcgctc tctccgggcc agagaaatcc aggtaccggg    50220
aacagtgttt cctgggagct ctgatgtggt ggacccaaaa gcaaagcgaa attttccctg    50280
tctcgactga tcctccggaa ggagggagct cggccgtcgg gagactgagg ggaggggatc    50340
aggcgcctct cggagaacca ccctcatctg ccagtgaggg tggcaccttc acgcttgatt    50400
tttttttttc cccttcaca cgtttgatta ttaaacaacg agaagtccgt tttttgctgt    50460
cctttttccg tttttttttt ttttttttc cttttggtac catatgtagc aaatagattt    50520
ttttaaaatc ataagcccac caccctcacc atcttttttt cagtttcctc gtctccagat    50580
tcttaacaac aaagcagttt cacctccctg atcatggtta tccttatctc atggccgggt    50640
tattttcttg tacttaagag caatcacgtt ttattaagca gttccccgaa tgctgaacct    50700
ttgaagtgtt acctttcctt acaaaagata ccacatagaa taggattaaa aattttcaca    50760
agttgtcaga gaaaatagg aacagaaaat tgtataaaaa tgtcagacct ctggaaaatg    50820
aacagctctc tcagatttga aaattaacct atgaaaagga acagttttcc tacgaaaaca    50880
ttgaggtgct ctaacaatga aaagaatca gaaaaggaaa aaacagagt taggatgtga    50940 tttgtatatg atttgtatct gatgcaaatt tttcatactt gtgaaagaaa aatatcaaga    51000
ttataaaaag ataaatggtg aaatgaacaa tcatttatga aataaaatac aaatcaaagc    51060
aagtctggat ttacaactac tagtaaaaac aacagtaaca gcaaccactt ctggaaagtt    51120
acctagaaat ttgcatattc agtatgtgag gtggcaaggc tttggagtta gaaatatggc    51180
tctgcaacta attttacagt ttgggaccta atttcctcat ccccttttg gacattcata    51240 aaatagagga aattatacct acttcaggag tttgccaaga ttaactgtgt aaaactgacc    51300
tttagtgtgt atacttttat tcttttccta gtcacactgc actgggggac gttgtgaatc    51360
tgtatgaaat ttgtgaaaaa cagtcaggtg atccttaag ccatgaccct aaaacccac    51420 tcctgggaac ttacctgtaa tggaggaaac caggaaagaa gaagaaagc tgcattcacc    51480 cacagaactc agaatgatct aaaattagat ccagtccgga gacaacctaa atgtattaat    51540
aaaatagcag ggcagcagct aagaaaatca tagcacttta actgaaagga acattgtgta    51600
accatcacga gtcataattt tagagcctct ctgtgatata caggaaaaaa ctgacaggtc    51660
aaagtaagat tactcagaca tggatgcgtt tgtggaaaat ctgaatgaaa aatgaatcca    51720
cagtttgctg tgtatgggag gagagttcag tgtcacgttt gctgcttttt ttaagttagc    51780
atcatctctt ttttaaaaat actatcatat ttttccctg agtagattca ttagtggttt    51840
aataatttat atactgttat tctgttaaat aatccgttct tagatttatc aatttatagtt    51900 ttttctttt tttttaagga cttctgaata tatttgaaaa ctgaacagtt tcaaccaagc    51960
cgaagcatct gtcttcccag agacacaaat ccaacttgag ctgaatcaca gcagatgtag    52020
gtaccctgca gaatctcttt ggtcttgtga tggttgaaag tgcccaactg tttcacagaa    52080
gataagggac tgaaaggctg ggatcacaaa tccttgctgt ggaggccact gaaatctata    52140
tatgtaaccc acacctatta tatcactctt tcttgtaaaa gcgtcttgat tttgcaggga    52200
aagggacata gctttctctg gaatcattct gagttatgta agaagcagcc atttaaaaaa    52260
tagtataata aaagcaatta cctaacattt ctgcaccaaa tcaacactga aggtgactat    52320
caacagacaa aaggtttatg aggtaatggt ttttctaagc tttagtttta atttacctat    52380
tccattctcc cttttagat cttatttcct tttccaaggc agccagttta tcaactgtga    52440
actgctgcat atgaagcatt caaaacctga ctgtgtctaa agctgtgatg gctacagcac    52500
aatcatcttt gagtgaatag tatgtttaac agttcttaca gttgggagaa tttttttctca    52560
```

```
gtttgttcat ccttttttctc ctaaccgtgt tctgcttatt gctgttctaa tattgtgtga    52620
tcatgtcaag ggaggtgttc ccttttatgc aaaacattat gttaaatgtt gtcttcccga    52680
gaccaagctc ggaagattgg ctaggagtgc agttccgtgg gaagccttat tataggttcc    52740
taaatctcat cactagatac tcccaggctg ttggcctgat gcagactcta gctatgttgc    52800
ttttcttaaa gctcttcaca tcactctgag gatggactag actggggacc gtttgcccat    52860
ttcagtccag ggctaggcct cagtgtcagt agaaaaacct ccacctcaaa atggtttgta    52920 aattttttgta tagtttgcat tagactcttg ttaagggaca gtgacctcaa aagatgaaaa    52980
tatgacaaat gagttccact tagcttatga aaaattggaa atttccccag ggcaaggatg    53040
ggtagaggga ctgtttggtg ccagtttcca atttaaataa gtctcaaggg tataacatat    53100
tttgagtatc aaaagtgtgg cccctggcac atgaccactg gacataagtt cctaccagct    53160
ctgattctca atccccatgt ataaaaggga ataagatgaa tgggacaata tatggatttt    53220
gttgttgttg ttccttctct ctcgttccat cgctctgcct ttgtgcttat gcactaatgc    53280
cacgagattg tatttattat agttttccaa tccattctga tacttgccag gccaagtata    53340
ccttagatgt tcttcctgtt cagtaatttc ttcagtcttc ttaattttga gtatcattat    53400
attctttaaa atcctctttg agttaggact gaaattgtat tgacttaatg attaattgga    53460
gttgaattgg tatctttcaa aatcttcgat cttgattttc ccaaccataa accttgcctg    53520
tcttctcttt ctttccagtc ttccagcttt tttcatctaa gttctactat ttattattag    53580
gttaaatctt agtttgaatt ttttgttgcc attaatgagt ggaattttt tttcacacta    53640 aatcttctaa taattacaac taattggagt attcactctt ttctatatgt tgagttcaaa    53700
aactgccacc ctaataaata agctcattga tttatttgag ggcattttta aatgattgtc    53760
ctggattttc cagatagaaa aatcatacct ggctttctcc atagcagtct aaaatgcagc    53820
aatcacttac attcttgtct tgttaatctc attcacgaga atgcttttcc tctttctgtt    53880
aagatagggt gtggaatatg tattacttct agttctatag aaattttttc aacatcttaa    53940
acttaaaaag tcaggaaagc actgattcct gagtttaagt gagaactttg attttaattg    54000
aaaactttgc aacatcagag aatctttttt ttttctcctt agcctactaa taggttaatt    54060
gatttcatga ttttgagcca ttcttgtatt cctaaaataa tccttattgt cacagtgtat    54120
tctttcacta aaatatcaaa atcaacttgg tggtattttc ttttggattt tggcacccat    54180
attgctaaag gttgggtagc taagagtgtg agcccttcac tccctgtggc tcttaatact    54240
acatctcagg tgaactgccc aaatgtttat ctctactgag taagagttcg agattcttat    54300
aacaattgcc taaattgata ctctcacttg aatggctcat agatatagca aagttaatat    54360
atccaaacta tagctttatt ttttctcaca agcctggccc tccattagtt ttcttgtttg    54420
cattaggtgg catcaccacc atctacctag ttccaaaagc cacaaacctg ctcaactctc    54480
actctcccat ccactctatc agcgtaatcg tttttttcta caaatactt cccatttttc    54540 acagctccgt gctgctttgt cacagttcca ggttacacca ccatcttcct ttaatcattt    54600
tctaagtggt ctcaccattt cctttcttat ccctcaaatt tttctcttta acacagcagt    54660
aagggtgaac tttaaaaaaa aaaaatctgt gatgtgattc tcctaagcca ctttaatggc    54720
tttgcactgt ttcaggctcc agacacgtat ctccctgtag tcctcaaacc cacaaactaa    54780
atatcttacc actgtgtcct cagccacaga acagtaatat tagaggacat gtaataaata    54840
tttgttaagt aatcaatagt tattgtacat tgtacattgt acatactagc tgttccataa    54900
```

-continued

```
atatttattt aatttaaata tttatttaat tgaatgaatt caatatcagt ttttataatt    54960
gaatagaaaa gtaatccctc ccacacagat ttttctttct tttttttttt ttttttttat    55020
gaagcaagga atatgactac ttagaaagct ggctgccaga gaaaatggca gactaatgtc    55080
ttaaaacaaa tatcagtgtc tagatgccag gttcttttat agaacagaga tggcaggaag    55140
atgaggaaat aaaggcagaa tagagaggga gaagtggggt ggaagtaaag taaaaaaggc    55200
cacgtcctgc aagacatctc cagaaaggcc agcctgtgga agggatgtgt taatctcttc    55260
ttgcctgcaa ccattcacag gtgggaagtg tcaaattatc tccctgtgag ctgaacaaag    55320
gcacttcagt ccaacagtta gagagaggga ctgggttttc tgaggcaggc tattatatat    55380
gattgtaaca acaacagcaa caaaaagcaa gtcaaagaaa cagttccaat atggagtcag    55440
aattggttct tctcagcaac agttccccac tgtcaaggtc catttgacaa tcttgtagga    55500
aaagggggaca gtgatctttc tgtttgtcag atgaatcttt ctgggagtgt ctgcctttga    55560
tgccagtgtt ccaaatagtg agatttgttt tcttttttgtt cctccttgga aagtgtctac    55620
tttatacttg tcaacttaga aatattggac ttcaaaccca ggagggtttc tcaagttaag    55680
aaattttgca ctttctgtg tatgggaaga tgcaagcgtc agggttcatt aaaattattt    55740
ccttgatgtg taattcagct gtctggggcc tgtgatcctg tattctcaag agtttcctca    55800
aggttcacca tagggagtgg gtgcaatctg atgactgctg gatggcatgt attctccttc    55860
ctgagttttc tccttcctga gttgacttgg ggttcaccag ctcacattag agggcttcaa    55920
ttgttaattc catttctcag gtcttcccctt ggtcaggaat ttgaccaata tttgggagac    55980
atttcatggt caaactttgc ttcacggtgc tgtgaggttc atcccaaatc aggcaaaact    56040
tcttgatgta ccactctagg tgctaaattt tggattagac ccccatgaat aattaaagat    56100
tctctggatt ctaattgtca tccaggagac atttttccatt gttgcttctt cccataccta    56160
gaatcacact attataatta ttttatgtta taaatgtgat ctattttctc aagatgttta    56220
tccgtagaag ttttgttgga ggcctgatta cacattggtt actgcaagag acaactatct    56280
tataaattag tcaggatata agtaatgcag ctagtaacac tgataatgac atagtgcaac    56340
aggggtgtgc aaagcacaat ctaaaaacaa agaataaagt aaagcaatga ttagtataac    56400
tagttgtagt ccagttgcaa taatctagtg accaaaggag ccataactga tttaatgatc    56460
tatcttcagt ttcattgtac cagccatgcc atagcttaat ctttgagaca agcatatgct    56520
actggcagga tcaaccagat agaagaagat ttaagttta cttttgctta caaaggatat    56580
aatttaccaa gttactgtaa gtcagaggtt aaggaagttt tccttacacc tgaaaaacag    56640
atttaaaccca gttatttta gatagaaacc ataaaaatta taacaagttc agttcactca    56700
gtcctatgta actaatcctt tttgttaaca gctttatgaa gccatcaggt ttcccattag    56760
aattcttcaa tgtgttacta gttcagcatt atggtctaaa agtcagaaac ttggatttat    56820
ctgaaagtcc ttttataaa tcttcttaaa gaggagacat ttttacagag caacagagt    56880
gagaccataa ctgtccataa tgaccaaaga cttaagaagg cactttaaat ctgattatga    56940
tgcaattgac aaagtaaacct ggttactgct gtgacataca acagtttcag gtagtagaag    57000
tagaatcatg actgataata ttctaccagg acatatcaca ttttttaggaa ctccatataa    57060
tctctagtat atcagtatca tttatcatat aattttaagat atattattca ttggacaaca    57120
cttgccatgt agtttaacat accaagtgaa tctaattagt ttaatatctc cctttggtgt    57180
gtctcagggg ccctttgaag cacccccaaag ttagctaaag atcaaaggaa ctttattgta    57240
acttgatttg ggaagtcttg tcaaaagagc attaagaaaa aatgtttttaa aacacaacag    57300
```

```
gatcataggt cactgtgaaa caatagttat ttacttagcc aaaatgacaa taaaagattt    57360
caaaagcaaa tatagaacag attatttaaa aggtagaaat aatctgttat caaggagag     57420 gaaagccaaa tttgttttgt accaggttac tttcaagatt catttagtca attaaaattt    57480
tttaaactta gtcctgatca tgtacaaaac acttttttcag ggtccatgtt tcacgaattt   57540
tccatcactt aatttatttt agcacaattt taactttcaa gttgttgaat atctggagat    57600
atcctaaaat ataattattt ctgaaagttc actctaagct cttatcttca tttgcatttt    57660
ctttgcttaa cagtttattc acatcaagtc cctttccttg ctgacaaatt gtatcaacaa    57720
acaaccataa ataccaaata taatttaata ttaaatattt cccagttcac gtgaacctgg    57780
agctcattta gcttaattgt atttagaatt gtttggtttg taagcactta cttttattta    57840
aaccaattaa atagagctct tttacaaatc aactgcagca atattatcca aagacaaaga    57900
tacatacaaa cacacaaaca gagaggcctc agttcttatt tcaagatttc agtcctgagt    57960
caggcaatgt aaaacccatc agtttacata cgaggttgaa ttaaaattgg atttctcata    58020
gatggaataa gtcaagctca cttggctaga tagctaaata tttgcagaaa aagcacttag    58080
gaattctaat tatcttggcc aacccaactt ctaaattact ttaccttctc taaaatttgc    58140
atttaaaaaa gacagcataa tgagggttcc tgagaggaca tttgcatctc aaagacattt    58200
gcatctcaga gttacaggca agttttttcca aaaatgactt tgtttctcct ttaatactta   58260
caggcctctt aagataacca gggaaggtct ggggagtagt aaaaggattt atgggatttg    58320
gattattttt ggaaccacac ttctggtgct gtaaagacta catttgtaaa acacagtttt    58380 gttttttcttt tttgagtgat actgaaggat tgacataccc atttacctat gttggaaagt   58440
tttatctttc ctcatttagc ttagctcttg ggaagacaca gaggcaacaa tttaggctcc    58500
tgtaaatcag tctggactga gggggggaacg aggtgaagat aagaaagaca ggctgaggaa   58560
tccgcctcat agtcctacca ggaagatagt ggccagggcg aatgggtcag tgttttgctt    58620
gaaccaatgt gtgcttcaca gtgcacagaa gctgtcttgc tggagttgtt gtagccacaa    58680
gttccggcaa acaaactcac tcagaaggac aatgcagata gtggagtgca gtttattaca    58740
cctgcgggcc caaggcagag tctcctctta gccaaggacc ccgaccagtt tttgtgaaaa    58800
ccttatatat cctaagtgta tgtgcccaaa ccccacctccc cgaattccct gaaactagtc   58860
tgaacaaagg aaaagaaaga tacaatcaaa gttaacctgt gattcatatg ccttaagcct    58920
aggtagttaa cagtggacag ttatcaatag gcctgtggtc ataccccaat aagcataata    58980
gaatttatga ttctattcgg ttacacagat aattagggta ttctttttagg ctactgagag   59040 tctaggtatg agccctgggg ctcttgcggg ggggggggg ggtctggttt tccagttagt     59100
atgtcatttc catagatact gggcatatag ctcaaagtcc acagtccagc ccaacatgga    59160
gtcctgcttt caagatggag cctgttctgt ctgtttcttc gttcagagtc agatgctcta    59220
atagcctggt ccattctgtt acccacttag cctgtcacaa gagacttcaa gcgacaggca    59280
ccttaatggc ttttaagtgc ctgacccatg ccctcaaaat attaattggc ctggtactca    59340
gcctaaggga gaaggaggta aggagagccc tgacctgttg ggaggcagct accggggcac    59400
agagggctat taggccttta gaacacccca gagaataacc ctagctagag ttccatagct    59460
attagtctgt ttgcagaggg tttaaggaga aagggatgag ggagtgtgag gagagtggag    59520 acctttaaagg aagtacttct ccttttttagct caagcaatta gtatcagatg tctatatgtt  59580
accaaagtat ccggaataaa ccaaaatcta gccagctaga gagtcacatt aacatgactt    59640
```

```
cccagtttca ttagacctgt gacctttgtc caaaatgctt tataaatgga gttttccttc  59700 acagggtgc ttcccaagct gaagctgaag ctctccactg tcaaagttac ccagggctcc  59760
cgtagggaaa ttagaatcag atgcctcaag tccaagggag tccccaggcc tcttcactta  59820
tatcagagtg ttcctctcct tgcaaaaca cttctaattg caagagtgtg taattgtgag  59880
ccatttaggc ccattgctct tctgatctta acatatctaa tatatgtccc ccaaagcttt  59940
tcttcaggat agatgaaata tttcccattt ttataagttt catagcacca aaacacacac  60000
aaaaataggc aaattccaac ataaatgaca caaattccag taccaataca tagatgaacc  60060
agtttccagc tcaggtaaat aaatttaccc tacaaaacaa atgaactaat cccaactgtg  60120
tgcttgttct gtgcccttcc tctggacgca tgcttgctaa gccgcttcag ttgtgtctga  60180
ctctttgcag ctgtttggac tgtgtcccac catgctcctc tgtccatggc attctccagg  60240
caagaatact gccatgccct tggatagact ccagtattct tttactccag tatactcatt  60300
attcttgcct ggagaatccc atggtcagag gagactgaca ggctacagtt catgaggtca  60360
cgaagagtag gacacgactg aaatgacata gcacaaaaca agcacacaag aactagttcc  60420
ccaataaact ggttccaact caggtagaat ccaacaacaa ttcccatctc caacagggta  60480
ccccaaccaa attgactagt cctgtaaagg aaaagcccaa atttagaggg gaatatgttc  60540
tcagtgtgca caccagagca acttacccta caaaatcaag tttgtcaact cgtaatagaa  60600
aagggcacac aaaaccacaa acaaatgagc cagctatcga atgaagaaaa ctaatgctat  60660
gaaattgggt ctgtcaactt gtagaagttt gttgattctt tgcttcaact gccaggccct  60720
agggccactg ataccacttc agggaatctt gaaggagaga tcctcagcac aaatggtccc  60780
agcagctgct ggagccttgc cctaatattc cctaacagag ctggctaaac acaaacagca  60840
agtcaaattt gttaccgaat ccaggcttgc tctactgagt gaacaacagg ccagtgaatc  60900
agagatgaga tgttgaggga aagaatgtga ttttattcag taagctggct gaccgagaag  60960
atggcagact aacatctcaa aataaccatc ttcttgggtt ctggagtgcc aggttcttta  61020
tagaacagaa atgaggggaa gtgaggaaat aaaggaaaaa ggcagaatag agagggagag  61080
gcaatgagtc ttgggccatc agtcttgcaa aacatctcta ggaatcccca cacagttttt  61140
taattcataa aacttttaac tttcacagtt aggtctctaa tccatttaga gcgtgctttt  61200
gcatgtagca ttaagctcca attttttattt tccttcaatt tcccagaagt ctctgctaaa  61260
taaactttcc tttctcattg atttgttttg tcaatttatc atttatccag tttggactaa  61320
agtcaatgta tgtggcttta tctctgaact tgttattctg cttcctttga tctatatgtt  61380
catttctagg ttgttaccat atttattact atgactttat actaggattt aatgtttgat  61440
aacagtaggt tctcacctca tttcctttct aaggttgagt ttgttatttg tggacatttc  61500
ttcatccttt attgaattcc tcaaaaaatc cagctacaat tttgattgtc attattattc  61560
atattataag ttcatttgta ggaaattgac atctgtataa tactaggggg ttccactgag  61620
acttttccat ttttacagat catcttcttt gttctttagt agtgttcaat ttctttttcc  61680
cctagtctta ctttctcttg aattaagtca atcctagata ctttacagta tgaaagtgaa  61740
agtgaaagtt gtatctgact ctttgtgacc ccatggacta tacagtccat ggaattctct  61800
aggccagaat actggagtgg gtagcctttc cttgctccag gcatcttcc caacccaggg  61860 atcaaaccca ggtctcccac attgcaggca gattctttac gaggtgagcc acaagggaag  61920
cccaagaata ctggagtggg tagcttatcc cttctccagt ggatcttcct gacccaggaa  61980
tcaaactggg gtctcctgca ttgtaggtgg tttctttacc aactgagcta tcagggaagc  62040
```

```
ccactttaca gtatgagttg aaattattac tatcttattt attaattttt ttctagtcaa    62100
ttattgctga tatagagaaa tgctgttgat tttttaaaac caatccatag ccttgctgaa    62160
ctctagttga gtttcctgtt acctctgcca agtgtgtgga attttctatg tatatgatca    62220
cattaattcc aaataatgac agctggagct cttttcttac agttattgca ccagtctttg    62280
tccttgcata tggcattgga agagggcttc ccaagtggct caatgttaaa gaatccacct    62340
atcaatgagg agatccaggt ttgattcctg ggtcaggaag atccctttga gaaggaaatg    62400
gccacccact ccgttgttct tgcctgggga atctaatgga cagaggagcc tggagaacta    62460
cagtccatgg ggtcacaaaa gagtcggaca caatctagca actaaaataa caataatggc    62520
actggaagga tctccagtcc tgtgacaggg gacgtccttg ttttgtttct gatcataaag    62580
ggactgcatt caaaaattat ctattaatta tgtttaccat ttctgttata taatctttat    62640
taagttaagc aggtttcctc ctattcctag tctgctaaga gtattttcct tagtgatagg    62700
tattcagttc agttcagtct gttgtgtccc actctttgtg tcctccatgg actgcagcat    62760
gccaggcttc cctgtctatc accaactccc agagcttact caaactcatg tccattgagt    62820
cagtgatgcc atccagtcat ctcatcctct gtcatcccct tctcctgccc tcaatctttc    62880
ccagcatcag ggtctttttcc agtgagttct tcacatcagg tggccaaagt gttggagttt    62940
cagcttcagc atcagtcctt ccaatgaata ttcaggactg atctccttta ggatggactg    63000
gttggatctc cctgcagtcc aagggactct caagagtctt ctccaacata acagttcaaa    63060
atctaggttg gtcataactt tccttccaag gagtaagcgt cttttaattt catggctgca    63120
atcaccatct gcagtgatat tggagcccca aaaataaaga taggtattga ctattatcaa    63180
atacttagta tcttgatgtg ctaaaggatt aggcagcaac ctgactattc tctgagaaca    63240
tcttatatga agtgttataa cacagccagg cattcagaaa cctaatgtgc atttctagta    63300
cttttactgt aatcacagat atgtttcttg aatttgctaa tctttgtagc ataatttgta    63360
cagtgagaga ttttggatta aataatacaa gatcttcttt attttatcac aaacagaaag    63420
aaaattctcc aaggtctcat taagttttga gttcttctta tttttagaaa tgattctcta    63480
cttcaaaaaa atttttatg attttcataa ttaagtgttg cttttgtgtt ctcaactgat    63540
tttaaaatga ttttgtctta atatagttta caattatcca actttattct aatattcaat    63600
tttaaagtaa tgatcagcaa catatgcccg tggccttatg tcctattgcc tgtatctcca    63660
gtccatggtc attcctcacc tccagactca ccaagcttac cagactgact ggtatctctt    63720
gtcccacgtg tagcttgata atggcattgt caaagagaca ctcctcattt gtcttcctat    63780
ggtcttgctc caccttccgt cttctgtcca cagaattgtc caatccagaa atctgggtgc    63840
cacctcaatt cttctagtct ttcatcttcc atgtcaaaca ccaagccttc cagaaagttc    63900
tcatgttcaa ttccctgagg tgtttgagca gaattgtgag cagcatggaa gccaagatct    63960
gagccccatg agcaaatgga gagatcaggg aagcaggcct gcaaaagacc aggtgcaaga    64020
atgaggccat ttggcatatc ccaggaccct gttcctctgg cctttaccca aaacagactc    64080
caaaaattct agtagacata gtctgagcag tttaactggc cttataactt tcaaatatat    64140
ttttatttat acccaggcat ttcaataatg atagtagaaa cataaatggg atgttaattc    64200
attgtttagt catccttcct ctgaatatta tccaagttag tctttagttc tgaaggtcat    64260
gaaaaataat tttataatat ttggtgccac ttttatttga agatgtccca gtgctgggga    64320
tgactaatgt cagcattaca acatatgcca ttttggtttt tatggcaaat ggtatttgg    64380
```

```
aacatgtagt tgatgtggg gtacagtaga aagtgtttaa tgatcattct actgtgcatc    64440
tttaatttct gcccttggaa ccacccaggg taagtgagat attcattctg aaagatctga    64500
atcttcaatt cattcatcta taatttgatg aatgtacatt cacaaaggtt cataggttat    64560
catgcaggat actttgttcc caaactgtgc ttgcccttac atgtaagata tgtgtctttt    64620
gtaccaaaaa ttaagagaaa ataagtcact tatgaaccat taaatgctga actaagactc    64680
attcagtgag tgagtaactg caaatactat gaacacagcc tttcttaccc cttttttgaat   64740 agccccattg tctgtctata gaaagaaaaa ttactttata ggtgtgtttg caaaatcttg    64800
cctgtttcct gtttccaaaa gttattgtat tgagaattcc tttgagaaaa ttcttgttgg    64860
gatttatgtg ttcagaagat gataattcct tcatttaaca gatatctatt gtgtaccttc    64920
tctgtgccag gctctgccct ggcccgctaa gaagatagca gcaaacaaaa gaggctcatt    64980
ccctgcttac attcctacat gaggaaagag gacatgaacc agctattcag aaaagtattt    65040
aatgatctca gcacctacct tggggtcttc ccaactggac attagaatca cttccatagg    65100
gcccatgcca gggttcagaa ggttccagga actaatatcc cttataacaa cccaataggc    65160
agagtttcta gggtccccac aagaacaagc ccagttgcaa gaatcactac tttaaagaag    65220
ttcaaagcta tggtaaacct accagatgtt tatagtttct tccaatttat gatacagtgt    65280
accagtcaga ggttattttt atcataagca atgttgctgg cattctacat ttatcaagtt    65340
actaggaaac agagccagga attattttaa ggtcaacttt gtccttagag aaggaagagt    65400
tgtgttaaca ctttacctat aattactttc gtgagatgta tggaatgtga agaatattta    65460
tgacctagac tgtttatagc tgatgccact gctatgcagt cattatgcta cagactttaa    65520
gtgattttta catgggcata tgatgctgac accctcttta ttttgcagat aagtcatcat    65580
ggtgaaaagc cacataggca gttggatcct ggttctcttt gtggccatgt ggagtgacgt    65640
gggcctctgc aagaagcgac caaaacctgg aggaggatgg aacactgggg ggagccgata    65700
cccaggacag ggcagtcctg gaggcaaccg ttatccacct cagggagggg gtggctgggg    65760
tcagccccat ggaggtggct ggggccagcc tcatggaggg ggctgggggcc agcctcatgg    65820 aggtggctgg ggtcagcccc atggtggtgg ctggggacag ccacatggtg gtggaggctg    65880
gggtcaaggt ggtacccacg gtcaatggaa caaacccagt aagccaaaaa ccaacatgaa    65940
gcatgtggca ggagctgctg cagctggagc agtggtaggg ggccttggtg gctacatgct    66000
gggaagtgcc atgagcaggc ctcttataca ttttggcagt gactatgagg accgttacta    66060
tcgtgaaaac atgcaccgtt accccaacca agtgtactac aggccagtgg atcagtatag    66120
taaccagaac aactttgtgc atgactgtgt caacatcaca gtcaaggaac acacagtcac    66180
caccaccacc aaggggggaga acttcaccga aactgacatc aagatgatgg agcgagtggt    66240
ggagcaaatg tgcattaccc agtaccagag agaatcccag gcttattacc aacgaggggc    66300
aagtgtgatc ctcttctctt cccctcctgt gatcctcctc atctctttcc tcattttcct    66360
catagtagga tagggcaac cttcctgttt tcattatctt cttaatcttt accaggttgg    66420
gggagggagt atctacctgc agcccgtag tggtggtgtc tcatttcttg cttctctctt    66480
tgttacctgt atgctaatac ccttggcgct tatagcactg ggaaatgaag agcagacatg    66540
agatgctgtt tattcaagtc ccgttagctc agtatgctaa tgccccatct tagcagtgat    66600
tttgtagcaa ttttctcatt tgtttcaaga acacgtgact acatttccct tttggaatag    66660
catttctgcc aagtctggaa ggaggccaca taatattcat tcaaaaaaac aaaccggaaa    66720
tccttagttc atagacccag ggtccacctg gttgagagct tgtgtcctgt gtctgcagag    66780
```

```
aactataaag gatattctgc attttgcagg ttacatttgc aggtaacaca gccagctatt    66840
gcatcaagaa tggatattca tgcaaccttt gacttacggg tagaggacat tttcacaagg    66900
aatgaacata atacgaaagg cttctgagac taaaaaattc aacatatgg gagaggtgcc     66960 cttggtggca gccttccatt ttgtatgttt aaagcacctt caagtggtat tcctttcttt    67020
agtaacaaag tatagataat taagttacct taatttaatt aaactacctt ctagacactg    67080
agagcaaatc tgttgtttat ctggaaccca ggatgatttt gacattgttt agagatgtga    67140
gagttgaact gtaaagaaag ctgagtgctg aagaattgat gcttttgaac tctagtgttg    67200
gagaaaactt gagagtccct tggactgcaa ggagatcaaa ttagtccatc ctaaaggaga    67260
tcagtcctga atattcattg gaaggactga tgctgaagct gaaactccaa tactttggcc    67320
acctgatggg aagaactgaa ggcaggagga gaagggatg acagaggatg agatggctgg     67380
atggcatcat ggattcaatg gacatgagct tgagtaaact ccaggagttg gcaatcgacg    67440
gagtcctggc atcctgcagt ccatggtgtc gcagagttgg acacgactga gtgactgaac    67500
tgaggtgaac ccagatttta acatagagaa tgcagatata aaaactccat attcatttga    67560
ttgaatcttt tccttaacca gtgctagtgt tggactggta agattataac aacaaatata    67620
ggttatgtga tgaagagaat agtgtacaaa gaaagaaat atgtgcattt ctttattgct      67680
atcataattg tcaaaaaaca aaattaggtc cttggtttct gtaaaattaa cttttgaatc    67740 aacaggagg catttaaaga aatatcttaa attagagaca gtagaaatct gatacattca     67800
gagtggaaaa agaaattcta ttacgattat ttaagaaggt aaaattattt cctgggttgt    67860
tcagtattgt cacctagcag atagacacta ttgttctgca ctgttattac tggcttgcac    67920
tttgtggtat cctatgtaaa aatacatata ttgcatatga cagacttaag aatttctgtt    67980
agagcaatta acatctgaac tatctaatgc attacctgtt tttgtaaggt acttttgta     68040 aggtactaag gagacgtggg tttaatccct aggtcatgta aatcccctgg aggaggaaat    68100
agcaacccac tccagtattc ttgccaggag aatcccatgg gcagaggagc ctggcagggt    68160
gcagtccatg catagggttg caaagagtca gacaagactt gagctactaa acaataacaa    68220
caataaatgc tgggttggct aaaaggttca ttaggttttt tttctgtaag atggctgtct    68280
ttaacttcat tcgaaacaat tttgttagat tgtatgtgac agctcttgta tcagcatgca    68340
tttgaaaaag aaaacaactt accaaaattg gtgaatttttt gtatagccat tttactattg   68400
aagatggaag aaaagaagca aaattttcag catatcatgc tgtattattt caagaaagat    68460
aacacaacca aaatgcgaaa atgtatttgt gcagtgtatg gagaaggtgc tgcaactgat    68520
caagcttgtc aaagtagttt gtgaagtttt gtgctggaga tttcttactg acaatgctc     68580 cacagtcggg tataccagtt gaagttgata gtgatcaaat tgagatattg agaacaatca    68640
atgttatacc acgtgggaga tagctgacat actcaaaata tccaaataga accttgaaaa    68700
ccatttgcac catctcagtt atgttaataa ctttgatgtt tgagttccac ataaattaag    68760
caaaaaaaaa acaaaaacaa aaacacacaa ccttgaccat atttgcatat gcagttctct    68820
actgaaatga atgaaaacac ttttgttttt aaaacagat tttgatgaac agtggatact      68880
atacaataac gtagaatgga aaagactgtg gggtgagcaa aatgaaccag caccaccaaa    68940
ggccaggctt catccaaaga agatgtgtgt atggtgggat tggaaagtaa tcctctatta    69000
tgggattctt ctggaaaacc aaaaaatcaa ttccaacaag tactgctcct aattagacca    69060
actgaaagca gcattcaatg aaaagcatcc agaattagtc aatagaaagc atataatctt    69120
```

```
ccatcaggat aacacaagac tacatttctt tgatgaccca gcatggctga gaggttctga   69180
ttcacctgct gtattcagac attgcatctt tggatttcca tttatttcag tctacagaat   69240
tatcatcatg aaaaaaattt ccattccctg gaagattgta aagtgcatct ggaaaacttc   69300
tttgctcaaa aagataaaaa gttttgtgaa cacagaatta tgaagttgcc tgaaaaacgg   69360
cagaagatag tgactatgtt gttcagtaaa gttcttggtg caaatgtgtc ttttatttt    69420 atttaaacac taaaggcacg ttttggccaa cccaatactg aatacttaaa ggaaactctt   69480
ccgtgttgtc cttagcctta cagcgtgcac tgaatagttt tgtataagaa tccagagtga   69540
tatttgaaat acgcatgtgc ttatattttc tatatttgta actttgcatg tacttgtttt   69600
gtgttaaaag tttataaata tttaatatct gactaaaatt aaacaggagc taaaaggagt   69660
atcttccacg gagtgtctgg ctgttttcac cagtgtgcac accatgttgg cagcttcatt   69720 tgggggggtta atatgagaaa agtggcacat tcagtcctca cactgccagt tgcggcagga   69780
gggcttctcc tgatcctgcc tcagcctac tcccagtcac atgccagctg ttctctgcta    69840
ccttttcata tttttccatg aatacccgtc aaagttacta ctatagcgga ggaaaacagt   69900
ccttgcattc tggaagattt tttctgacca ggatttgaa atagaggatt ttcgtgatta    69960
agatgagact taacaaagta tctaccttat gcctgtaccc acccttgaca ccatttcagg   70020
tcataaactg tgaggcctgg tgacaacacc cattgaattg aaattcaaca ctgtacggtc   70080
aatatggcta ctttcctttg ttacaggctt tcaaatggtt cttcatatgt ttcctccttc   70140
ccaagtatga ggtgccagct cccagttttc cttcacaaag gtttcttct gcaactgtag    70200 ttcattaaca gccggaagaa ataataaatg atagtggttg aaatcataac atttattaac   70260
actttaataa atgccagtgt ccttcagtat ctgaacagag gatcaacttt gcattaaaaa   70320
tgaaaagatt aaaaatcaac atcttgatat cccataattc acaaaataat ttaaaaatga   70380
cataaaatcc tcaaaagcat tactcagtta atctttaaca taagaagtgc taggactatt   70440
ttcatgctgt cctttggcc atatgtaaga ttatttaaaa atagactatt cattatctgc     70500
caatcataat ctcccaagaa taccccactg aaaagatgtc agttatacaa agcaaggtat   70560
ttacagggcc gaagtgaatg atacacatct gtattttct caggctacca tgttttcttc    70620
ctgttacttc caattccttt gagttgtgct aaagaaattt cttatatttt catatgtatt   70680
tttaaataga ggataattac tttacaatat tgtgatggtt tctgccatac atcagcatga   70740
atcagcatag ggcttcccag gtggcactag cggtaaagaa ctcacctgcc agtgcaggag   70800
acataagaga tgtgggttca atccctgagt caggaagatc ccctggaaga gggcatggca   70860
acccactcca gtattcttgc ctcgagaatc tccatgggca gagcagcccg gtgggccaca   70920
gtccataagg ttgcaaagag tcggacacaa ctgatgtgac ttagcatgca tgcatacata   70980
tggccccttc cctcttgaac cccctctacc acctccctcc ccacccaccc ctctaggttg   71040
tcgcagagta ctagctttgg tttccctgca tcatacattg aactctcact ggctggctgt   71100
tttacatatg gtatatgttt cagtgctatt ctctcatatc atctcacact ctccttccct   71160
tactgtgtcc aaaatgtctg tgtttccttt gctgccctgc aagtaggact atctttctag   71220
attccatata tatgtgttaa tgtatgatat ttgtctttct cttctaact tatttcactc     71280 tgtataatag gctctaggtt catccacctc attagaacag actcaaatat gttccttttt   71340
atggctgagt aatattccat tgtgtatatg taccacaact tcattatcca ttcatctgtc   71400
tatggttgga catctaggtt gtttccatgt cctaggtatt gtaaattgtg ctgcaataaa   71460
cattgaggta tatacatctt tttcagttct ggtttcctca gggtatatgc ccagtagtga   71520
```

```
gactgctggg tcatatggta actttgggct tcccttgtgg ctctgctggt aaagaatcca   71580
cctgcaatgc gggagacctg ggtttggtcc tgggctggga agacccccctg gagaagggaa   71640
tggctaccca ccccagtatt ctggcctcta gaattccatg gactgtatag tccatggagt   71700
tgcaaagagt tgcacacgac tgagcaactt tcactcacct atggtaactt tatttctagt   71760
cttttaagga aactccatac tgttctccat ggtggctgta tcagtttgca ttatgaccaa   71820
cagtgtcaga gagttccctt ttctccacat cctctccagc atttattttt tgtaaacttt   71880
ctgatgatgg ccattctgac caatatgaga tgacatctca ttgtagtttt gtttgcattt   71940
ctctaaaatg agtgatgttg agtatctttt catgtaatta ttagtcatct gtcatctttg   72000
gagaaatgtc tgtttgagtc ttctgcccat tttttaaatt tggttgtttt ttgttactga   72060
gctgcttatg tattttggag attaattcct ttcagttgtt tcatttgcta ttattttctc   72120
ccattctgag agttgtcttt tcaccttgct tatggtttcc ttcattgtga aaaaactttt   72180
aagtttaatt aggtcccact tatttatttt tgtttgtatt tccattattc taggaagggg   72240
gtcaaagagg atcttactat tctgcctatg ttttcctcta agagtcttat agtttctgat   72300
cttacattta ggtctttcat ccattttgag tttatctttg tgtatggtgt taggaagtgt   72360
tctaatttca ttcttttaca tgtagctgac cagttttccc agtaccagtt attgaagagg   72420
ctgtcttttc tccattgtat attttttgcct cttttgtcaa agataaggtc ctcatcagat   72480
cagatcagat cagatcagtc actcagtcat gtctgactct ttgcgacccc atgaatcgca   72540
gcatgccagg cctccctgtc caacaccaac tcccggagtt tactgagact cacgtccatc   72600
gagtcactga tgccatccag ccacctcatc ctctgtcatc ccctttttcct cctgccccca   72660
atccctccca gcatcagagt cttttccaat gagtcaactc tttgcatgag gtggccaaaa   72720
tattggagtt tcagctttag catcattcct tccaaagaaa tcccagggct gatgtccttc   72780
agaatggact ggttggatct ccttgcagtc ggactctcaa gagttctcca acaccacagt   72840
tcaaaagcat caattcttca gtgctcagcc ttcttcacag tccaactctc acatccatac   72900
atcaccacag gaaaaaccat agccttgact agatggacct tggttggcaa tgtctctgct   72960
tttgaatatg ctatctaggt tggtcataac tttccttcca aggagtaagc atctttaat    73020
ttcatggctg cagtcaccat ctgcagtgat tttggagccc agaaaaataa agtctgacac   73080
tttccactgt ttccccatct atttcccatg aagtaatggg accggatgcc atgatctttg   73140
ttttctaaat gttgagcttt aagccaactt tttcactctc cactttcact ttcatcaaga   73200
ggctttggtg catggattta tctccaggct ttctattttg ttccattggt ctatatttcc   73260
atttctgtga cagtaccata ctgtcttgat gaccatagct ttgtagtata gtctgaagtc   73320
aggaaggttg attcctccag tgtcattctt cttttctcaag attgctttgg ctatttgggg   73380
tcttttgtgt ttccatacaa attgtgaaag tatttgttct agttctgtga caaataccat   73440
tattagtttg ataggaattg cattgaatct atagattgct ttggataaca tagtcatttt   73500
cactatattg attcttccga tccaagaaca tggtatatct ctgagacagg aaacccgcgc   73560
tgtgagtgct tgatcaagcc caagagaata gtccgcaagc cggtttttgt gtgtttgttt   73620
ttggcccttt ggtaactatc ggtaaattta ttcctaggta ttttgttgt tgttgttgca    73680
atggtgaatg ggattgtttc cataatttct ctttctgatt tttcattgtt agtttatagg   73740
aatgcaaggg atttctgtgt attaatttta tatcctgtga ctttactgta ttcattgatt   73800
agctctagta attttttatgt ggcctcttta tagagtttcc tatatagagg atcacatgat   73860
```

```
ctgcaaacag agttttacta cttcttttcc aatctggatc cttgtgttaa aggatttta    73920
ctaaaaaatt aaaatatcaa ttttaaataa ctgagtctaa ctcttacaga aggtttttct    73980
ggagaagtgt caggtgtcaa actttctttc ccttcctctc tctctggaat taaagccaaa    74040
gaagtgtcct ctgccttgga agaaattttg ggtctgtatt gcttctcact ctagtgggaa    74100
ccttaatatg gccagaacct gagcttcccc aggctcaggc cctgaccttc cattggtcta    74160
agcaactgac ctacatagtt catttccact tgagaatggt cagttcctct ctggctcttt    74220
gaaactcctg gaggatttag cttctcctgc attaactgga ggaactaaac ccatcctttg    74280
ccccactcct gtgaggccta cccctgttct ccaagaagcc acaccttctg ctacacacat    74340
tcagcctatg agcttcaact ctgccttgct acaattttcc tttcctggag agctggtgtt    74400
ctgttctttc cctggagtag tgtgcctcaa acttgaatgt gcacctgaca ggggcccaag    74460
attctgcatt tcttacaggt tcccagatga tgccatgctg gttctgtgaa acttcactgg    74520
aacagctccc tcaggatttc acactggagc ctctaccagc accacctgaa gttcaacaca    74580
agttgctgca ccccaccccca gagtttctga ttccagagtg cagggtagga ccagagaatt    74640
tacatttcta acacactccc tggcaatgct gctgttgatg tggagattgc aaatggagct    74700
ccactgctct acaggaagat gtacatggaa tagaaggcaa cctggccctg aaaaatagag    74760
cagttaggag actaaaaatc taattggaat gctccctgag gaggagagag ctgagagctc    74820
tagggatgaa aagcaaagga gacataagga agtagttaat acctgctgcc tgaaaaactg    74880
gaagcactgg tgagtcctga ggcccaccac tagtgagaga ttcagctaaa cttggaatag    74940
tagccaggcc acaaatgcag cacttctcaa attcagatgt gcgcacaaat cacccaagaa    75000
ccctgtcaaa atgcagttct gaggccatat gtttgatgta agcttggaga tgtgtcattt    75060
ctataagctc ccaggtgatg tgtggtccca gtggtcccag gaccacacca agaaacaagg    75120
acctagaagc ctaagtcatc tcttctaacc gtggccaaga cttttaaataa gcattgaagt    75180
ctcaggagct gggggggaggt ggggagtagc caatagagag tcttcacctt tcttgattt    75240
agccctaagt tttgcctgtc gtgctttgag agcacattcc tcttacctat caacctcctg    75300
ctggcagcag tgaagtcagc ttgtgtatta tctctgaaac aagctgaatt agttggctgc    75360
ccatgggaaa tatcaaatcc agagacactc tgtcagtttt tcaaggtcat acaaatagtg    75420
agtgaaaatt ttagttgctc agtcatgtct gattctttgc aaacttatgg actatagctg    75480
ccaggctcct ctgtccatgg aattctccag gcaagaatac tggagtgggt tgccataccc    75540
tcctccaggg gatcttctgg acccggggat cttctggacc cagggatcaa accctctctc    75600
tgttgcaggc agattcttta ctgtctgagc caccagggaa gcccacacaa atagtatgtt    75660
caccaaagca cattgtggaa actctttgcc ttggtttgtg tttatattta agggtttggc    75720
tcaaaggtcc gacatctcag tcactgtgca caactcatgg cctctgtcaa gggtgccccc    75780
tggtgcaggg ctccagcttg aggggactca gttgaatcca aggggaacct gaaggaaggg    75840
tcagaaatcc taaaagcaaa ttcagcccaa aatgcctcct accctatttg attcctccat    75900
cactcactgt cccatacaca cttctctcat attatttcag aagtgacctg tagccagggc    75960
ccatagatta gtagccctct ccaatcaaac catagttccc taagccctag aacacataca    76020
tgtcacctcg tgccagagcc cctaggctgg aggccaccag ggtaattggg actgggggct    76080
tcttctctccc taactgtcct ggcaaatctg ccccttttcct ccttctctaa aaacaaacag    76140
taaacaaaca aaagcaagat cgttatctta atctttatat cgagtaaaaa taaaagtttt    76200
cagtaactct attctttagc acccttactc aacctaatca tttaagaaaa ccttacaggc    76260
```

```
ccttgtttca ttgcctttct tgttgaatat accatcttga ttagttttct ggggttgcca      76320
ttaaaaaaaa aaaaaagtgc cacagattga atggcttaaa caacagatat ttactttctc      76380
actcttctgg agactggaag tctgagatta aagtatcatc agggttggtt tcttctctga      76440
cttgtagatg gcctccctat gtcttcccac agtcttccct ttttgtgtct ctgtgtccta      76500 atctctttt ataaggacca gttcatgctc tatcatgaga ccctatggac tatagccctc       76560
taggctcctc tgtccatggg gttttccaga caagaatact gtgggttgct attttctcct      76620
ctaggcaatc tttctgaccc agggatcaag cccacgtgtc ctgtatctcc tgcattgcag      76680
atggattctt tactgctgag ccactgggga agcccttttta taaggactgg gcttcccttg     76740
tggctcggcc ggtaaagaat acacgtgcaa tgcaggagac cagggtttga tccctgggtc      76800
aggaagatcc cctggagaag ggaatggtaa cccactcctc aaattgtatt tgaggtgagg      76860
actgctactg ctgctgctaa gtcgctttag tcgtgtccaa ctctgtgcga ccccatagac      76920
ggcagcccat caggctctcc tgtccctggg attctccagg caagaacact ggagtgggtt      76980
gccatttcct tctccactgc atgaaagtga aagtgaaag tgaagtcacc actcctcaaa        77040
ttggatttga ggtaaggaca ccactcctca aattgaatta gggctcaccc taatggcttc      77100
atcttaacct aactttaact ctttaaaggc cctaactcca aatacagtca ttttgaggta      77160
ttaaggacta tgactccaac acctatcaag aaatgtcaca gcagtatgtt agtgtcagtc      77220
tcaagagcgc tcaaaggcag tcccaggact aagacaacct taatggcagc ctcacagtca      77280
cattctattc cctatcagg atcacactat tccttcaata gactgagcca ctgcccatca       77340
atccacttag aattgccaag ggtacctatc tcatagtgcc cattgcagag caaacagaaa      77400
tgcttccatt ctggatacag accctgaaac ccagccacca tgcccccatg gctcacacaa      77460
agagcttcat aatcaaacaa atttgcccct tggtttgtat ccacacacaa atacactaca      77520
aacacacctg gcttagagtt acactgatta tgagttaatt gacataaaac tgagtgttag      77580
ctataattta aggggtacta tctctaattt tcttgaagag atctctcatc tttcccattc      77640 tgttgtttc ctctatttct ttgcattggt ccctgagaaa ggcttcttta tctcttcttg       77700
ctattcttgg gaactctgca ttcagatgct tatatctttc cttttctcct ttgcttttcg      77760
cttctcttct tttcacagct atttgtaagg cctccccaga cagccatttt gcttttttgc      77820
atttcacgca aagatgggct tgataaagga cagaaatggt atggacctaa cagaagcagg      77880
agatattaag aagaggtggc aagaatacac agaagaactg tacaaaaaag atcttcatga      77940
cccagaaaat cacgatgatg tgatcactga cctagagcca gacatcctgg aatgtgaagt      78000
caagtgggcc ttaggaagca tcactaccaa caaagctagt ggaggtgatg gaattc          78056
```

<210> SEQ ID NO 2
<211> LENGTH: 771
<212> TYPE: DNA
<213> ORGANISM: Artificial Sequence
<220> FEATURE:
<223> OTHER INFORMATION: Majority Sequence prepared to show the
      alignment of bovine, ovine, cervid and human Prnp nucleotide
      sequences.

<400> SEQUENCE: 2

```
atggtgaaaa gccacatagg cagttggatc ctggttctct ttgtggccat gtggagtgac       60
gtgggcctct gcaagaagcg accaaaacct ggaggaggat ggaacactgg ggggagccga      120
tacccgggac agggcagtcc tggaggcaac cgctatccac ctcagggagg gggtggctgg      180
```

```
ggtcagcccc atggaggtgg ctggggccag cctcatggag gtggctgggg tcagccccat    240
ggtggtggct ggggacagcc ccatggtggt ggctgggggc atcaaggtgg tacccacagt    300
cagtggaaca agcccagtaa gccaaaaacc aacatgaagc atgtggcagg agctgctgca    360
gctggagcag tggtaggggg ccttggtggc tacatgctgg aaagtgccat gagcaggcct    420
cttatacatt ttggcagtga ctatgaggac cgttactatc gtgaaaacat gcaccgttac    480
cccaaccaag tgtactacag gccagtggat cagtatagta accagaacaa ctttgtgcat    540
gactgtgtca acatcacagt caagcaacac acagtcacca ccaccaccaa ggggagaac     600 ttcaccgaaa ctgacatcaa gatgatggag cgagtggtgg agcaaatgtg catcacccag    660
taccagagag aatcccaggc ttattaccaa agagggcaa gtgtgatcct cttctcttcc     720
cctcctgtga tcctcctcat ctctttcctc attttctca tagtaggata g              771
```

<210> SEQ ID NO 3
<211> LENGTH: 795
<212> TYPE: DNA
<213> ORGANISM: Bos taurus

<400> SEQUENCE: 3

```
atggtgaaaa gccacatagg cagttggatc ctggttctct ttgtggccat gtggagtgac     60
gtgggcctct gcaagaagcg accaaaacct ggaggaggat ggaacactgg ggggagccga    120
tacccaggac agggcagtcc tggaggcaac cgttatccac ctcagggagg gggtggctgg    180
ggtcagcccc atggaggtgg ctggggccag cctcatggag gtggctgggg ccagcctcat    240
ggaggtggct ggggtcagcc ccatggtggt ggctgggac agccacatgg tggtggaggc    300
tggggtcaag gtggtaccca cggtcaatgg aacaaaccca gtaagccaaa aaccaacatg    360
aagcatgtgg caggagctgc tgcagctgga gcagtggtag ggggccttgg tggctacatg    420
ctgggaagtg ccatgagcag gcctcttata catttggca gtgactatga ggaccgttac    480
tatcgtgaaa acatgcaccg ttaccccaac caagtgtact acaggccagt ggatcagtat    540
agtaaccaga caactttgt gcatgactgt gtcaacatca cagtcaagga acacacagtc    600
accaccacca ccaagggga gaacttcacc aaaactgaca tcaagatgat ggagcgagtg    660
gtggagcaaa tgtgcattac ccagtaccag agagaatccc aggcttatta ccaacgaggg    720
gcaagtgtga tcctcttctc ttcccctcct gtgatcctcc tcatctcttt cctcattttt    780
ctcatagtag gatag                                                    795
```

<210> SEQ ID NO 4
<211> LENGTH: 795
<212> TYPE: DNA
<213> ORGANISM: Bos taurus

<400> SEQUENCE: 4

```
atggtgaaaa gccacatagg cagttggatc ctggttctct ttgtggccat gtggagtgac     60
gtgggcctct gcaagaagcg accaaaacct ggaggaggat ggaacactgg ggggagccga    120
tacccaggac agggcagtcc tggaggcaac cgttatccac ctcagggagg gggtggctgg    180
ggtcagcccc atggaggtgg ctggggccag cctcatggag gtggctgggg ccagcctcat    240
ggaggtggct ggggtcagcc ccatggtggt ggctgggac agccacatgg tggtggaggc    300
tggggtcaag gtggtaccca cggtcaatgg aacaaaccya gtaagccaaa aaccaacatg    360
aagcatgtgg caggagctgc tgcagctgga gcagtggtag ggggccttgg tggctacatg    420
ctgggaagtg ccatgagcag gcctcttata catttggca gtgactatga ggaccgttac    480
```

```
tatcgtgaaa acatgcaccg ttaccccaac caagtgtact acaggccagt ggatcagtat      540
agtaaccaga acaactttgt gcatgactgt gtcaacatca cagtcaagga acacacagtc      600
accaccacca ccaaggggga gaacttcacc gaaactgaca tcaagatgat ggagcgagtg      660
gtggagcaaa tgtgcattac ccagtaccag agagaatccc aggcttatta ccaacgaggg      720
gcaagtgtga tcctcttctc ttcccctcct gtgatcctcc tcatctcttt cctcattttt      780
ctcatagtag gatag                                                      795

<210> SEQ ID NO 5
<211> LENGTH: 845
<212> TYPE: DNA
<213> ORGANISM: Bos taurus

<400> SEQUENCE: 5
atggtgaaaa gccacatagg cagttggatc ctggttctct ttgtggccat gtggagtgac       60
gtgggcctyt gcaagaagcg accaaaacct ggaggaggat ggaacacwgg ggggagccga      120
tacccrggac agggcaktcc tggaggcaac cgttatccac ctcagggagg gggtggctgg      180
ggtcagcccc atggaggtgg ctggggccag cctcatggag gtggctgggg ccarcctcat      240
ggaggtggct ggggtcagcc ccatggtggt ggctggggac agccacatgg tggtggaggc      300
tggggtcaag gtggtaccca cggtcaatgg aacaaaccya gtaagccaaa aaccaacatg      360
aagcatgtgg caggagctgc tgcagctgga gcagtggtag ggggccttgg tggctacatg      420
ctgggaagtg ccatgagcag gcctcttata cattttggca rtgactatga ggaccgttac      480
tatcgtgaaa acatgcaccg ttaccccaac caagtgtact acaggccagt ggatcagtat      540
agtaaccaga acaaytttgt gcatgactgt gtcaayatca cagtcaagga acacacagtc      600
accaccacca ccaaggggga gaacttcacy gaaactgaca tcaagatgat ggagcgagtg      660
gtggagcaaa tgtgyatyac ccagtaccag agagaatccc aggcttatta ccaacgaggg      720
gcaagtgtga tcctcttctc ttcccctcct gtgatcctcc tcatctcttt cctcattttt      780
ctcatagtag gataggggca accttcctgt tttcattatc ttcttaatct ttaccaggtt      840
ggggg                                                                  845

<210> SEQ ID NO 6
<211> LENGTH: 936
<212> TYPE: DNA
<213> ORGANISM: Bos taurus

<400> SEQUENCE: 6
tatgatgctg acaccctctt tattttgcag ataagtcatc atggtgaaaa gccacatagg       60
cagttggatc ctggttctct ttgtggccat gtggagtgac gtgggcctct gcaagaagcg      120
accaaaacct ggaggaggat ggaacactgg ggggagccga tacccaggac agggcagtcc      180
tggaggcaac cgttatccac ctcagggagg gggtggctgg ggtcagcccc atggaggtgg      240
ctggggccag cctcatggag gtggctgggg ccagcctcat ggaggtggct ggggtcagcc      300
ccatggtggt ggctggggac agccacatgg tggtggaggc tggggtcaag gtggtaccca      360
cggtcaatgg aacaaaccca gtaagccaaa aaccaacatg aagcatgtgg caggagctgc      420
tgcagctgga gcagtggtag ggggccttgg tggctacatg ctgggaagtg ccatgagcag      480
gcctcttata cattttggca gtgactatga ggaccgttac tatcgtgaaa acatgcaccg      540
ttaccccaac caagtgtact acaggccagt ggatcagtat agtaaccaga acaactttgt      600
```

```
gcatgactgt gtcaacatca cagtcaagga acacacagtc accaccacca ccaagggga      660 gaacttcacc gaaactgaca tcaagatgat ggagcgagtg gtggagcaaa tgtgcattac     720
ccagtaccag agagaatccc aggcttatta ccaacgaggg gcaagtgtga tcctcttctc    780
ttcccctcct gtgatcctcc tcatctcttt cctcattttt ctcatagtag gatagggca     840 accttcctgt tttcattatc ttcttaatct ttaccaggtt gggggaggga gtatctacct    900 gcagcccgt agtggtggtg tctcatttct tgcttc                              936

<210> SEQ ID NO 7
<211> LENGTH: 771
<212> TYPE: DNA
<213> ORGANISM: Ovis canadensis

<400> SEQUENCE: 7
atggtgaaaa gccacatagg cagttggatc ctggttctct ttgtggccat gtggagtgac     60
gtgggcctct gcaagaagcg accaaaacct ggcggaggat ggaacactgg ggggagccga    120
tacccgggac agggcagtcc tgaggcaac cgctatccac ctcagggagg gggtggctgg     180
ggtcagcccc atggaggtgg ctggggccaa cctcatggag gtggctgggg tcagccccat    240
ggtggtggct ggggacagcc acatggtggt ggaggctggg gtcaaggtgg tagccacagt    300
cagtggaata gcccagtaa gccaaaaacc aacatgaagc atgtggcagg agctgctgca    360
gctggagcag tggtaggggg ccttggtggc tacatgctgg gaagtgccat gagcaggcct    420
cttatacatt ttggcaatga ctatgaggac cgttactatc gtgaaaacat gtaccgttac    480
cccaaccaag tgtactacag accagtggat cagtatagta accagaacaa ctttgtgcat    540
gactgtgtca acatcacagt caagcaacac acagtcacca ccaccaccaa ggggagaac    600 ttcaccgaaa ctgacatcaa gataatggag cgagtggtgg agcaaatgtg catcacccag    660
taccagagag aatcccaggc ttattaccaa agggggcaa gtgtgatcct cttttcttcc    720
cctcctgtga tcctcctcat ctctttcctc attttctca tagtaggata g              771

<210> SEQ ID NO 8
<211> LENGTH: 771
<212> TYPE: DNA
<213> ORGANISM: Ovis aries

<400> SEQUENCE: 8
atggtgaaaa gccacatagg cagttggatc ctggttctct ttgtggccat gtggagtgac     60
gtgggcctct gcaagaagcg accaaaacct ggcggaggat ggaacactgg ggggagccga    120
tacccgggac agggcagtcc tgaggcaac cgctatccac ctcagggagg gggtggctgg     180
ggtcagcccc atggaggtgg ctggggccaa cctcatggag gtggctgggg tcagccccat    240
ggtggtggct ggggacagcc acatggtggt ggaggctggg gtcaaggtgg tagccacagt    300
cagtggaaca gcccagtaa gccaaaaacc aacatgaagc atgtggcagg agctgctgca    360
gctggagcag tggtaggggg ccttggtggc tacatgctgg gaagtgccat gagcaggcct    420
tttatacatt ttggcaatga ctatgaggac cgttactatc gtgaaaacat gtaccgttac    480
cccaaccaag tgtactacag accagtggat cagtatagta accagaacaa ctttgtgcat    540
gactgtgtca acatcacagt caagcaacac acagtcacca ccaccaccaa ggggagaac    600 ttcaccgaaa ctgacatcaa gataatggag cgagtggtgg agcaaatgtg catcacccag    660
taccagagag aatcccaggc ttattaccaa agggggcaa gtgtgatcct cttttcttcc    720
cctcctgtga tcctcctcat ctctttcctc attttctca tagtaggata g              771
```

<210> SEQ ID NO 9
<211> LENGTH: 771
<212> TYPE: DNA
<213> ORGANISM: Odocoileus virginianus

<400> SEQUENCE: 9

| | | | | | |
|---|---|---|---|---|---|
| atggtgaaaa | gccacatagg | cagctggatc | ctagttctct | tgtggccat | gtggagtgat | 60 |
| gtgggcctct | gcaagaagcg | accaaaacct | ggaggaggat | ggaacactgg | ggggagccga | 120 |
| tacccgggac | agggaagtcc | tggaggcaac | cgctatccac | ctcagggagg | gggtggctgg | 180 |
| ggtcagcccc | atggaggtgg | ctggggccaa | cctcatggag | gtggctgggg | tcagccccat | 240 |
| ggtggtggct | gggggcagcc | acatggtggt | ggaggctggg | gtcaaggtgg | tacccacagt | 300 |
| cagtggaaca | agcccagtaa | accaaaaacc | aacatgaagc | atgtgggagg | agctgctgcc | 360 |
| gctggagcag | tggtaggggg | ccttggtggc | tacatgctgg | gaagtgccat | gagcagacct | 420 |
| cttatacatt | ttggcaacga | ctatgaggac | cgttactatc | gtgaaaacat | gtaccgttac | 480 |
| cccaaccaag | tgtactacag | gccagtggat | cagtataata | accagaacac | ctttgtgcat | 540 |
| gactgtgtca | acatcacagt | caagcaacac | acagtcacca | ccaccaccaa | ggggagaac | 600 |
| ttcaccgaaa | ctgacattaa | gatgatggag | cgagttgtgg | agcaaatgtg | catcacccag | 660 |
| taccagagag | aatcccaggc | ttattaccaa | agaggggcaa | gtgtgatcct | cttctcctcc | 720 |
| cctcctgtga | tcctcctcat | ctctttcctc | attttttctca | tagtaggata | g | 771 |

<210> SEQ ID NO 10
<211> LENGTH: 771
<212> TYPE: DNA
<213> ORGANISM: cervus canadensis

<400> SEQUENCE: 10

| | | | | | |
|---|---|---|---|---|---|
| atggtgaaaa | gccacatagg | cagctggatc | ctagttctct | tgtggccat | gtggagtgac | 60 |
| gtcggcctct | gcaagaagcg | accaaaacct | ggaggaggat | ggaacactgg | ggggagccga | 120 |
| tacccgggac | agggaagtcc | tggaggcaac | cgctatccac | ctcagggagg | gggtggctgg | 180 |
| ggtcagcccc | atggaggtgg | ctggggccaa | cctcatggag | gtggctgggg | tcagccccat | 240 |
| ggtggtggct | ggggacagcc | acatggtggt | ggaggctggg | gtcaaggtgg | tacccacagt | 300 |
| cagtggaaca | agcccagtaa | accaaaaacc | aacatgaagc | atgtggcagg | agctgctgca | 360 |
| gctggagcag | tggtaggggg | cctcggtggc | tacatgctgg | gaagtgccat | gagcaggcct | 420 |
| cttatacatt | ttggcaatga | ctatgaggac | cgttactatc | gtgaaaacat | gtaccgttac | 480 |
| cccaaccaag | tgtactacag | gccagtggat | cagtataata | accagaacac | ctttgtgcat | 540 |
| gactgtgtca | acatcacagt | caagcaacac | acagtcacca | ccaccaccaa | ggggagaac | 600 |
| ttcaccgaaa | ctgacatcaa | gatgatggag | cgagttgtgg | agcaaatgtg | catcacccag | 660 |
| taccagagag | aatccgaggc | ttattaccaa | agaggggcaa | gtgtgatcct | cttctcctcc | 720 |
| cctcctgtga | tcctcctcat | ctctttcctc | attttttctca | tagtaggata | g | 771 |

<210> SEQ ID NO 11
<211> LENGTH: 762
<212> TYPE: DNA
<213> ORGANISM: Homo sapiens

<400> SEQUENCE: 11

| | | | | | |
|---|---|---|---|---|---|
| atggcgaacc | ttggctgctg | gatgctggtt | ctctttgtgg | ccacatggag | tgacctgggc | 60 |

| | |
|---|---:|
| ctctgcaaga agcgcccgaa gcctggagga tggaacactg ggggcagccg atacccgggg | 120 |
| cagggcagcc ctggaggcaa ccgctaccca cctcagggcg gtggtggctg ggggcagcct | 180 |
| catggtggtg gctgggggga gcctcatggt ggtggctggg ggcagcccca tggtggtggc | 240 |
| tggggacagc ctcatggtgg tggctggggt caaggaggtg gcacccacag tcagtggaac | 300 |
| aagccgagta agccaaaaac caacatgaag cacatggctg gtgctgcagc agctggggca | 360 |
| gtggtggggg gccttggcgg ctacatgctg ggaagtgcca tgagcaggcc catcatacat | 420 |
| ttcggcagtg actatgagga ccgttactat cgtgaaaaca tgcaccgtta ccccaaccaa | 480 |
| gtgtactaca ggcccatgga tgagtacagc aaccagaaca ctttgtgcc tgactgcgtc | 540 |
| aatatcacaa tcaagcagca cacggtcacc acaaccacca aggggagaa cttcaccgag | 600 |
| accgacgtta agatgatgga gcgcgtggtt gagcagatgt gtatcaccca gtaggagagg | 660 |
| gaatctcagg cctattacca gagaggatcg agcatggtcc tcttctcctc tccacctgtg | 720 |
| atcctcctga tctcttttcct catcttcctg atagtgggat ga | 762 |

<210> SEQ ID NO 12
<211> LENGTH: 762
<212> TYPE: DNA
<213> ORGANISM: Homo sapiens

<400> SEQUENCE: 12

| | |
|---|---:|
| atggcgaacc ttggctgctg gatgctggtt ctctttgtgg ccacatggag tgacctgggc | 60 |
| ctctgcaaga agcgcccgaa gcctggagga tggaacactg ggggcagccg atacccgggg | 120 |
| cagggcagcc ctggaggcaa ccgctaccca cctcagggcg gtggtggctg ggggcagcct | 180 |
| catggtggtg gctgggggca gccccatggt ggtggctggg ggcagcccca tggtggtggc | 240 |
| tggggacagc ctcatggtgg tggctggggt caaggaggtg gcacccacag tcagtggaac | 300 |
| aagctgagta agataaaaac caacatgaag cacatggctg gtgctgcagt ggctggggca | 360 |
| gtggtggggg gcgttggcgg ctacgtgctg gtaagtgcca tgagcaggcc catgatacat | 420 |
| ttcagcagtg actatgagga ccgttactat cgtgaaaaca tgcaccgtta ccccaaccaa | 480 |
| gtatactaca ggcccatgga tgagtacagc agccagaata actttgtgca taactgcatc | 540 |
| aatatcgcaa tcaagcagcg cggagtcacc acaaccacca aggggaagaa ctccaccaag | 600 |
| accaatatta agatgatgga gcatgtgatt cagccaatgt gtatcacccg gtagaagagg | 660 |
| gaatctcagg cctattacca gaggggatca agcaggtcc tcttctcctc ttcacctgtg | 720 |
| atcctcctga tctcttttcct catcttcctg atagtgggat ga | 762 |

<210> SEQ ID NO 13
<211> LENGTH: 256
<212> TYPE: PRT
<213> ORGANISM: Artificial Sequence
<220> FEATURE:
<223> OTHER INFORMATION: Majority Sequence prepared to show the
      alignment of bovine, ovine, cervid, and human Prnp nucleotide
      sequences.

<400> SEQUENCE: 13

Met Val Lys Ser His Ile Gly Ser Trp Ile Leu Val Leu Phe Val Ala
 1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

-continued

```
Gly Asn Arg Tyr Pro Pro Gln Gly Gly Gly Trp Gly Gln Pro His
 50                  55                  60
Gly Gly Gly Trp Gly Gln Pro His Gly Gly Gly Trp Gly Gln Pro His
 65                  70                  75                  80
Gly Gly Gly Trp Gly Gln Pro His Gly Gly Gly Trp Gly Gln Gln Gly
                 85                  90                  95
Gly Thr His Ser Gln Trp Asn Lys Pro Ser Lys Pro Lys Thr Asn Met
                100                 105                 110
Lys His Val Ala Gly Ala Ala Ala Ala Gly Ala Val Val Gly Gly Leu
            115                 120                 125
Gly Gly Tyr Met Leu Gly Ser Ala Met Ser Arg Pro Leu Ile His Phe
            130                 135                 140
Gly Ser Asp Tyr Glu Asp Arg Tyr Tyr Arg Glu Asn Met His Arg Tyr
145                 150                 155                 160
Pro Asn Gln Val Tyr Tyr Arg Pro Val Asp Gln Tyr Ser Asn Gln Asn
                165                 170                 175
Asn Phe Val His Asp Cys Val Asn Ile Thr Val Lys Gln His Thr Val
            180                 185                 190
Thr Thr Thr Thr Lys Gly Glu Asn Phe Thr Glu Thr Asp Ile Lys Met
            195                 200                 205
Met Glu Arg Val Val Glu Gln Met Cys Ile Thr Gln Tyr Gln Arg Glu
210                 215                 220
Ser Gln Ala Tyr Tyr Gln Arg Gly Ala Ser Val Ile Leu Phe Ser Ser
225                 230                 235                 240
Pro Pro Val Ile Leu Leu Ile Ser Phe Leu Ile Phe Leu Ile Val Gly
                245                 250                 255

<210> SEQ ID NO 14
<211> LENGTH: 264
<212> TYPE: PRT
<213> ORGANISM: Bos taurus

<400> SEQUENCE: 14

Met Val Lys Ser His Ile Gly Ser Trp Ile Leu Val Leu Phe Val Ala
 1                5                  10                  15
Met Trp Ser Asp Val Gly Leu Cys Lys Lys Arg Pro Lys Pro Gly Gly
                 20                  25                  30
Gly Trp Asn Thr Gly Gly Ser Arg Tyr Pro Gly Gln Gly Ser Pro Gly
             35                  40                  45
Gly Asn Arg Tyr Pro Pro Gln Gly Gly Gly Trp Gly Gln Pro His
 50                  55                  60
Gly Gly Gly Trp Gly Gln Pro His Gly Gly Gly Trp Gly Gln Pro His
 65                  70                  75                  80
Gly Gly Gly Trp Gly Gln Pro His Gly Gly Gly Trp Gly Gln Pro His
                 85                  90                  95
Gly Gly Gly Gly Trp Gly Gln Gly Gly Thr His Gly Gln Trp Asn Lys
                100                 105                 110
Pro Ser Lys Pro Lys Thr Asn Met Lys His Val Ala Gly Ala Ala Ala
            115                 120                 125
Ala Gly Ala Val Val Gly Gly Leu Gly Gly Tyr Met Leu Gly Ser Ala
            130                 135                 140
Met Ser Arg Pro Leu Ile His Phe Gly Ser Asp Tyr Glu Asp Arg Tyr
145                 150                 155                 160
Tyr Arg Glu Asn Met His Arg Tyr Pro Asn Gln Val Tyr Tyr Arg Pro
                165                 170                 175
```

```
Val Asp Gln Tyr Ser Asn Gln Asn Asn Phe Val His Asp Cys Val Asn
            180                 185                 190

Ile Thr Val Lys Glu His Thr Val Thr Thr Thr Lys Gly Glu Asn
        195                 200                 205

Phe Thr Lys Thr Asp Ile Lys Met Met Glu Arg Val Val Glu Gln Met
    210                 215                 220

Cys Ile Thr Gln Tyr Gln Arg Glu Ser Gln Ala Tyr Tyr Gln Arg Gly
225                 230                 235                 240

Ala Ser Val Ile Leu Phe Ser Ser Pro Val Ile Leu Leu Ile Ser
            245                 250                 255

Phe Leu Ile Phe Leu Ile Val Gly
            260

<210> SEQ ID NO 15
<211> LENGTH: 264
<212> TYPE: PRT
<213> ORGANISM: Bos taurus

<400> SEQUENCE: 15

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Pro His
            85                  90                  95

Gly Gly Gly Gly Trp Gly Gln Gly Gly Thr His Gly Gln Trp Asn Lys
            100                 105                 110

Pro Ser Lys Pro Lys Thr Asn Met Lys His Val Ala Gly Ala Ala Ala
            115                 120                 125

Ala Gly Ala Val Val Gly Gly Leu Gly Gly Tyr Met Leu Gly Ser Ala
    130                 135                 140

Met Ser Arg Pro Leu Ile His Phe Gly Ser Asp Tyr Glu Asp Arg Tyr
145                 150                 155                 160

Tyr Arg Glu Asn Met His Arg Tyr Pro Asn Gln Val Tyr Tyr Arg Pro
                165                 170                 175

Val Asp Gln Tyr Ser Asn Gln Asn Asn Phe Val His Asp Cys Val Asn
            180                 185                 190

Ile Thr Val Lys Glu His Thr Val Thr Thr Thr Lys Gly Glu Asn
        195                 200                 205

Phe Thr Glu Thr Asp Ile Lys Met Met Glu Arg Val Val Glu Gln Met
    210                 215                 220

Cys Ile Thr Gln Tyr Gln Arg Glu Ser Gln Ala Tyr Tyr Gln Arg Gly
225                 230                 235                 240

Ala Ser Val Ile Leu Phe Ser Ser Pro Val Ile Leu Leu Ile Ser
            245                 250                 255

Phe Leu Ile Phe Leu Ile Val Gly
            260
```

<210> SEQ ID NO 16
<211> LENGTH: 264
<212> TYPE: PRT
<213> ORGANISM: Bos taurus
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (154)..(154)
<223> OTHER INFORMATION: Xaa can be any naturally occurring amino acid

<400> SEQUENCE: 16

```
Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Xaa Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Trp Gly Gln Pro His
65                  70                  75                  80

Gly Gly Gly Trp Gly Gln Pro His Gly Gly Trp Gly Gln Pro His
                85                  90                  95

Gly Gly Gly Gly Trp Gly Gln Gly Gly Thr His Gly Gln Trp Asn Lys
            100                 105                 110

Pro Ser Lys Pro Lys Thr Asn Met Lys His Val Ala Gly Ala Ala Ala
        115                 120                 125

Ala Gly Ala Val Val Gly Gly Leu Gly Gly Tyr Met Leu Gly Ser Ala
    130                 135                 140

Met Ser Arg Pro Leu Ile His Phe Gly Xaa Asp Tyr Glu Asp Arg Tyr
145                 150                 155                 160

Tyr Arg Glu Asn Met His Arg Tyr Pro Asn Gln Val Tyr Tyr Arg Pro
                165                 170                 175

Val Asp Gln Tyr Ser Asn Gln Asn Asn Phe Val His Asp Cys Val Asn
            180                 185                 190

Ile Thr Val Lys Glu His Thr Val Thr Thr Thr Thr Lys Gly Glu Asn
        195                 200                 205

Phe Thr Glu Thr Asp Ile Lys Met Met Glu Arg Val Val Glu Gln Met
    210                 215                 220

Cys Ile Thr Gln Tyr Gln Arg Glu Ser Gln Ala Tyr Tyr Gln Arg Gly
225                 230                 235                 240

Ala Ser Val Ile Leu Phe Ser Ser Pro Pro Val Ile Leu Leu Ile Ser
                245                 250                 255

Phe Leu Ile Phe Leu Ile Val Gly
            260
```

<210> SEQ ID NO 17
<211> LENGTH: 264
<212> TYPE: PRT
<213> ORGANISM: Bos taurus

<400> SEQUENCE: 17

```
Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30
```

Gly Trp Asn Thr Gly Gly Ser Arg Tyr Pro Gly Gln Gly Ser Pro Gly
            35                  40                  45

Gly Asn Arg Tyr Pro Pro Gln Gly Gly Gly Trp Gly Gln Pro His
        50                  55                  60

Gly Gly Gly Trp Gly Gln Pro His Gly Gly Trp Gly Gln Pro His
65                  70                  75                  80

Gly Gly Gly Trp Gly Gln Pro His Gly Gly Trp Gly Gln Pro His
                85                  90                  95

Gly Gly Gly Gly Trp Gly Gln Gly Gly Thr His Gly Gln Trp Asn Lys
            100                 105                 110

Pro Ser Lys Pro Lys Thr Asn Met Lys His Val Ala Gly Ala Ala Ala
            115                 120                 125

Ala Gly Ala Val Val Gly Leu Gly Gly Tyr Met Leu Gly Ser Ala
        130                 135                 140

Met Ser Arg Pro Leu Ile His Phe Gly Ser Asp Tyr Glu Asp Arg Tyr
145                 150                 155                 160

Tyr Arg Glu Asn Met His Arg Tyr Pro Asn Gln Val Tyr Tyr Arg Pro
                165                 170                 175

Val Asp Gln Tyr Ser Asn Gln Asn Asn Phe Val His Asp Cys Val Asn
            180                 185                 190

Ile Thr Val Lys Glu His Thr Val Thr Thr Thr Lys Gly Glu Asn
        195                 200                 205

Phe Thr Glu Thr Asp Ile Lys Met Met Glu Arg Val Val Glu Gln Met
    210                 215                 220

Cys Ile Thr Gln Tyr Gln Arg Glu Ser Gln Ala Tyr Tyr Gln Arg Gly
225                 230                 235                 240

Ala Ser Val Ile Leu Phe Ser Ser Pro Val Ile Leu Leu Ile Ser
                245                 250                 255

Phe Leu Ile Phe Leu Ile Val Gly
            260

<210> SEQ ID NO 18
<211> LENGTH: 256
<212> TYPE: PRT
<213> ORGANISM: Ovis canadensis

<400> SEQUENCE: 18

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Trp Gly Gln Pro His
65                  70                  75                  80

Gly Gly Gly Trp Gly Gln Pro His Gly Gly Gly Trp Gly Gln Gly
                85                  90                  95

Gly Ser His Ser Gln Trp Asn Lys Pro Ser Lys Pro Lys Thr Asn Met
            100                 105                 110

Lys His Val Ala Gly Ala Ala Ala Ala Gly Ala Val Val Gly Gly Leu
        115                 120                 125

Gly Gly Tyr Met Leu Gly Ser Ala Met Ser Arg Pro Leu Ile His Phe

```
                130                 135                 140
Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Ser Asn Gln Asn
                165                 170                 175

Asn Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Ile
        195                 200                 205

Met Glu Arg Val Val Glu Gln Met Cys Ile Thr Gln Tyr Gln Arg Glu
210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255

<210> SEQ ID NO 19
<211> LENGTH: 264
<212> TYPE: PRT
<213> ORGANISM: Ovis aries

<400> SEQUENCE: 19

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Pro His
                85                  90                  95

Gly Gly Gly Gly Trp Gly Gln Gly Gly Thr His Gly Gln Trp Asn Lys
            100                 105                 110

Pro Ser Lys Pro Lys Thr Asn Met Lys His Val Ala Gly Ala Ala Ala
        115                 120                 125

Ala Gly Ala Val Val Gly Gly Leu Gly Gly Tyr Met Leu Gly Ser Ala
    130                 135                 140

Met Ser Arg Pro Leu Ile His Phe Gly Ser Asp Tyr Glu Asp Arg Tyr
145                 150                 155                 160

Tyr Arg Glu Asn Met His Arg Tyr Pro Asn Gln Val Tyr Tyr Arg Pro
                165                 170                 175

Val Asp Gln Tyr Ser Asn Gln Asn Asn Phe Val His Asp Cys Val Asn
            180                 185                 190

Ile Thr Val Lys Glu His Thr Val Thr Thr Thr Lys Gly Glu Asn
        195                 200                 205

Phe Thr Glu Thr Asp Ile Lys Met Met Glu Arg Val Val Glu Gln Met
    210                 215                 220

Cys Ile Thr Gln Tyr Gln Arg Glu Ser Gln Ala Tyr Tyr Gln Arg Gly
225                 230                 235                 240

Ala Ser Val Ile Leu Phe Ser Ser Pro Pro Val Ile Leu Leu Ile Ser
                245                 250                 255
```

```
Phe Leu Ile Phe Leu Ile Val Gly
        260

<210> SEQ ID NO 20
<211> LENGTH: 256
<212> TYPE: PRT
<213> ORGANISM: Odocoileus virginianus

<400> SEQUENCE: 20

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Gly
                85                  90                  95

Gly Thr His Ser Gln Trp Asn Lys Pro Ser Lys Pro Lys Thr Asn Met
            100                 105                 110

Lys His Val Gly Gly Ala Ala Ala Ala Gly Ala Val Val Gly Gly Leu
        115                 120                 125

Gly Gly Tyr Met Leu Gly Ser Ala Met Ser Arg Pro Leu Ile His Phe
    130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Asn Asn Gln Asn
                165                 170                 175

Thr Phe Val His Asp Cys Val Asn Ile Thr Val Lys Gln His Thr Val
            180                 185                 190

Thr Thr Thr Thr Lys Gly Glu Asn Phe Thr Glu Thr Asp Ile Lys Met
        195                 200                 205

Met Glu Arg Val Val Glu Gln Met Cys Ile Thr Gln Tyr Gln Arg Glu
    210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255

<210> SEQ ID NO 21
<211> LENGTH: 256
<212> TYPE: PRT
<213> ORGANISM: cervus canadensis

<400> SEQUENCE: 21

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Gly Trp Gly Gln Pro His
    50                  55                  60
```

```
Gly Gly Gly Trp Gly Gln Pro His Gly Gly Gly Trp Gly Gln Pro His
 65                  70                  75                  80

Gly Gly Gly Trp Gly Gln Pro His Gly Gly Gly Trp Gly Gln Gly
                 85                  90                  95

Gly Thr His Ser Gln Trp Asn Lys Pro Ser Lys Pro Thr Asn Met
            100                 105                 110

Lys His Val Ala Gly Ala Ala Ala Gly Ala Val Val Gly Gly Leu
            115                 120                 125

Gly Gly Tyr Met Leu Gly Ser Ala Met Ser Arg Pro Leu Ile His Phe
            130                 135                 140

Gly Asn Asp Tyr Glu Asp Arg Tyr Tyr Arg Glu Asn Met Tyr Arg Tyr
145                 150                 155                 160

Pro Asn Gln Val Tyr Tyr Arg Pro Val Asp Gln Tyr Asn Asn Gln Asn
                165                 170                 175

Thr Phe Val His Asp Cys Val Asn Ile Thr Val Lys Gln His Thr Val
                180                 185                 190

Thr Thr Thr Thr Lys Gly Glu Asn Phe Thr Glu Thr Asp Ile Lys Met
            195                 200                 205

Met Glu Arg Val Val Glu Gln Met Cys Ile Thr Gln Tyr Gln Arg Glu
210                 215                 220

Ser Glu Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255

<210> SEQ ID NO 22
<211> LENGTH: 265
<212> TYPE: PRT
<213> ORGANISM: Homo sapiens
<220> FEATURE:
<221> NAME/KEY: misc_feature
<222> LOCATION: (95)..(102)
<223> OTHER INFORMATION: Xaa can be any naturally occurring amino acid
<220> FEATURE:
<221> NAME/KEY: misc_feature
<222> LOCATION: (265)..(265)
<223> OTHER INFORMATION: Xaa can be any naturally occurring amino acid

<400> SEQUENCE: 22

Met Ala Asn Ser His Leu Gly Cys Trp Met Leu Val Leu Phe Val Ala
  1               5                  10                  15

Met Trp Thr Asp Leu Gly Leu Cys Lys Lys Arg Pro Lys Pro Gly Gly
             20                  25                  30

Gly Trp Asn Thr Gly Gly Ser Arg Tyr Pro Gly Gln Gly Ser Pro Gly
             35                  40                  45

Gly Asn Arg Tyr Pro Pro Gln Gly Gly Gly Trp Gly Gln Pro His
 50                  55                  60

Gly Gly Gly Trp Gly Gln Pro His Gly Gly Gly Trp Gly Gln Pro His
 65                  70                  75                  80

Gly Gly Gly Trp Gly Gln Pro His Gly Gly Gly Trp Gly Gln Xaa Xaa
                 85                  90                  95

Xaa Xaa Xaa Xaa Xaa Xaa Gly Gly Thr His Ser Gln Trp Asn Lys
            100                 105                 110

Pro Ser Lys Pro Lys Thr Asn Met Lys His Met Ala Gly Ala Ala Ala
            115                 120                 125

Ala Gly Ala Val Val Gly Gly Leu Gly Gly Tyr Met Leu Gly Ser Ala
            130                 135                 140
```

-continued

```
Met Ser Arg Pro Ile Ile His Phe Gly Ser Asp Tyr Glu Asp Arg Tyr
145                 150                 155                 160

Tyr Arg Glu Asn Met His Arg Tyr Pro Asn Gln Val Tyr Tyr Arg Pro
            165                 170                 175

Met Asp Glu Tyr Ser Asn Gln Asn Asn Phe Val His Asp Cys Val Asn
        180                 185                 190

Ile Thr Ile Lys Gln His Thr Val Thr Thr Thr Lys Gly Glu Asn
    195                 200                 205

Phe Thr Glu Thr Asp Val Lys Met Met Glu Arg Val Val Glu Gln Met
210                 215                 220

Cys Ile Thr Gln Tyr Glu Arg Glu Ser Gln Ala Tyr Tyr Gln Arg Gly
225                 230                 235                 240

Ser Ser Met Val Leu Phe Ser Ser Pro Val Ile Leu Leu Ile Ser
            245                 250                 255

Phe Leu Ile Phe Leu Ile Val Gly Xaa
            260                 265

<210> SEQ ID NO 23
<211> LENGTH: 265
<212> TYPE: PRT
<213> ORGANISM: Homo sapiens
<220> FEATURE:
<221> NAME/KEY: misc_feature
<222> LOCATION: (95)..(102)
<223> OTHER INFORMATION: Xaa can be any naturally occurring amino acid
<220> FEATURE:
<221> NAME/KEY: misc_feature
<222> LOCATION: (265)..(265)
<223> OTHER INFORMATION: Xaa can be any naturally occurring amino acid

<400> SEQUENCE: 23

Met Ala Asn Ser His Leu Gly Cys Trp Met Leu Val Leu Phe Val Ala
1               5                   10                  15

Thr Trp Ser Asp Leu Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Xaa Xaa
                85                  90                  95

Xaa Xaa Xaa Xaa Xaa Xaa Gly Gly Gly Thr His Ser Gln Trp Asn Lys
            100                 105                 110

Leu Ser Lys Ile Lys Thr Asn Met Lys His Met Ala Gly Ala Ala Val
        115                 120                 125

Ala Gly Ala Val Val Gly Gly Leu Gly Gly Tyr Val Leu Val Ser Ala
    130                 135                 140

Met Ser Arg Pro Met Ile His Phe Ser Ser Asp Tyr Glu Asp Arg Tyr
145                 150                 155                 160

Tyr Arg Glu Asn Met His Arg Tyr Pro Asn Gln Val Tyr Tyr Arg Pro
            165                 170                 175

Met Asp Glu Tyr Ser Ser Gln Asn Asn Phe Val His Asn Cys Ile Asn
        180                 185                 190

Ile Thr Val Lys Gln Arg Gly Val Thr Thr Thr Lys Gly Lys Asn
    195                 200                 205
```

```
Ser Thr Lys Thr Asn Ile Lys Met Met Glu His Val Ile Gln Pro Met
    210                 215                 220
Cys Ile Thr Arg Tyr Lys Arg Glu Ser Gln Ala Tyr Tyr Gln Arg Gly
225                 230                 235                 240
Ser Ser Arg Val Leu Phe Ser Ser Ser Pro Val Ile Leu Leu Ile Ser
                245                 250                 255
Phe Leu Ile Phe Leu Ile Val Gly Xaa
            260                 265

<210> SEQ ID NO 24
<211> LENGTH: 20
<212> TYPE: PRT
<213> ORGANISM: Bos taurus

<400> SEQUENCE: 24

Cys Ala Thr Ala Thr Gly Ala Thr Gly Cys Thr Gly Ala Cys Ala Cys
1               5                  10                  15
Cys Cys Thr Cys
            20

<210> SEQ ID NO 25
<211> LENGTH: 22
<212> TYPE: PRT
<213> ORGANISM: Bos taurus

<400> SEQUENCE: 25

Ala Gly Ala Ala Gly Ala Thr Ala Ala Thr Gly Ala Ala Ala Ala Cys
1               5                  10                  15
Ala Gly Gly Ala Ala Gly
            20

<210> SEQ ID NO 26
<211> LENGTH: 20
<212> TYPE: DNA
<213> ORGANISM: Bos taurus

<400> SEQUENCE: 26
catatgatgc tgacaccctc                                           20

<210> SEQ ID NO 27
<211> LENGTH: 22
<212> TYPE: DNA
<213> ORGANISM: Bos taurus

<400> SEQUENCE: 27
agaagataat gaaaacagga ag                                        22
```

POLYMORPHISM IN BOVINE PRION PROTEIN GENE SEQUENCE

CROSS-REFERENCE TO RELATED APPLICATION

This application hereby claims the benefit of U.S. provisional application 60/793,760, filed Apr. 21, 2006, the content of which are incorporated by reference herein.

BACKGROUND OF THE INVENTION

1. Field of the Invention

The invention relates to a method for detecting genetic variations in bovine which influence their susceptibility to bovine spongiform encephalopathy.

Transmissible spongiform encephalopathy (TSE) agents or prions induce fatal neurodegenerative diseases in humans and in other mammalian species. They are transmissible among their species of origin, but they can also cross the species barrier and induce infection and/or disease in other species. Human TSEs include Creutzfeldt-Jakob disease (CJD), Gerstmann-Sträussler-Scheinker syndrome, Kuru and fatal familial insomnia (36). In animals, 4 distinct TSE diseases are recognized: scrapie in sheep and goats, transmissible mink encephalopathy (TME) in mink, chronic wasting disease (CWD) in cervids, and bovine spongiform encephalopathy (BSE) in cattle. BSE was transmitted via BSE-contaminated feed to cats (feline spongiform encephalopathy, FSE) and exotic ungulates (exotic ungulate encephalopathy, EUE) and via contaminated food to humans (48, 49, Smith et al., 2004. CTMI 284: 161). BSE first emerged in the United Kingdom in 1986, and has subsequently spread to many countries, predominantly in Western Europe. These outbreaks, caused by the consumption of infected meat and bone meal containing a malformed protein, have resulted in the destruction of thousands of cattle and have caused significant economic losses.

2. Description of the Prior Art

Prions are proteinaceous infectious particles and are the causative agents of TSEs. They are host coded proteins that have undergone conformational changes and have biological and physicochemical characteristics that differ significantly from those of other infectious agents. For example, they are resistant to inactivation processes that are effective against conventional viruses including those that alter nucleic acid structure or function. These include ionizing and UV radiation (1) or inactivation by formalin (20). In addition, infectivity is highly susceptible to procedures that modify protein conformation. Protein denaturants are effective at reducing infectivity titers but complete inactivation requires extremely harsh conditions, such as up to 4 hours of autoclaving at 134° C. or treatment with 2 N NaOH (39). In TSE disease, the normal cellular protein, $PrP^C$, is converted to abnormal prion protein, $PrP^{Sc}$. $PrP^{Sc}$ exhibits increased beta sheet content, a change that may drive the additional changes in solubility and protease resistance (38). Unlike normal cellular protein, $PrP^{Sc}$ is relatively insoluble in detergents, is relatively resistant to proteases (37) and is capable of causing a conformational change in additional molecules of $PrP^c$. The precise function of the normal $PrP^c$ in healthy animals remains unknown. $PrP^c$ might play a role in sleep physiology, in resistance to oxidative stress, in signal transduction and in self-renewal of hematopoietic stem cells (16, 29, 31, 53).

TSE disease involves the accumulation of $PrP^{Sc}$ in the central nervous system (CNS) of the host, eventually leading to neurodegeneration and disease. In TSE-affected animals, $PrP^c$ has a determinant role in the incubation time and species barrier (8). Transgenic mice lacking prion protein gene (Prnp) expression are not susceptible to TSE agents or prion infection, demonstrating the key role of PrP in TSEs (8). Susceptibility to prions thus depends upon the presence of $PrP^c$ on the cell membrane of the host; prions do not propagate in brains that lack $PrP^c$ (6).

Widely referred to as "mad cow disease", BSE was first identified as a TSE of cattle in the mid 1980s in the U.K. and more than 180,000 positive cases have been diagnosed in the U.K. to date. BSE is a chronic degenerative disease affecting the central nervous system of cattle. Affected animals display changes in temperament, abnormal posture, incoordination and difficulty in rising, decreased milk production, and/or loss of body weight despite continued appetite (40). The average incubation period is about 4-6 years and all affected animals succumb to the disease (28). Following the onset of clinical signs, the animal's condition deteriorates until it either dies or is destroyed. This process usually takes from 2 weeks to 6 months. Most cases in Great Britain occurred in dairy cows between 3 and 6 years of age with the highest susceptibility to infection being in the first 6 months of life; adult cattle are at relatively low risk of infection (3).

Using epidemiological surveillance programs, many European and non-European countries have discovered BSE-positive animals within the last decade (17, 34). Validated diagnostic tests for BSE require brain tissue (33, 47). There are no validated ante mortem tests for BSE available at present. The original diagnostic test method was histopathology in which sections of brain were examined under a microscope, and the classical vacuoles and spongiform changes in specific areas of the brain would allow a diagnosis (33). In the mid-1990s, immunohistochemistry (IHC) and Western blotting were developed which allowed the detection of $PrP^{sc}$ in tissues (33). Both IHC and Western blot are considered confirmatory tests for BSE by the World Organization for Animal Health-OIE (33). In the past decade, so-called "rapid tests" have been introduced commercially for BSE surveillance (33).

However despite these and other advances, the need remains for improved methods for diagnosing BSE infected animals, and particularly for detecting bovine animals having increased susceptibility to BSE.

SUMMARY OF THE INVENTION

I have now discovered a specific, non-synonymous single nucleotide polymorphism (SNP) in the gene encoding bovine prion protein (Prnp) which might affect the susceptibility of bovine animals to bovine spongiform encephalitis (BSE). The precise location of the SNP varies with the number of octapeptide repeat sequences present in the Prnp gene. The octapeptide region polymorphisms result in encoded PrP proteins of different amino acid length. There are three known sequences of the bovine Prnp gene, those with five, six or seven of the octapeptide repeat units. Although six octapeptide repeat units are present in the Prnp gene of most bovines, a relatively small number of bovine possess Prnp genes having five octapeptide repeat units, and on rare occasions, bovine possessing Prnp genes having seven octapeptide repeat units have been observed. The SNP of this invention corresponds to position 322 nucleotides downstream from last nucleotide of the 3' end of the last octapeptide repeat region of the bovine Prnp sequence. This is equivalent to a net distance of 321 nucleotides between the last nucleotide of the last octapeptide repeat region and the SNP nucleotide (occurring in the 5' to 3' direction, i.e. in the bovine Prnp gene with 6 octapeptide repeat regions [e.g., GenBank Accession no.

AJ298878, (SEQ. ID. No. 1)], the last nucleotide at the 3' end of the $6^{th}$ octapeptide repeat region is at nucleotide position 309 and the SNP mutation at nucleotide position 631) on exon 3 of the Prnp gene, wherein the nucleotide position of the SNP is measured relative to the Prnp sequence, GenBank Accession no. AJ298878, disclosed by Coulthart and coworkers (12) the contents of which are incorporated by reference herein. Thus, depending on the number of octapeptide repeat units present in the Prnp gene, the position of the SNP is either nucleotide 631 of exon 3 (codon 211) when the Prnp gene comprises six octapeptide repeat sequences, nucleotide 607 of exon 3 (codon 203) when the Prnp gene comprises five octapeptide repeat sequences, or nucleotide 655 of exon 3 (codon 219) when the Prnp gene comprises seven octapeptide repeat sequences.

Alleles of the bovine Prnp wherein the codons 203, 211 or 219, respectively, with the nucleotide Adenine (A) at the SNP position encode lysine (K) at the corresponding amino acids (i.e., 211, 203 or 219) in the bovine prion protein (PrP), are all indicative of increased susceptibility to BSE in comparison to alleles of the bovine Prnp wherein the codons 203, 211 or 219, respectively, with the nucleotide Guanine (G) at the SNP position encode glutamic acid (E) at the same position. This SNP (nucleotide position 631 in Prnp gene with 6 octapeptide repeat region according to GenBank Accession no. AJ298878) may be used as a marker for selecting bovines susceptible to BSE for disposal and/or removal from breeding.

In accordance with this discovery, it is an object of this invention to determine an SNP in the Prnp gene in bovine which effects susceptibility to BSE.

It is also an object of this invention to provide methods for identifying this SNP in the Prnp gene in bovine which effects susceptibility to BSE.

In accordance with this discovery, it is an object of this invention to provide methods for identifying bovine exhibiting the trait of increased susceptibility to BSE.

Another object of this invention is to provide methods for screening bovine to select for those animals which possess alleles of the Prnp gene that are associated with increased susceptibility to BSE.

Other objectives and advantages of this invention will become readily apparent from the ensuing description.

BRIEF DESCRIPTION OF THE DRAWINGS

Figure 1A3:
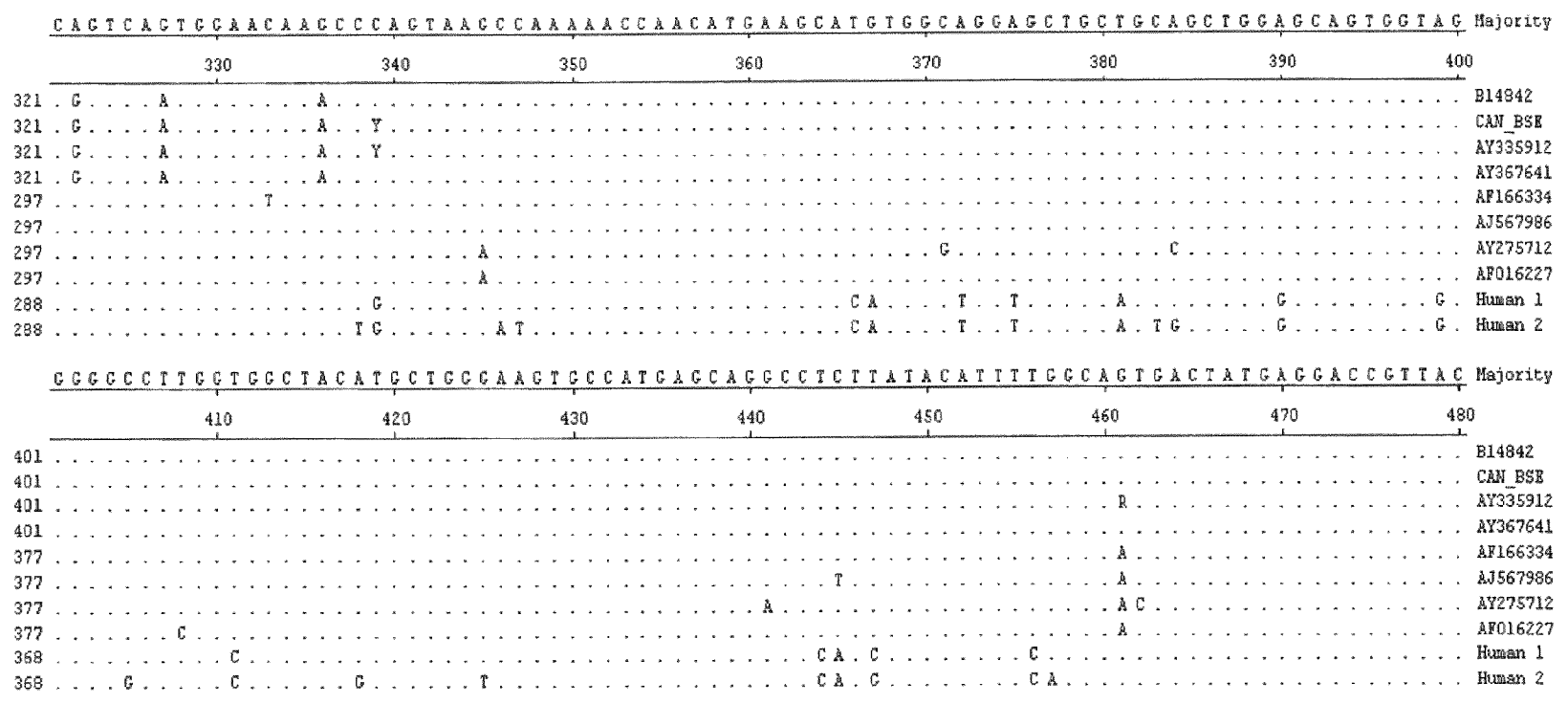
Figure 1A4:
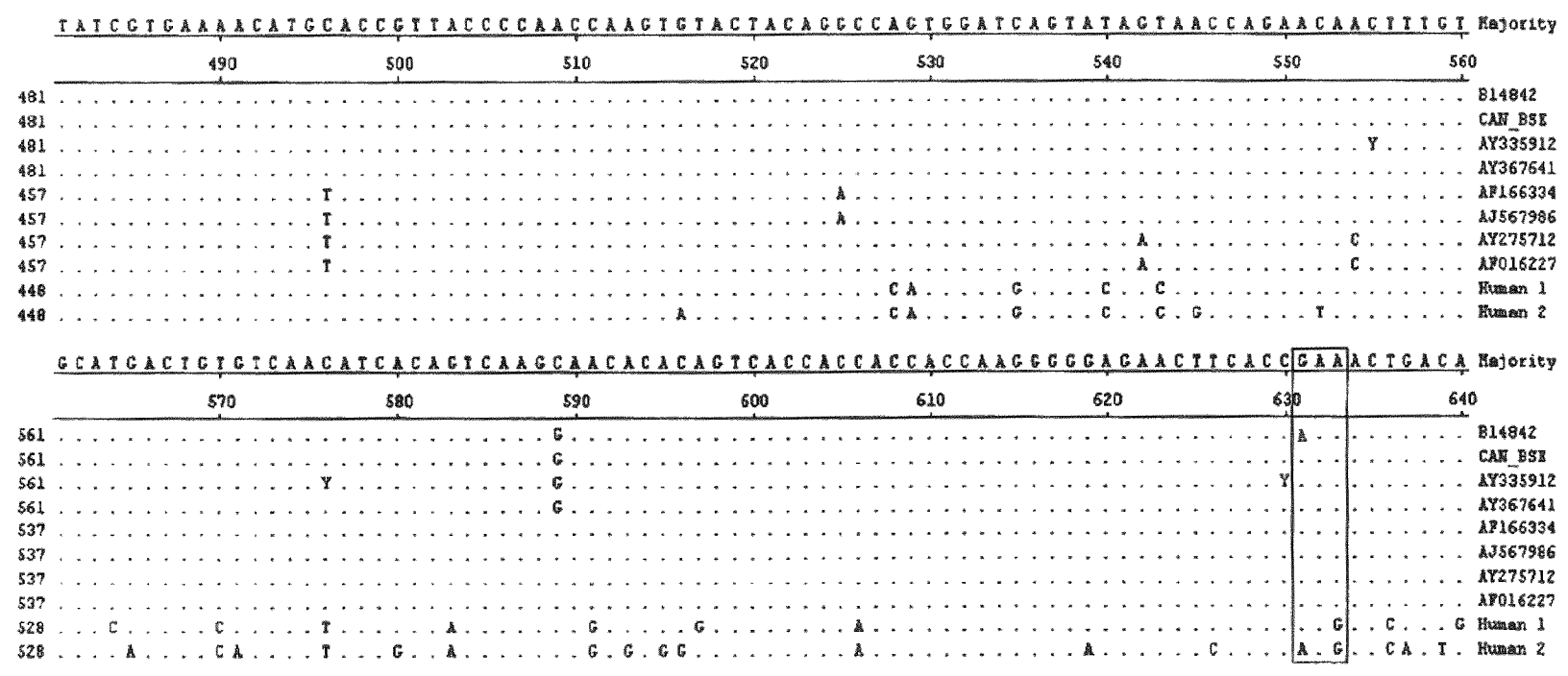
Figure 1A5:
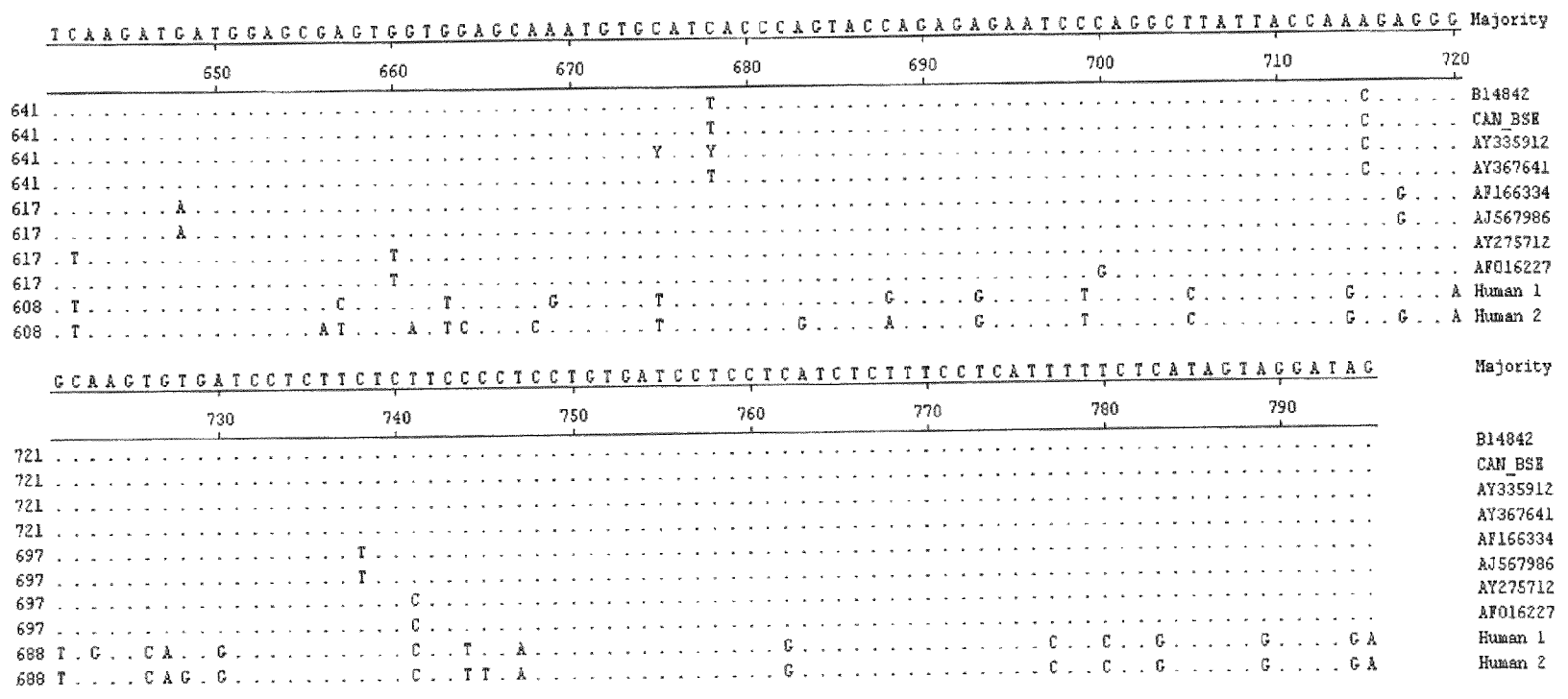

FIG. 1A shows the alignment of bovine, ovine, cervid and human Prnp nucleotide sequences including BSE case B14842 as described in Example 1 (SEQ. ID. Nos. 2-12). All bovine alleles contained six octapeptide repeat units, while the ovine, cervid and human Prnp alleles contained five octapeptide repeat units. The box enclosing nucleotides 283-306 (codons 95-102) represents the additional octapeptide-repeat region in bovine (for a total of six octapeptide repeats) which is not present in ovine and cervids. The box surrounding nucleotides represents the codon where the non-synonymous polymorphism ("G"AA/"A"AA) is located in the first position of bovine codon 211 of BSE case B14842. Standard single letter codes are used for nucleotides. Y=C or T; R=A or G; K=G or T; W=A or T.

FIG. 1B shows the amino acid sequences for the corresponding prion protein encoded by the Prnp gene sequences depicted in FIG. 1A (SEQ. ID. Nos. 13-23). Standard IUPAC single letter codes are used for amino acids. The box surrounding codon 211 represent the codon with the E211K polymorphism.

Codon numbering refers to the most common six-copy octapeptide repeat allele for Bos Taurus as described by Coulthart and coworkers (12). The following bovine, cervid, ovine and human GenBank entries were used for the alignments: BSE Case B14842, and GenBank accession numbers AY335912 (bovine: reports Prnp coding variation in a panel of 96 cattle chosen to represent most of the genetic diversity of the beef cattle breeds most commonly raised in North America), CAN_BSE=Canadian 2003 BSE case (see Coulthart et al., 2003; citation 12), AY335912 (bovine), AY367641 (bovine), AF166334 (ovine), AY275712 (white-tailed deer), and AF016227 (elk). The human sequences were derived from FIG. 1 in Coulthart et al., 2003 (12). Human 1=M13899; Human 2=PRNPvar.

DEFINITIONS

Allele: the term coined by Bateson and Saunders (1902) for characters which are alternative to one another in Mendelian inheritance (Gk. Allelon, one another; morphe, form). Now the term allele is used for two or more alternative forms of a gene resulting in different gene products and thus different phenotypes. In a haploid set of chromosomes there is only one allele at its specific locus. Diploid organisms have 2 alleles at a given locus, and if they are homozygous for a defined gene, both alleles are identical. However, if heterozygous for a defined gene they have one normal and one mutant allele. A single allele for each gene locus is inherited separately from each parent (e.g., at a locus for eye color the allele might result in blue or brown eyes). An organism is homozygous for a gene if the alleles are identical, and heterozygous if they are different. (Birgid Schlindwein's Hypermedia Glossary of Genetic Terms).

Amplicon: a term to define the amplification product generated by the polymerase chain reaction. The physical boundaries of an amplicon extend to the base sequence at the 5' ends of each of a pair of primers (short, 18-20 oligonucleotides) in the reaction.

Centimomorgan (cM): a unit to measure the recombination frequency. One centimorgan is equal to a 1% chance that a marker at one genetic locus will be separated from a marker at a second locus due to crossing over in a single generation. In human beings, 1 centimorgan is equivalent, on average, to 1 million base pairs. (Birgid Schlindwein's Hypermedia Glossary of Genetic Terms).

Crossing over: the term coined by Morgan and Cattell (1912) for the occurrence of new combinations of linked characters. With the acceptance of the chromosome theory, the term is applied to the breaking during meiosis of one maternal and one paternal chromosome, the exchange of corresponding sections of DNA, and the rejoining of the chromosomes. This process can result in an exchange of alleles between chromosomes and gives rise to new character combinations. (Birgid Schlindwein's Hypermedia Glossary of Genetic Terms).

DNA or RNA sequence: a linear series of nucleotides connected one to the other by phosphodiester bonds between the 3' and 5' carbons of adjacent pentoses.

Genotype: the term proposed by Johannsen (1909) for the hereditary constitution of an individual, or of particular nuclei within its cells. (Birgid Schlindwein's Hypermedia Glossary of Genetic Terms).

Identity by descent: two alleles at a single locus are identical by descent if there are identical copies of the same allele in some earlier generation, i.e., both are copies that arose by DNA replication from the same ancestral sequence without any intervening mutation. The animal is homozygous for this defined locus.

Identity by type: two alleles at a single locus are identical by type, (i.e. "the same") if they have the same phenotypic effects.

Locus: the position of a gene on a chromosome or other chromosome markers; also, the DNA at that position. The use of the term locus is sometimes restricted to main regions of DNA that are expressed. (Birgid Schlindwein's Hypermedia Glossary of Genetic Terms).

Marker: an identifiable physical location on a chromosome (e.g., restriction enzyme cutting site, gene, minisatellite, microsatellite) whose inheritance can be monitored. Markers can be expressed regions of DNA (genes) or some segment of DNA with no known coding function but whose pattern of inheritance can be determined. (Birgid Schlindwein's Hypermedia Glossary of Genetic Terms).

Nucleic acid: a deoxyribonucleotide or ribonucleotide polymer in either single- or double-stranded form, including known analogs of natural nucleotides unless otherwise indicated.

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C") and thymine ("T"). The four RNA bases are A, G, C and uracil ("U").

Oligonucleotide: a single-stranded nucleic acid ranging in length from 2 to about 500 bases, usually 2-100 bases.

Phenotype: the term coined by Johannsen (1909) for the appearance (Gk. phainein, to appear) of an organism with respect to a particular character or group of characters (physical, biochemical, and physiologic), as a result of the interaction of its genotype and its environment. Often used to define the consequences of a particular mutation. (Birgid Schlindwein's Hypermedia Glossary of Genetic Terms).

Polymorphic marker or site: the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms (U.S. Pat. No. 6,368,799).

Probe: a DNA fragment or an oligonucleotide capable of binding to a target nucleic acid of complementary sequence through one or more types of chemical bonds, by hybridization or complementary base pairing, usually through hydrogen bond formation. Oligonucleotides probes are often 10-50 or 15-30 bases long. An oligonucleotide probe may include natural (i.e. A, G, C, or T) or modified bases (7-deazaguanosine, inosine, etc.).

Recombination: the process by which progeny derive a combination of linked genes different from that of either parent. In higher organisms, this can occur by crossing over between their loci during meiosis. Recombination may come about through random orientation of non-homologous chromosome pairs on the meiotic spindles, from crossing-over between homologous chromosomes, from gene conversion, or by other means. (Birgid Schlindwein's Hypermedia Glossary of Genetic Terms).

Single nucleotide polymorphism (SNP): occurrence of a polymorphic site occupied by a single nucleotide, constituting the site of variation between allelic sequences. The site is usually preceded by and followed by highly conserved sequences of the allele (e.g., sequences that vary in less than $1/100$ or $1/1000$ members of the populations). A single nucleotide polymorphism usually arises due to substitution of one nucleotide for another at the polymorphic site.

Specific hybridization: binding, duplexing, or hybridizing of a molecule only to a particular nucleotide sequence under stringent conditions such that the probe will hybridize to its target subsequence, but not to other sequences. Stringent conditions are sequence-dependent and are different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. Typically, stringent conditions include a salt concentration of at least about 0.01 to 1.0 M Na ion concentration (or other salts) at pH 7.0 to 8.3 and the temperature is at least about 30° C. for short probes (e.g., 10 to 50 nucleotides). Stringent conditions can also be achieved with the addition of destabilizing agents such as formamide. For example, conditions of 5×SSPE (750 mM NaCl, 50 mM NaPhosphate, 5 mM EDTA, pH 7.4) and a temperature of 25-30° C. are suitable for allele-specific probe hybridizations. A perfectly matched probe has a sequence perfectly complementary to a particular target sequence (U.S. Pat. No. 6,368,799).

Transition: the term proposed by Freese (1959) for a mutation caused by the substitution in DNA or RNA of one purine by the other, and similarly with the pyrimidines. (Birgid Schlindwein's Hypermedia Glossary of Genetic Terms).

Transversion: the term proposed by Freese (1959) for a mutation caused by the substitution of a purine for a pyrimidine, and vice versa, in DNA or RNA. (Birgid Schlindwein's Hypermedia Glossary of Genetic Terms).

DETAILED DESCRIPTION OF THE INVENTION

The entire exon 3 (coding region for the bovine prion protein) of the bovine PrnP gene was amplified by PCR from animal B14842 and has been sequenced. The nucleotide sequence and the corresponding amino acid sequence are shown in SEQ. ID. Nos. 3 and 14.

Prion protein gene alleles containing a variety of polymorphisms have been associated with increased susceptibility to TSE in sheep and humans (28A, 32A). However, to date, polymorphisms effecting susceptibility to BSE have not been identified in exon 3, the coding region of bovine Prnp. So far, only certain polymorphisms described in the promoter region of the bovine Prnp gene have been associated with increased or reduced susceptibility to BSE (12, 23, 41). Upon Prnp gene sequence analysis of a recently diagnosed BSE case, designated animal B14842, I have discovered a previously unknown non-synonymous polymorphism within the Prnp gene coding sequence from this animal. One Prnp gene allele of the animal contained an SNP-designated E211K (GAA/AAA) at nucleotides 631-633 (codon 211) in the 6 octapeptide repeat region containing bovine Prnp gene as described by Coulthart and coworkers (12). As previously described in the art, normal bovine possess coding sequences for the Prnp gene which include six octapeptide repeat regions and guanine at position 631. The resultant 211 codon is GAA, encoding glutamic acid (E) at amino acid 211 of the prion protein. However, the BSE positive B14842 animal possessed an SNP at position 631 substituting adenine for guanine, and the Prnp gene codon 211 is AAA and consequently encodes the basic amino acid lysine (K) rather than the acidic amino acid glutamic acid (E).

It is believed that the presence of this SNP is associated with a case of genetic BSE in bovine B14842 and older animals carrying this SNP and such a SNP may increase the susceptibility of younger animals to BSE. Moreover, while a polymorphism for codon 211 has not been previously described for the bovine Prnp gene, a non-synonymous polymorphism at the corresponding codon 200 in the human Prnp gene (E200K; GAG/AAG) is well known. This E200K mutation has been shown to lead to genetic TSE's in humans (>50% of individuals carrying the E200K polymorphism develop a human genetic TSE when advanced in age (see review by Kovacs et al., 2005; 28A), and is the most common mutation in human patients with genetic Creutzfeldt-Jakob disease (gCJD), fatal familial insomnia (FFI), and Gerstmann-Straussler-Scheinker (GSS) disease (28A). Considering that the human Prnp gene possesses only five octapeptide repeat units vs. the typical six in the bovine (and also in the B14842 animal) Prnp gene, and that the human Prnp gene has three codon deletions in its N-terminus as compared to the bovine Prnp, the E211K SNP of the invention is homologous to the E200K SNP described for the human Prnp gene. This finding indicates that genetic BSE or gBSE could exist in cattle similar to the genetic prion diseases or gTSE described in humans (28A).

While the SNP of this invention was discovered in a bovine possessing a Prnp gene having the typical six octapeptide metal-binding repeat units, there are two other known bovine Prnp gene sequences with five and seven of the octapeptide repeats. Thus, depending on the number of octapeptide repeat units present in the Prnp gene, the position of the SNP is either nucleotide 631 of exon 3 (codon 211) when the Prnp gene comprises six octapeptide repeat sequences, nucleotide 607 of exon 3 (codon 203) when the Prnp gene comprises five octapeptide repeat sequences, or nucleotide 655 of exon 3 (codon 219) when the Prnp gene comprises seven octapeptide repeat sequences. Because the SNP exists at homologous codon positions in the bovine Prnp gene, the SNP may be described relative to the position of the last octapeptide repeat nucleotide (measured from the 5' to 3' direction) on exon 3 of the Prnp gene. In the bovine Prnp gene with 6 octapeptide repeat regions (GenBank Accession no. AJ298878), the last nucleotide at the 3' end of the $6^{th}$ octapeptide repeat region is at nucleotide position 309 and the SNP mutation at nucleotide position 631 on exon 3 of the Prnp gene. The nucleotide position of the SNP is measured relative to the Prnp sequence, GenBank Accession no. AJ298878, disclosed by Coulthart and coworkers (12) the contents of which are incorporated by reference herein. In bovine possessing a Prnp gene having five, six or seven octapeptide repeat units on exon 3, the last (i.e., on the 3' end) nucleotide of the last ($5^{th}$, $6^{th}$ or $7^{th}$) octapeptide repeat region sequence is at nucleotide position 285, 309, and 333, respectively. Consequently, the SNP of this invention corresponds to a position 322 nucleotides downstream from this nucleotide at the 3' end of the last octapeptide repeat sequence. For the purposes of this invention, it is understood that the nucleotide position of the final 3' nucleotide of the last octapeptide repeat region ($5^{th}$, $6^{th}$ or $7^{th}$), and thus the nucleotide position of the SNP, is measured relative to the Prnp sequence, GenBank Accession no. AJ298878, disclosed by Coulthart and coworkers (12). It is also understood that animals which are either heterozygous or homozygous for the SNP of this invention (the E211K mutation) may exhibit increased susceptibility to BSE.

This invention is also drawn to a method for determining alleles of the bovine Prnp gene encoding prion protein (the amino acid sequence of which is shown in FIG. 1B) which affects the susceptibility of bovines to BSE. In accordance with this method, a sample of nucleic acids from a bovine is assayed to determine the nucleotides present at the SNP in the Prnp gene which is disclosed herein. As noted above, the position of the SNP is either nucleotide 631 of exon 3 (codon 211) when the Prnp gene comprises six octapeptide repeat region sequences, nucleotide 607 of exon 3 (codon 203) when the Prnp gene comprises five octapeptide repeat region sequences, or nucleotide 655 of exon 3 (codon 219) when the Prnp gene comprises seven octapeptide repeat region sequences.

Because the polymorphism occurs at homologous codons on the Prnp gene, the codon containing the SNP may encode either glutamic acid (E) or lysine (A) at the corresponding amino acids 203, 211 or 219 of the bovine prion protein (for prion protein encoded by Prnp genes having five, six or seven octapeptide repeat units, respectively). Specifically, the above-mentioned SNP at positions 607, 631 or 655 may be guanine, yielding a "G"AA codon encoding glutamic acid (E), or the SNP may be adenine, yielding an "A"AA codon encoding lysine (K). It is believed that alleles of the bovine Prnp wherein the SNP at these positions encode lysine at the corresponding amino acids (i.e., 211, 203 or 219) in the bovine prion protein, are all associated with increased susceptibility to BSE in comparison to alleles which encode glutamic acid (E) at the same position (as the latter is typically present in normal, healthy bovine). This SNP may be used as a marker for selecting bovines with a higher susceptibility to BSE for disposal and/or removal from breeding.

The SNP's may be detected by assaying for the presence of the above-mentioned nucleotides in a sample of nucleic acids from a subject bovine animal at the loci of the SNP, wherein the loci correspond to nucleotide 631 of exon 3 (codon 211) when the Prnp gene comprises six octapeptide repeat sequences, nucleotide 607 of exon 3 (codon 203) when the Prnp gene comprises five octapeptide repeat sequences, or nucleotide 655 of exon 3 (codon 219) when the Prnp gene comprises seven octapeptide repeat sequences. Suitable nucleic acids for use in the assay include genomic DNA, cDNA, or RNA, as well as nucleic acids that encompass, or are encompassed by the bovine Prnp gene sequences of FIG. 1 or the complement thereof, as well as bovine Prnp gene sequences which are the same as in FIG. 1 except for the presence of five or seven octapeptide repeat sequences or their complement. AS will be described in greater detail herein below, use of genomic DNA is preferred.

It is also envisioned that the SNP may also be detected by analysis of the encoded gene product, i.e., the amino acid sequence of prion protein in a sample obtained from the subject animal. Sample materials which may be collected from the animal for the assay include, but are not limited to, milk, blood, tissue, cells, urine, or other biological samples from the subject such as described by Novakofski et al (32A, the contents of which are incorporated by reference herein).

The presence of the allelic forms of the above-described SNP can be determined by any of a number of diagnostic assays. These assays may use otherwise known techniques, including direct sequencing of the nucleic acids in the sample, or using probes which overlap the position of the SNP's on those nucleic acids. For example, Arnold et al. (U.S. Pat. No. 6,410,231, herein incorporated by reference) is drawn to SNP detection by means of an array-based sandwich assay. Arnold et al. also makes mention of a variety of other techniques that had been previously developed for SNP detection and analysis; specifically: Sapolsky et al. (1999) U.S. Pat. No. 5,858, 659; Shuber (1997) U.S. Pat. No. 5,633,134; Dahlberg (1998) U.S. Pat. No. 5,719,028; Murigneux (1998) WO 98/30717; Shuber (1997) WO 97/10366; Murphy et al. (1998) WO 98/44157; Lander et al. (1998) WO 98/20165; Goelet et al. (1995) WO 95/12607 and Cronin et al. (1998) WO 98/30883. In addition, ligase based methods are described by Barany et al. (1997) WO 97/31256 and Chen et al. Genome Res. 1998; 8(5):549-556; mass-spectroscopy-based methods by Monforte (1998) WO 98/12355, Turano et al. (1998) WO 98/14616 and Ross et al. (1997) Anal. Chem. 15:4197-4202; PCR-based methods by Hauser, et al. (1998) Plant J. 16:117-125; exonuclease-based methods by Mundy U.S. Pat. No. 4,656,127; dideoxynucleotide-based methods by Cohen et al. WO 91/02087; Genetic Bit Analysis or GBA™ by Goelet et al. WO 92/15712; Oligonucleotide Ligation Assays or OLAs by Landegren et al. (1988) Science 241:1077-1080 and Nickerson et al. (1990) Proc. Natl. Acad. Sci. (USA) 87:8923-8927; and primer-guided nucleotide incorporation procedures by Prezant et al. (1992) Hum. Mutat. 1:159-164; Ugozzoli et al. (1992) GATA 9:107-112; Nyreen et al. (1993) Anal. Biochem. 208:171-175, all of which are incorporated herein by reference. Other potential assay techniques are described below. McCutchen-Maloney (U.S. Pat. No. 6,340, 566, herein incorporated by reference) teaches detection and quantification of SNP's, DNA sequence variations, DNA mutations, DNA damage and DNA mismatches using mutation binding proteins alone or as chimeric proteins with nucleases on solid supports. Also, Poponin (U.S. Pat. No. 6,376,177, herein incorporated by reference) teaches a method and apparatus for SNP detection by means of spectroscopic analysis of hybridized nucleic acid using high density nucleic acid chips. Numerous conventional assay techniques for detecting SNP's which are also suitable for use herein are described by Aguirre et al. (U.S. Pat. No. 6,428, 958) and Rothenberg (U.S. Pat. No. 6,355,425). The contents of each of the above-mentioned publications and patents are incorporated by reference herein.

In accordance with one preferred embodiment, the presence of the SNP is detected by PCR amplification as described in Example 1. It is envisioned that a variety of primers and PCR assays may be suitable for use in the amplification, including bovine Prnp specific primers disclosed by Heaton et al. (23), Sander et al. (41) or Coulthart et al (12), the contents of which are incorporated by reference herein. However, in a preferred embodiment, at least one of the primers is designed to hybridize to a region of the gene outside of exon 3, such as an intron (here intron 2). Although not reported in bovine to date, the recent disclosure of pseudogenes in cervidae (32A) raises the specter of their possible presence in genomes of other animals as well, including bovine. Because pseudogenes are non-functional, but heritable, genes believed to have been generated by reverse transcription of mRNA from previous generations of the species, they may have different nucleotide sequences than the corresponding functional gene in the subject animal of interest. Consequently, if pseudogenes are present, the possibility exists that primers generated strictly from the exons of a gene of interest may in fact be selective for the pseudogene rather than the active gene. To guard against the possible presence of any such pseudogenes, at least one of the primers used herein is preferably generated to bind to a region of the gene outside of the coding sequence of the genomic DNA, such an intron. In accordance with this embodiment, preferred primers for use herein include, but are not limited to 5'-CATATGATGCTGACACCCTC-3' (SEQ. ID. No. 24) and 5'-AGAAGATAATGAAAACAGGAAG-3 (SEQ. ID. No. 25), wherein the first primer is the intron 2-specific forward primer, and the second primer is the exon 3-specific reverse primer.

The presence of the SNP on exon 3 of the Prnp gene may also be detected by assaying for the same nucleotides described above at the loci corresponding to nucleotide 631 of exon 3 (codon 211) when the Prnp gene comprises six octapeptide repeat sequences, nucleotide 607 of exon 3 (codon 203) when the Prnp gene comprises five octapeptide repeat sequences, or nucleotide 655 of exon 3 (codon 219) when the Prnp gene comprises seven octapeptide repeat sequences, in an RNA molecule which is a transcript of a sequence encompassed by, or encompassing, the complementary strand to the bovine Prnp gene such as shown in FIG. 1. Alternatively, any of the SNP's may be detected in the DNA strand complementary to the sequence shown in FIG. 1 by assaying for the complementary nucleotides at the loci corresponding to position nucleotide 631 of exon 3 (codon 211) when the Prnp gene comprises six octapeptide repeat sequences, nucleotide 607 of exon 3 (codon 203) when the Prnp gene comprises five octapeptide repeat sequences, or nucleotide 655 of exon 3 (codon 219) when the Prnp gene comprises seven octapeptide repeat sequences.

As noted above, the SNP of the bovine Prnp gene may also be detected by analysis of the prion protein product. In bovine possessing a prion protein having five, six or seven octapeptide repeat units, the last (i.e., C-terminal) amino acid of the last (C-terminal) octapeptide region is at position 95, 103, and 111, respectively. Consequently, the SNP of this invention corresponds to a position 108 amino acids downstream from this amino acid at the C-terminal end of the last octapeptide repeat sequence. Again, for the purposes of this invention, it is understood that the amino acid position of the final C-terminal amino acid of the final C-terminal octapeptide region, and thus the amino acid position of the SNP, is measured relative to the prion protein sequence encoded by the Prnp sequence, GenBank Accession no. AJ298878, disclosed by Coulthart, 12. For example, the glutamic acid/lysine (E/K) amino acid substitution caused by the SNP at the above-identified positions may be identified by contacting the biological samples with immunolabeling agents, such as monoclonal or polyclonal antibodies, raised against the variant protein (i.e., the protein resulting from the Prnp gene with the aforementioned glutamic acid/lysine substitutions). Such antibodies may be obtained using standard techniques and may be polyclonal or monoclonal. Polyclonal antibodies can be obtained, for example, by the methods described in Ghose et al. (Methods in Enzymology. Vol. 93:326-327, 1983). A prion protein polypeptide, or an antigenic fragment thereof, is used as an immunogen to stimulate the production of prion protein reactive polyclonal antibodies in the antisera of animals such as rabbits, goats, sheep, rodents and the like. Anti-prion protein antibodies specific for Prnp gene products are raised by immunizing animals with a polypeptide spanning site of the variation (i.e., amino acids 203, 211 and/or 219). Monoclonal antibodies may be obtained by the process described by Milstein and Kohler (1975. Nature. 256:495-497) or as modified by Gerhard (Monoclonal Antibodies. Plenum Press. 1980. pages 370-371). Hybridomas are screened to identify those producing antibodies that are highly specific for the selected prion protein immunogen, which is characteristic of increased or decreased susceptibility to BSE, i.e. specific for the E or K allele of the bovine Prnp gene.

Antibody binding may also be detected using known methods. For example, an ELISA assay utilizing a substrate (e.g., a plastic dish) coated with antigen comprising a bovine-derived biological sample containing the Prnp gene product. An antibody preparation specific for a known Prnp gene product is added to the well, whereupon the antibody will bind or fail to bind to the sample in the well. Non-binding material is washed away and a marker enzyme (e.g., horse radish peroxidase or alkaline phosphatase, coupled to a second antibody directed against the antigen-specific primary antibody) is added in excess and the nonadherent material is washed away. An enzyme substrate is added to the well and the enzyme catalyzed conversion is monitored as indicative of presence of the variant.

The SNP in the bovine Prnp gene of this invention may be used as a marker for identifying bovine animals having increased or reduced susceptibility to BSE. In a preferred embodiment, the SNP is used as a marker to select for cattle having the alleles associated with increased susceptibility to BSE (encoding lysine), and such animals would not be selected for breeding, may be prevented from use in the preparation of animal feed or human food products, and/or may be destroyed. In contrast, bovine possessing the SNP encoding glutamic acid may be selected for use in breeding programs to produce progeny which will also exhibit reduced susceptibility to BSE. While it is envisioned that the invention may be practiced with any species of Bovidae, and particularly any species of the genus *Bos*, it is preferably practiced with *Bos taurus* and *Bos indicus*, and particularly bulls, cows or calves.

The following examples are intended only to further illustrate the invention and are not intended to limit the scope of the invention which is defined by the claims.

Example 1

This example describes the identification and characterization of a recently diagnosed BSE case, bovine animal no. B14842. Western Blot analyses by the USDA-Agricultural Research Service-National Animal Disease Center confirmed that this animal was BSE positive.

Material and Methods

Animals and tissues. Brainstem tissue samples were taken from a bovine, animal no. B14842, suspected to be infected with BSE according to the USDA BSE surveillance plan.

Frozen samples from the medulla oblongata (obex) were available for analysis.

Western Blot Analyses. Brain homogenates from this BSE case were prepared and analyzed using the OIE-recommended Scrapie Associated Fibril (SAF)-Immunoblot method with minor modifications. This method enriches brain samples for PrP$^{Sc}$ by ultracentrifugation prior to loading them onto a SDS-PAGE gel. The SDS-PAGE electrophoresis conditions, subsequent transfer and immunodetection of PrP$^{res}$ were carried out as described elsewhere (Hamir et al, 2006. Vet Pathol. 43: 118-126). Therefore, only the enrichment method will be described in more detail. Material for analysis was taken from the brainstem area and cut into small pieces with a new razor blade after removal of dura mater. A 10% (w/v) tissue homogenate in 10 mM Tris, pH 7.5, containing 5 mM MgCl$_2$ was prepared using a homogenizer with a disposable probe (5 times, 30 sec). The homogenate was mixed well and then again sonicated for 30 seconds on ice bath (5-10 times). Benzonase® was added to the mixture for a final concentration of 100 Units/ml and incubated for 1 h at 37° C. while shaking. An equal volume of 20% (w/v) N-Lauroylsarcosine[m] in 10 mM Tris, pH 7.5 and 1 mM DTT was added to each homogenate, vortexed for 1 min every 10 min for a total of 30 min at room temperature. Homogenates were transferred to polyallomer tubes and centrifuged at 20,000×g for 25 min at 10° C. Supernatant was centrifuged again using polyallomer tubes[n] at 200,000×g for 55 min at 10° C. The resultant supernatant was discarded, the pellet was resuspend in sterile, distilled H$_2$O (1 μl per mg tissue equivalent) and sonicated until suspended. Sample was split into two aliquots into microcentrifuge tubes and one sample was treated with PK (concentration 0.4 Units/ml) by incubation at 37° C. for 60 min with agitation while the control sample was not treated with PK. Phenylmethylsulphonyl fluoride (PMSF) was added to a final concentration of 5 mM, incubated on ice for 15 min and transferred to a new 1.5 ml ultracentrifuge tube. Volume was brought up to 500 μl with H$_2$O and centrifuged at 200,000×g for 1 hr at 10° C. Pellet was resuspended in SDS-PAGE sample buffer to at least 10 mg tissue equivalent per μl. Samples were sonicated on wet ice before loading on SDS-PAGE gel. For both Western Blot techniques, detection was performed either on Biomax films or scanned images were obtained with a Typhoon imaging system.

DNA isolation and PCR amplification. Genomic DNA was extracted from 200 μl of a 10% brain homogenate using the DNAEASY tissue kit (Qiagen) according to the manufacturer's instructions. PCR was performed in a 100 μl final reaction volume containing 0.2 pmole of forward primer (5'-CAT ATG ATG CTG ACA CCC TC-3') (SEQ. ID No. 26), 0.2 pmol of reverse primer (5'-AGA AGA TAA TGA AAA CAG GAA G-3') (SEQ. ID No. 27) 1× Easy-A PCR buffer, 2.5 mM MgCl$_2$, 0.8 mM each deoxyribonucleotide triphosphate (dNTP Master Mix, 2.5 U of EASY A high-fidelity cloning Taq DNA polymerase, and 0.4 ug of total DNA. Amplification was performed with the following conditions: 94° C. for 5 min, followed by 30 Cycles of 94° C. for 30 sec (denaturation), 59° C. for 30 sec (annealing), and 72° C. for 1 min. A final extension step at 72° C. was performed for 10 minutes. Amplified DNA product was purified using a GENECLEAN spin kit[u] and sequencing was performed using the ABI 3700 DNA sequencer with a cycle sequencing kit. The fragment was sequenced in duplicate using the original two primers and two internal primers 4142 and 9612 for a total of 8 reactions. Databases were searched using standard nucleotide-nucleotide BLAST at the National Center for Biotechnology Information Web Site. The database is a collection of sequences from several sources, including GenBank and Reference Sequence. The nucleotide sequence of the BSE case was aligned using both CLUSTAL V[24,25] and CLUSTAL W[46] with the following GENBANK accession numbers: AY335912 (bovine), AY367641 (bovine), AF016227 (elk), AY275712 (white-tailed deer), AF166334 (ovine), and the Canadian BSE case using Lasergene version 5.07 software (DNASTAR-Madison, Wis.).

Results

Western Blot Analysis

Western blot analysis of brainstem homogenate of the BSE case revealed a definite positive reaction. All three isoforms of PrP$^{Sc}$ were definitely present at the milligram brain tissue equivalent tested.

Analysis of the Prnp

In order to confirm the material from the BSE case was derived from cattle and to determine whether the BSE case of the affected animals might be associated with a spontaneous germline mutation, the full coding sequence from exon 3 of the Prnp was amplified and aligned with known PrP sequences from cattle, sheep and cervids. DNA was isolated from fresh brainstem material. The prion protein (PrP) alleles of animal B14842 were found to have two polymorphisms, a synonymous polymorphism Q78Q (CAA/CAG) at codon 78 (as described in Genbank submission AY335912), and a non-synonymous polymorphism E211K (GAA/AAA) at codon 211 and both alleles contained the six-copy octapeptide repeat region. A polymorphism for position 211 has not been described for the cattle prion protein gene so far, but a non-synonymous polymorphism at the same codon, designated codon 200 in the human prion protein gene (Prnp) has been described previously (E200K; GAG/AAG). The E200K mutation is the most common mutation in human patients with genetic Creutzfeldt-Jakob Disease (gCJD), fatal familial insomnia (FFI) and Gerstmann-Sträussler-Scheinker (GSS) disease (Kovacs et al., 2005, *Hum. Genet*, 118, 166-174).

It is understood that the foregoing detailed description is given merely by way of illustration and that modifications and variations may be made therein without departing from the spirit and scope of the invention.

REFERENCES

1 Alper T, Haig D A, Clarke M C: 1966, The exceptionally small size of the scrapie agent. Biochem Biophys Res Commun 22:278-284.
2 Anderson R M, Donnelly C A, Ferguson N M, et al.: 1996, Transmission dynamics and epidemiology of BSE in British cattle. Nature 382:779-788.
3 Arnold M E, Wilesmith J W: 2004, Estimation of the age-dependent risk of infection to BSE of dairy cattle in Great Britain. Prev Vet Med 66:35-47.
4 Baylis M, Houston F, Goldmann W, et al.: 2000, The signature of scrapie: differences in the PrP genotype profile of scrapie-affected and scrapie-free UK sheep flocks. Proc Biol Sci 267:2029-2035.
5 Biacabe A G, Laplanche J L, Ryder S, Baron T: 2004, Distinct molecular phenotypes in bovine prion diseases. EMBO Rep 5:110-115.
6 Brandner S, Isenmann S, Raeber A, et al.: 1996, Normal host prion protein necessary for scrapie-induced neurotoxicity. Nature 379:339-343.
6A Brayton K A et al.: 2004, A processed pseudogene contributes to apparent mule deer prion gene heterogeneity. Gene 326:167-173.
7 Bruce M E, Will R G, Ironside J W, et al.: 1997, Transmissions to mice indicate that 'new variant' CJD is caused by the BSE agent. Nature 389:498-501.
8 Bueler H, Aguzzi A, Sailer A, et al.: 1993, Mice devoid of PrP are resistant to scrapie. Cell 73:1339-1347.
9 Cardone F, Liu Q G, Petraroli R, et al.: 1999, Prion protein glycotype analysis in familial and sporadic Creutzfeldt-Jakob disease patients. Brain Res Bull 49:429-433.
10 Casalone C, Zanusso G, Acutis P, et al.: 2004, Identification of a second bovine amyloidotic spongiform encephalopathy: molecular similarities with sporadic Creutzfeldt-Jakob disease. Proc Natl Acad Sci USA 101:3065-3070.
11 Colchester A C, Colchester N T: 2005, The origin of bovine spongiform encephalopathy: the human prion disease hypothesis. Lancet 366:856-861.
12 Coulthart M B, Mogk R, Rancourt J M, et al.: 2003, Prion protein gene sequence of Canada's first non-imported case of bovine spongiform encephalopathy (BSE). Genome 46:1005-1009.
13 Cutlip R C, Miller J M, Lehmkuhl H D: 1997, Second passage of a US scrapie agent in cattle. J Comp Pathol 117:271-275.
14 De Bosschere H, Roels S, Vanopdenbosch E: Atypical Case of Bovine Spongiform Encephalopathy in an East-Flemish Cow in Belgium. The International Journal of Applied Research in Veterinary Medicine 2:52-55.
15 Gambetti P, Kong Q, Zou W, et al.: 2003, Sporadic and familial CJD: classification and characterisation. Br Med Bull 66:213-239.
16 Gauczynski S, Peyrin J M, Haik S, et al.: 2001, The 37-kDa/67-kDa laminin receptor acts as the cell-surface receptor for the cellular prion protein. Embo J 20:5863-5875.
17 Giovannini A, Savini L, Conte A, Fiore G L: 2005, Comparison of BSE prevalence estimates from EU countries for the period July to December 2001 to the OIE and EU GBR classifications. J Vet Med B Infect Dis Vet Public Health 52:262-271.
18 Goldmann W, Hunter N, Foster J D, et al.: 1990, Two alleles of a neural protein gene linked to scrapie in sheep. Proc Natl Acad Sci USA 87:2476-2480.
19 Goldmann W, Hunter N, Smith G, et al.: 1994, PrP genotype and agent effects in scrapie: change in allelic interaction with different isolates of agent in sheep, a natural host of scrapie. J Gen Virol 75 (Pt 5):989-995.
20 Gordon W S: 1946, Advances in Veterinary Research. Veterinary Research 58:516-520.
21 Hamir A N, Cutlip R C, Miller J M, et al.: 2001, Preliminary findings on the experimental transmission of chronic wasting disease agent of mule deer to cattle. J Vet Diagn Invest 13:91-96.
22 Hamir A N, Kunkle R A, Cutlip R C, et al.: 2005, Experimental transmission of chronic wasting disease agent from mule deer to cattle by the intracerebral route. J Vet Diagn Invest 17:276-281.
23 Heaton M P, Leymaster K A, Freking B A, et al.: 2003, Prion gene sequence variation within diverse groups of U.S. sheep, beef cattle, and deer. Mamm Genome 14:765-777.
24 Higgins D G, Sharp P M: 1988, CLUSTAL: a package for performing multiple sequence alignment on a microcomputer. Gene 73:237-244.
25 Higgins D G, Sharp P M: 1989, Fast and sensitive multiple sequence alignments on a microcomputer. Comput Appl Biosci 5:151-153.
26 Hill A F, Desbruslais M, Joiner S, et al.: 1997, The same prion strain causes vCJD and BSE. Nature 389:448-450, 526.
27 Hunter N, Goldmann W, Smith G, Hope J: 1994, Frequencies of PrP gene variants in healthy cattle and cattle with BSE in Scotland. Vet Rec 135:400-403.
28 Kimberlin R H: 1993, Bovine spongiform encephalopathy: an appraisal of the current epidemic in the United Kingdom. Intervirology 35:208-218.
28A Kovacs G G et al: 2005, Genetic prion disease: the EUROCJD experience. Hum Genet 118:166-174.
29 Milhavet O, Lehmann S: 2002, Oxidative stress and the prion protein in transmissible spongiform encephalopathies. Brain Res Brain Res Rev 38:328-339.
30 Miller J M, Jenny A L, Taylor W D, et al.: 1994, Detection of prion protein in formalin-fixed brain by hydrated autoclaving immunohistochemistry for the diagnosis of scrapie in sheep. J Vet Diagn Invest 6:366-368.
31 Mouillet-Richard S, Ermonval M, Chebassier C, et al.: 2000, Signal transduction through prion protein. Science 289:1925-1928.
32 Neibergs H L, Ryan A M, Womack J E, et al.: 1994, Polymorphism analysis of the prion gene in BSE-affected and unaffected cattle. Anim Genet 25:313-317.
32A Novakofski J et al.: 2005, Prion biology relevant to bovine spongiform encephalopathy. J Anim Sci 83:1455-1476.
34 Onodera T, Kim C K: 2006, BSE situation and establishment of Food Safety Commission in Japan. J Vet Sci 7:1-11.
35 Parchi P, Gambetti P: 1995, Human prion diseases. Curr Opin Neurol 8:286-293.
36 Prusiner S B: 1998, The prion diseases. Brain Pathol 8:499-513.
37 Prusiner S B: 1997, Prion diseases and the BSE crisis. Science 278:245-251.
38 Prusiner S B: 1998, Prions. Proc Natl Acad Sci USA 95:13363-13383.
39 Prusiner S B, Groth D F, McKinley M P, et al.: 1981, Thiocyanate and hydroxyl ions inactivate the scrapie agent. Proc Natl Acad Sci USA 78:4606-4610.
40 Saegerman C, Speybroeck N, Roels S, et al.: 2004, Decision support tools for clinical diagnosis of disease in cows with suspected bovine spongiform encephalopathy. J Clin Microbiol 42:172-178.
41 Sander P, Hamann H, Drogemuller C, et al.: 2005, Bovine prion protein gene (PRNP) promoter polymorphisms modulate PRNP expression and may be responsible for differences in bovine spongiform encephalopathy susceptibility. J Biol Chem 280:37408-37414.
42 Sander P, Hamann H, Pfeiffer I, et al.: 2004, Analysis of sequence variability of the bovine prion protein gene (PRNP) in German cattle breeds. Neurogenetics 5:19-25.
43 Stack M J, Balachandran A, Chaplin M, et al.: 2004, The first Canadian indigenous case of bovine spongiform encephalopathy (BSE) has molecular characteristics for prion protein that are similar to those of BSE in the United Kingdom but differ from those of chronic wasting disease in captive elk and deer. Can Vet J 45:825-830.
44 Stack M J, Chaplin M J, Clark J: 2002, Differentiation of prion protein glycoforms from naturally occurring sheep scrapie, sheep-passaged scrapie strains (CH1641 and SSBP1), bovine spongiform encephalopathy (BSE) cases and Romney and Cheviot breed sheep experimentally inoculated with BSE using two monoclonal antibodies. Acta Neuropathol (Berl) 104:279-286.
45 Stevenson M A, Morris R S, Lawson A B, et al.: 2005, Area-level risks for BSE in British cattle before and after the July 1988 meat and bone meal feed ban. Prev Vet Med 69:129-144.
46 Thompson J D, Higgins D G, Gibson T J: 1994, CLUSTAL W: improving the sensitivity of progressive multiple sequence alignment through sequence weighting, position-specific gap penalties and weight matrix choice. Nucleic Acids Res 22:4673-4680.
47 Wear A, Henderson K, Webster K, Patel I: 2005, A comparison of rapid bovine spongiform encephalopathy testing methods on autolyzed bovine brain tissue. J Vet Diagn Invest 17:99-102.
48 Wells G A, McGill I S: 1992, Recently described scrapie-like encephalopathies of animals: case definitions. Res Vet Sci 53:1-10.
49 Wells G A, Wilesmith J W: 1995, The neuropathology and epidemiology of bovine spongiform encephalopathy. Brain Pathol 5:91-103.
50 Wilesmith J W, Ryan J B, Atkinson M J: 1991, Bovine spongiform encephalopathy: epidemiological studies on the origin. Vet Rec 128:199-203.
51 Wilesmith J W, Ryan J B, Hueston W D, Hoinville L J: 1992, Bovine spongiform encephalopathy: epidemiological features 1985 to 1990. Vet Rec 130:90-94.
52 Yamakawa Y, Hagiwara K, Nohtomi K, et al.: 2003, Atypical proteinase K-resistant prion protein (PrPres) observed in an apparently healthy 23-month-old Holstein steer. Jpn J Infect Dis 56:221-222.
53 Zhang C C, Steele A D, Lindquist S, Lodish H F: 2006, Prion protein is expressed on long-term repopulating hematopoietic stem cells and is important for their self-renewal. Proc Natl Acad Sci USA 103:2184-2189.

I claim:

1. A method for identifying a bovine animal as having increased susceptibility to bovine spongiform encephalopathy, comprising determining if the prion protein of a bovine comprises five, six, or seven octapeptide repeat region sequences, and further determining the presence of a lysine (K) amino acid in said bovine prion protein at a position selected from the group consisting of a position corresponding to position 211 of SEQ ID NO: 14 wherein said protein comprises six octapeptide repeat region sequences, a position corresponding to position 211 of SEQ ID NO: 14 wherein said protein comprises five octapeptide repeat region sequences, and a position corresponding to position 211 of SEQ ID NO: 14 wherein said protein comprises seven octapeptide repeat region sequences, further wherein the presence of said lysine at said position is indicative of increased susceptibility to bovine spongiform encephalopathy.

2. The method of claim 1 further comprising removing from breeding or from human food and animal feed supplies those bovine wherein the presence of said lysine (K) is determined.

* * * * *